United States Patent
Wagner et al.

(10) Patent No.: US 6,689,940 B2
(45) Date of Patent: Feb. 10, 2004

(54) NUCLEIC ACID ENCODING THE ARABIDOPSIS ELF3 PROTEIN AND A METHOD OF USING IT TO ALTER PHOTOPERIOD IN PLANTS

(75) Inventors: Ry Wagner, Eugene, OR (US); Karen A. Hicks, Mt. Vernon, OH (US); Michelle T. Z. Spence, Capitola, WA (US); Henriette Foss, Eugene, OR (US); Xiang Liang Liu, Eugene, OR (US); Michael F. Covington, San Diego, CA (US)

(73) Assignee: The State of Oregon acting by and through the State Board of Higher Education on behalf of the University of Oregon, Eugene, OR (US)

( * ) Notice: Subject to any disclaimer, the term of this patent is extended or adjusted under 35 U.S.C. 154(b) by 0 days.

(21) Appl. No.: 09/746,801

(22) Filed: Dec. 20, 2000

(65) Prior Publication Data

US 2002/0083494 A1 Jun. 27, 2002

Related U.S. Application Data

(63) Continuation-in-part of application No. 09/513,057, filed on Feb. 24, 2000, now Pat. No. 6,433,251, and a continuation-in-part of application No. PCT/US99/18747, filed on Aug. 17, 1999.
(60) Provisional application No. 60/096,802, filed on Aug. 17, 1998.

(51) Int. Cl.$^7$ .............. A01H 5/00; C12N 1/21; C12N 15/82; C12N 15/29

(52) U.S. Cl. ............ 800/298; 800/290; 800/323; 435/419; 435/252.3; 536/23.6

(58) Field of Search .............. 536/23.6; 800/278, 800/290, 298, 306, 317.1, 313, 317.4, 312, 317.3, 320, 320.2, 316, 320.1, 314, 320.3, 323, 286; 435/419, 412, 414, 415

(56) References Cited

U.S. PATENT DOCUMENTS

| | | | |
|---|---|---|---|
| 4,990,607 A | 2/1991 | Katagiri et al. | |
| 5,563,032 A | * 10/1996 | Fields et al. | 435/5 |
| 5,811,536 A | 9/1998 | Yanofsky | 536/23.6 |
| 6,002,069 A | 12/1999 | Yanofsky | 800/290 |

FOREIGN PATENT DOCUMENTS

WO  WO 00/09658  2/2000

OTHER PUBLICATIONS

Covington et al, 2001, Plant Cell 13:1305–1315.*
GardenWeb Glossary of Botanical Terms, at glossary.gardenweb.com/glossary/, accessed Jan. 6, 2003.*
Carre', ELF3: a circadian safeguard to buffer effects of light, Jan. 2002, Plant Science, vol. 7, No. 1, pp. 4–6.*
Hicks et al., Early Flowering3 Encodes a Novel Protein That Regulates Circadian Clock Function and Flowering in Arabidopsis, Jun. 2001, The Plant Cell, vol. 13, pp. 1281–1292.*
Hill et al., Functional Analysis of Conserved Histidines in ADP–Glucose Pyrophosphorylasr from *Escherichia coli*, 1998, Biochemical and Biophysical, vol. 244, pp. 573–577.*
Lazar et al., Transforming Growth Factorα: Mutation of Aspartic Acid 47 and Leucine 48 Results in Different Biological Activites, Mach 1988, Molecular and Cellular Biology, vol. 8, No. 3, pp. 1247–1252.*
Town et al., Accession No. BH456629.*
Puzio et al., "A New Nematode Responsible Gene in *Arabidopsis thaliana*," Database SPTREML–11, O04419, Mar. 21, 1997.
Puzio et al., Database Genebank, Accession No. O04419, Jul. 1, 1997.
Shannon et al., "A Mutation in the Arabidopsis TFL1 Gene Affects Inflorescence Meristem Development," *The Plant Cell* 3:877–892, 1991.
Zagotta et al., "Early–flowering Mutants of *Arabidopsis thaliana*," *Aust. J. Plant Physiol.*, 19:411–418, 1992.
Weigel et al., "Leafy Controls Floral Meristem Identity in Arabidopsis," *Cell*, 69:843–859, May 29, 1992.
Foden–Vencil, "Oregon research team studies genetic manipulation of plants," *Oregonian* Science section, Nov. 5, 1992.
"UO Molecular Biologist Studying Genes that Make Plants Flower," *Advance Science & Technology Institute*, University of Oregon, p. 5, 1994.
Newman et al., 21244 CD4–14 *Arabidopsis thaliana* cDNA clone F5H5T3, GenBank Accession # N96569, Jun. 5, 1998.
Hicks et al., "*Arabidopsis* early–flowering mutants reveal multiple levels of regulation in the vegetative–to–floral transition," *Cell Dev. Biol.*, 7:409–418, 1996.
Zagotta et al., "The *Arabidopsis* ELF3 gene regulates vegetative photomorphogenesis and the photoperiodic induction of flowering," *Plant J.*, 10(4):691–702, 1996.
Hicks et al., "Conditional Circadian Dysfunction of the *Arabidopsis* early–flowering 3 Mutant," *Science*, 274:790–792, Nov. 1, 1996.

(List continued on next page.)

Primary Examiner—Amy J. Nelson
Assistant Examiner—Anne Kubelik
(74) Attorney, Agent, or Firm—Klarquist Sparkman, LLP

(57) ABSTRACT

The nucleic acid that encodes the Arabidopsis ELF3 protein, which is involved in photoperiodism and circadian rhythms, is disclosed. This nucleic acid may be introduced into plants in order to alter the photoperiodic and/or circadian clock-based gene expression of the plants.

10 Claims, 4 Drawing Sheets

OTHER PUBLICATIONS

Puzio et al., Nematode Responsive Protein, EMBL Accession No. Y11994, Jun. 20, 1997.

Wang and Tobin, "Constitutive Expression of the *Circadian Clock Associated 1* (*CCA1*) Gene Disrupts Circadian Rhythms and Suppresses Its Own Expression," *Cell*, 93:1207–1217, Jun. 25, 1998.

Schaffer et al., "The *late elongated hpocotyl* Mutation of *Arabidopsis* Disrupts Circadian Rhythms and the Photoperiodic Control of Flowering," *Cell*, 93:1219–1229, Jun. 26, 1998.

Puzio et al., "Isolation of a gene from *Arabidopsis thaliana* related to nematode feeding structures," *Gene*, 239:163–175, 1999.

* cited by examiner

BLOCK I:
```
AtELF3         13  PMFPPLHVID ADKGG-PRAP PRHKMALYEQ LSIPSQRF    49
AtEEC          15  PIFPPVHVID TGRGG-LSQQ FDGHTMSLVS SKRFNLPS    49
cardamineELF3  13  PMFPRLHVID ADEGG-PRAP PRHKMALYEQ LSIPSERF    49
tomatoELF3     13  PMFPPINVID TEKGG-PRAP PRHKMALYEQ LSIPSQRY    49
riceELF3       22  PLFPRLHVRD AAKGGGPRAP PRHKMALYEQ FTVPSHRF    59
```

BLOCK II:
```
AtELF3         317 SPDDVVGILG QYRFHRARKA IAHQQRVFAV QLFELHPLIH VQRLIAASP  365
AtEEC          238 SSYDIARVIC EFRRHMPTY  MIHQQKIFAG QVFELHRLIM VQHHVAKSP  285
cELF3          291 SPDDIVGALC QRFHRARKA ITHQQRVFAV QLFSLHRLIR VQRLIAGSP  339
tELF3          341 SPDDIVGIIC LRRFHFAPRA IVHIQRVFAI QVFELIHRLIF VQRLIAGST  389
rELF3          394 SFDKIVGAIC TKHFHFAPRA IMHIQRVFAV QVFELIKLVE VQRLIAAS F  442
maizeELF3        ? SPDDVISAIG PHHFWKAKFA IVHQQRVFAV QVFELHRLIK VQKLIAASP    ?
```

BLOCK III:
```
AtELF3         462 PPPSGNHQQV LIPVMSPSEG LIYKP  469
AtEEC          358 PFP-G---QH  LVP ITDEDG LVYKP  379
cELF3          441 PFPSG--QQI LIPVMSPSEG LIYKE  464
tELF3          485 QQPSG-H-QH LIFVHFSEG  LVYEP  508
rELF3          544 -QPPQH--QH LVFVMSILES LVSKI  565
mELF3            ? --------QH LIPVMSPSEG LVYKP    ?
```

BLOCK IV:
```
AtELF3         660 RVIHVVPHHA KLASENAARI FQSIQEER  691
AtEEC          505 RAIIAVIHHS TSAHHAAKI  FRFIQEER  536
cELF3          577 RVIHVVPHHA KLHHHHN---  --------  577
tELF3          677 RVIHAVPHIA RSATEIVARI FQSIQQER  704
rELF3          729 NVIHVVPHHS RTASESAARI FRSIQMER  756
mELF3            ? RVIRVVPHTA RTASESAARI FRSIQMER    ?
```

Table 1. *Arabidopsis* seedlings overexpressing ELF3 have a reduced sensitivity to red light in hypocotyl elongation and flower late in LD. Mean hypocotyl length in millimeter and flowering time ± SE are indicated. Number of plants measured for each character and genotype is indicated in parenthesis

| Genotype | Hypocotyl Length in millimeter | Flowering Time As Number of Leaves at 1 cm Bolt | | Flowering Time As Days to 1 cm Bolt | |
|---|---|---|---|---|---|
| | | LD | SD | LD | SD |
| COL-0 | 5.69 ± 0.55 (21) | 10.8 ± 1.36 (20) | 64.60 ± 5.10 (10) | 29.00 ± 2.02 (20) | 102.4 ± 6.41 (10) |
| ELF3-OX | 2.96 ± 0.52 (27) | 42.5 ± 4.42 (16) | 57.03 ± 1.37 (47) | 60.56 ± 7.53 (16) | 96.96 ± 0.92 (47) |
| *elf3-1* | 12.40 ± 0.94 (27) | 5.15 ± 0.73 (20) | 9.65 ± 2.95 (17) | 20.75 ± 1.26 (20) | 47.06 ± 6.59 (17) |
| phyB-9 | 14.69 ± 0.86 (20) | 7.17 ± 1.34 (18) | NA | 25.83 ± 1.98 (18) | NA |
| phyB/ELF3-OX | 10.09 ± 0.70 (19) | 44.07 ± 5.21 (27) | NA | 64.37 ± 9.58 (27) | NA |

FIGURE 3

Features of the predicted 695 amino acid ELF3 protein

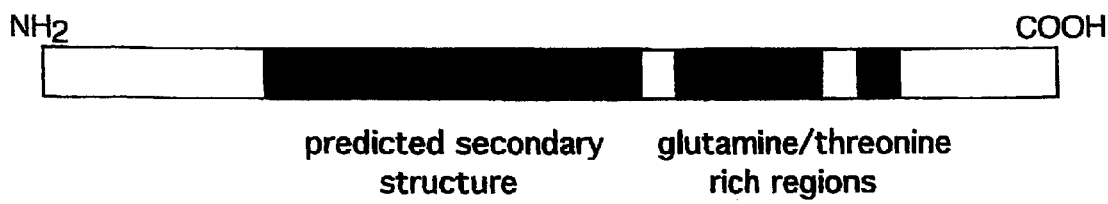

predicted secondary structure     glutamine/threonine rich regions

**Molecular basis of the *elf3* mutations**

| | |
|---|---|
| elf3-1 | C to T change in exon 3 (stop) |
| elf3-2 | ~1.5 kb C-terminal deletion |
| elf3-3 | G to T change in exon 2 (stop) |
| elf3-4 | 11 bp deletion in exon 1 (stop) |
| elf3-5 | C to T change in exon 1 (stop) |
| elf3-6 | AG to AA change in the exon 4 splice acceptor site |
| elf3-7 | G to A change in the exon 1 splice donor site* |
| | *makes ~ 20% full length wild type *ELF3* mRNA |
| elf3-8 | unknown |
| elf3-9 | unknown |

FIGURE 4

ID=NUCLEIC ACID ENCODING THE ARABIDOPSIS ELF3 PROTEIN AND A METHOD OF USING IT TO ALTER PHOTOPERIOD IN PLANTS

CROSS REFERENCE TO RELATED CASES

This is a continuation-in-part of U.S. application Ser. No. 09/513,057, filed Feb. 24, 2000, now U.S. Pat. No. 6,433,251 and also a continuation-in-part of International Application No. PCT/US99/18747, filed Aug. 17, 1999, which claims the benefit of U.S. Provisional Application No. 60/096,802, filed Aug. 17, 1998. All of these applications are incorporated herein in their entirety.

FIELD OF THE INVENTION

This invention relates to genes that regulate circadian clock functions and photoperiodism in plants, and relates in particular to the ELF3 gene. Aspects of the invention include the purified ELF3 gene product (ELF3 protein), as well as nucleic acid molecules encoding this gene product. Nucleic acid vectors, transgenic cells, and transgenic plants having modified ELF3 activity are also provided.

BACKGROUND OF THE INVENTION

Shoot development in flowering plants is a continuous process ultimately controlled by the activity of the shoot apical meristem. Apical meristem activity during normal plant development is sequential and progressive, and can be summarized as a series of overlapping phases: vegetative→inflorescence→floral (V→I→F). Over the past 50 years many models have been proposed for the control of the vegetative-to-floral transition. These models range from simple single pathway models to complex multiple pathway models, and are largely based on physiological studies (for review, see Bernier, 1988). Modem techniques provide researchers with genetic and molecular methods that can be used to further investigate the control of V→I→F transitions.

One such modem technique now routinely practiced by plant molecular biologists is the production of transgenic plants carrying a heterologous gene sequence. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,268,526 (modification of phytochrome expression in transgenic plants); U.S. Pat. No. 5,719,046 (production of herbicide resistant plants by introduction of bacterial dihydropteroate synthase gene); U.S. Pat. No. 5,231,020 (modification of flavenoids in plants); 5,583,021 (production of virus resistant plants); and U.S. Pat. Nos. 5,767,372 and 5,500,365 (production of insect resistant plants by introducing *Bacillus thuringiensis* genes).

Light quality, photoperiod, and temperature often act as important, and for some species essential, environmental cues for the initiation of flowering. However, there is very little information on the molecular mechanisms that directly regulate the developmental pathway from reception of the inductive light signal(s) to the onset of flowering and the initiation of floral meristems. The analysis of floral transition mutants in pea (*Pisum sativum*) (see Murfet, 1985) and Arabidopsis (see Koornneef et al., 1991) has demonstrated that at least part of the genetic hierarchy controlling flowering onset is responsive to the number of hours of light perceived by a plant within a 24 hour light/dark cycle. The monitoring of the length of the light period is referred to as the photoperiodic response. Photoperiodic responses have long been thought to be tied to one or more biological clocks that regulate many physiological and developmental processes on the basis of an endogenous circadian rhythm.

Many important physiological and developmental plant processes are influenced by circadian rhythms. These include the induction of gene transcription, leaf movement, stomatal opening, and the photoperiodic control of flowering. While the relationship of these plant processes to the circadian rhythm has long been recognized, the genetic analysis of circadian rhythms in plants has only recently begun. Most of the genetic analysis of circadian regulation has been performed with Drosophila and *Neurospora crassa*, where mutational studies have led to the isolation of the per and frq genes, respectively (Hall, 1990; Dunlap, 1993). These genes are thought to encode components of the circadian oscillator, in part because, while null alleles cause arrhythmic responses, alleles of these genes exist that produce either long or short period responses. Transcriptional production of per and frq mRNA cycles on a twenty-four hour period, and both genes regulate their own expression (Edery et al., 1994; Aronson et al., 1994).

Arabidopsis is a quantitative long-day (LD) plant—wild-type plants will initiate flowering more quickly when grown under LD light conditions than when grown under short-day (SD) light conditions. In order to identify genes required for floral initiation and development, populations of *Arabidopsis thaliana* ecotype Columbia grown in SD conditions have been screened for early-flowering mutants. Isolated mutants were then examined for additional shoot development anomalies, and those with discreet shoot phenotypes related to meristem function or light perception were considered for further analysis. Such mutants may identify genes that are part of functionally redundant pathways that operate, to varying degrees, as "fail-safe" mechanisms for ensuring shoot growth and reproductive development. Examples of such functionally redundant pathways have been described in studies of Drosophila (e.g., Hülskamp et al., 1990) and *C. elegans* (e.g., Lambie and Kimble, 1991). The key genes identified by these Arabidopsis screens were the TERMINAL FLOWER 1 (TFL1) gene and the EARLY-FLOWERING 3 (ELF3) gene (Shannon and Meeks-Wagner, 1991; Zagotta et al., 1992).

The early-flowering (elf3) mutant of Arabidopsis is insensitive to photoperiod with regard to floral initiation. Plants homozygous for a mutation in the ELF3 locus flower at the same time in LD and SD growth conditions, whereas floral initiation of wild-type plants is promoted by LD growth conditions (Zagotta et al., 1992; Zagotta et al., 1996). In LD conditions, the flowering time of the elf3-1 heterozygote is intermediate between wild-type and the homozygous mutant. In addition to being photoperiod-insensitive, all elf3 mutants display the long hypocotyl phenotype characteristic of plants defective in light reception or the transduction of light signals (Zagotta et al., 1992; Zagotta et al., 1996). The majority of long hypocotyl mutants that have been identified are defective in red light-mediated inhibition of hypocotyl elongation. In contrast, elf3 mutants are primarily defective in blue light-dependent inhibition of hypocotyl elongation, although they are also partially deficient in red light-dependent inhibition of hypocotyl elongation (Zagotta et al., 1996).

The availability of the ELF3 gene would facilitate the production of transgenic plants having altered circadian clock function and programmed photoperiodic responses. It is to such a gene that the present invention is directed.

SUMMARY OF THE INVENTION

The invention provides an isolated ELF3 gene from Arabidopsis that is shown to complement the elf3 photoperiod-insensitive flowering and elongated hypocotyl defects when introduced into elf3 mutant plants.

One aspect of this invention is a purified protein having ELF3 protein biological activity. The prototypical Arabidopsis ELF3 protein has the amino acid sequence shown in SEQ ID NO: 2. Variants of this protein that differ from SEQ ID NO: 2 by one or more conservative amino acid substitutions are also provided, as are homologs of the ELF3 protein. Such homologs typically share at least 60% sequence identity with the sequence shown in SEQ ID NO: 2. Nucleic acid molecules encoding these proteins are also part of this invention. Such nucleic acid molecules include those having the nucleotide sequences set forth in SEQ ID NO: 1, SEQ ID NO: 3, and SEQ ID NO:4.

Recombinant nucleic acid molecules in which a promoter sequence is operably linked to any of these ELF3 protein-encoding nucleic acid sequences are further aspects of this invention. The invention also provides cells transformed with such a recombinant nucleic acid molecule and transgenic plants comprising the recombinant nucleic acid molecule. Such transgenic plants may be, for instance, Arabidopsis, pepper, tomato, tobacco, broccoli, cauliflower, cabbage, canola, bean, soybean, rice, corn, wheat, barley, citrus, cotton, cassava and walnut, trees such as poplar, oak, maple, pine, spruce, and other conifers, and ornamental plants (e.g., petunias, orchids, carnations, roses, impatiens, pansies, lilies, snapdragons, geraniums, and so forth).

A further aspect of this invention is an isolated nucleic acid molecule or oligonucleotide comprising 15, 20, 30, 50, or 100 contiguous nucleotides of the sequence shown in SEQ ID NOs: 1, 3, or 4. Such nucleic acid molecules or oligonucleotides may be operably linked to a promoter sequence, and may be in the sense or antisense orientation in relation to such a promoter. The invention also includes cells and plants transformed with such recombinant nucleic acid molecules, with or without an attached promoter.

Further embodiments of this invention include isolated nucleic acid molecules that hybridize under specified hybridization conditions to the nucleic acid sequence set forth in SEQ ID NO: 1, and that encode a protein having ELF3 protein biological activity. Closely related ELF3 gene homologs may be detected by hybridization under stringent conditions, whereas less closely related homologs may be detected by hybridization at low stringency. Appropriate wash conditions for stringent hybridization may be 55° C., 0.2× SSC and 0.1% SDS for 1 hour. Appropriate wash conditions for low stringency hybridization may be 50° C., 2× SSC, 0.1% for 3 hours. Such a hybridizing isolated nucleic acid molecule may be operably linked to a promoter for expression in plants. Cells transformed with such a recombinant nucleic acid molecule, and transgenic plants that comprise such a molecule, are also provided.

The invention also provides the 5' regulatory region of the ELF3 gene. This regulatory region, or parts thereof, may be used to obtain ELF3-like circadian-rhythm expression of particular genes. For example, the ELF3 5' regulatory region may be operably linked to an open reading frame of a gene of interest, and the resulting recombinant construct may be introduced into a plant by transformation. One embodiment of an ELF3 regulatory region is about nucleotides 1 through about 1900 of the 5' upstream region shown in SEQ ID NO: 5.

BRIEF DESCRIPTION OF THE DRAWINGS

FIG. 1. Sequence Comparison of ELF3 Homologs.

Multiple-sequence alignment of ELF3 (residues 1–695 of SEQ ID NO: 2) and several putative ELF3 homologs from *Arabidopsis thaliana* (Essence of ELF3 Consensus, EEC) (residues 1–540 of SEQ ID NO: 33) and other plant species (*Cardamine oligosperma* (residues 1–577 of SEQ ID NO: 13), tomato (residues 1–179 of SEQ ID NO: 24 and residues 1–389 of SEQ ID NO: 23), rice (residues 1–760 of SEQ ID NO: 27), and maize (residues 117–247 of SEQ ID NO: 29)). Protein designations are given on the left in the same order. Amino acid residues are numbered on the right. Residues shaded in black indicate identity of at least three ELF3/ELF3-related sequences in the alignment; light-shaded residues indicate similarity to consensus. Nucleotide sequences from *C. oligosperma* (a member of the family Brassicaceae) were obtained by sequencing polymerase chain reaction products using degenerate oligos to the Arabidopsis ELF3 gene and genomic DNA or cDNA prepared from *C. oligosperma* seedlings. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

FIG. 2. Sequence Comparison of ELF3 Homologs Showing Consensus Boxes.

Multiple-sequence alignment shows four highly conserved regions within ELF3 and putative ELF3 homologs from *Arabidopsis thaliana* (Essence of ELF3 Consensus, EEC) and other plant species (*Cardamine oligosperma*, tomato, rice, and maize). Protein designations are given on the left in the same order. Amino acid residues are numbered on both the right and left. Residues shaded in black indicate identity of at least three ELF3/ELF3-related sequences in the alignment; light-shaded residues indicate similarity to consensus. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

GenBank accession numbers for ELF3 and putative ELF3 homologs are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [*Lycopersicon esculentum* Expressed Sequence Tags (ESTs) from Clemson University Genomics Institute: AW093790 (Oct. 18, 1999), AI894513 (July 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), mELF3 (*Zea mays* EST from Stanford University Genome Center: AI637184, published Apr. 26, 1999).

In Block I, the "AtELF3" amino acid sequence corresponds to residues 13–49 of SEQ ID NO: 2; the "AtEEC" amino acid sequence corresponds to residues 15–51 of SEQ ID NO: 33; the "cardamineELF 3" amino acid sequence corresponds to residues 13–49 of SEQ ID NO: 13; the "tomatoELF3" amino acid sequence corresponds to residues 13–49 of SEQ ID NO: 24; and the "riceELF3" amino acid sequence corresponds to residues 22–59 of SEQ ID NO: 27.

In Block II, the "AtELF3" amino acid sequence corresponds to residues 317–365 of SEQ ID NO: 2; the "AtEEC" amino acid sequence corresponds to residues 238–286 of SEQ ID NO: 33; the "cELF3" amino acid sequence corresponds to residues 291–339 of SEQ ID NO: 13; the "tELF3" amino acid sequence corresponds to residues 22–70 of SEQ ID NO: 23; the "rELF3" amino acid sequence corresponds to residues 394–442 of SEQ ID NO: 27; and the "maizeELF3" amino acid sequence corresponds to residues 22–70 of SEQ ID NO: 57.

In Block III, the "AtELF3" amino acid sequence corresponds to residues 462–486 of SEQ ID NO: 2; the "AtEEC" amino acid sequence corresponds to residues 358–379 of SEQ ID NO: 33; the "cELF3" amino acid sequence corresponds to residues 441–464 of SEQ ID NO: 13; the "tELF3" amino acid sequence corresponds to residues 167–189 of SEQ ID NO: 23; the "rELF3" amino acid sequence corresponds to residues 544–565 of SEQ ID NO: 27; and the "mELF3" amino acid sequence corresponds to residues 162–178 of SEQ ID NO: 57.

In Block IV, the "AtELF3" amino acid sequence corresponds to residues 660–687 of SEQ ID NO: 2; the "AtEEC" amino acid sequence corresponds to residues 505–532 of SEQ ID NO: 33; the "cELF3" amino acid sequence corresponds to residues 639–653 of SEQ ID NO: 14; the "tELF3" amino acid sequence corresponds to residues 358–385 of SEQ ID NO: 23; the "rELF3" amino acid sequence corresponds to residues 729–756 of SEQ ID NO: 27; and the "mELF3" amino acid sequence corresponds to residues 285–312 of SEQ ID NO: 57.

FIG. 3 is a Table showing growth and flowering characteristics of Arabidopsis seedlings over-expressing ELF3 (ELF3-OX), seedlings that are mutant in ELF3 (elf-3).

FIG. 4 shows the features of the predicted 695 amino acid ELF3 protein, and the molecular basis of the several elf3 mutations.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the cDNA and amino acid sequence of Arabidopsis ELF3.

SEQ ID NO: 2 shows the amino acid sequence of Arabidopsis ELF3 protein.

SEQ ID NO: 3 shows the genomic sequence of Arabidopsis ELF3. The sequence comprises the following regions:

| Nucleotides | Feature |
|---|---|
| 1–142 | promoter region |
| 143–424 | exon 1 (5' UTR) |
| 425–644 | exon 1 continued (initiating ATG at 425) |
| 645–1006 | intron 1 |
| 1007–1803 | exon 2 |
| 1804–2983 | intron 2 |
| 2984–3037 | exon 3 |
| 3038–3127 | intron 3 |
| 3128–4142 | exon 4 |
| 4143–4145 | stop codon |
| 4146–4221 | 3' UTR and 3' regulatory region. |

SEQ ID NO: 4 shows the DNA and corresponding amino acid sequence of the Arabidopsis ELF3 ORF.

SEQ ID NO: 5 shows the 4071 base pair Arabidopsis ELF3 5' regulatory region.

SEQ ID NO: 6–11 show primers that can be used to amplify certain portions of the Arabidopsis ELF3 sequence.

SEQ ID NO: 12 shows the cDNA and corresponding amino acid sequence of the Cardamine oligosperma ELF3 ortholog, cELF3. This sequence can also be determined by applying well known computer analyses to the genomic sequence shown in SEQ ID NO: 14 (also referred to as COELF3 $^{-1}$) to determine where the introns and exons are.

SEQ ID NO: 13 (also referred to as COELF3 $^{-2}$) shows the amino acid sequence of the Cardamine oligosperma ELF3 ortholog, cELF3.

SEQ ID NO: 14 (also referred to as COELF3 $^{-1}$) shows the genomic sequence of the Cardamine oligosperma ELF3 ortholog, cELF3.

SEQ ID NO: 15 shows a partial DNA sequence (also referred to as PEAELF~2) of the pea ELF 3 ortholog.

SEQ ID NO: 16 (also referred to as PEAELF~1) shows the amino acid sequence of the partial pea ELF 3 ortholog.

SEQ ID NO: 17 (also referred to as BROCCA~2) shows the amino acid sequence of the broccoli/cauliflower EEC protein.

SEQ ID NO: 18 shows a partial DNA (also referred to as GMELF3~2) sequence of the Glycine max (soybean) ELF3 coding region.

SEQ ID NO: 19 (also referred to as GMELF3~1) shows the amino acid sequence of the partial Glycine max (soybean) ELF3 protein.

SEQ ID NO: 20 shows the DNA (also referred to as BROCCA~1) a sequence of the Lycopersicon esculentum (tomato) ELF3 (N-terminus #2) coding region.

SEQ ID NO: 21 shows the DNA (also referred to as LEAFFO~1) sequence of the Lycopersicon esculentum (tomato) ELF3 (N-terminus #1) coding region.

SEQ ID NO: 22 shows the DNA (also referred to as LE5B39~1) sequence of the Lycopersicon esculentum (tomato) coding region.

SEQ ID NO: 23 (also referred to as LEELF3~3) shows the amino acid sequence of the Lycopersicon esculentum (tomato) ELF3 (C-terminus) coding region.

SEQ ID NO: 24 (also referred to as LEELF~2) shows a partial amino acid sequence of the Lycopersicon esculentum (tomato) protein.

SEQ ID NO: 25 (also referred to as LEELF3~1) shows the amino acid sequence of the Lycopersicon esculentum (tomato) ELF3 (N-terminus #2) protein.

SEQ ID NO: 26 shows the DNA (also referred to as OSELF3~2) sequence of the Oryza sativa (rice) ELF3 genomic region.

SEQ ID NO: 27 (also referred to as OSELF3~1) shows the amino acid sequence of the Oryza sativa (rice) ELF3 protein.

SEQ ID NO: 28 shows a partial DNA (also referred to as ZM8CC4~1) sequence of the Zea mays (maize) ELF3 coding region.

SEQ ID NO: 29 (also referred to as ZMELF3~2) shows the amino acid sequence of the partial Zea mays (maize) ELF3 protein.

SEQ ID NO: 30 shows a partial DNA (also referred to as ZMELF3~4) sequence of the Zea mays (maize) ELF3 #2 coding region.

SEQ ID NO: 31 (also referred to as ZMELF3~3) shows the amino acid sequence of the partial Zea mays (maize) ELF3 #2 coding region.

SEQ ID NO: 32 shows the DNA (also known as ATEECG~1) of the Arabidopsis thaliana EEC genomic region.

SEQ ID NO: 33 (also known as ATEECP~1) shows the amino acid sequence of the Arabidopsis thaliana EEC protein.

SEQ ID NO: 34 shows the DNA (also known as ATELF3~1) sequence of the *Arabidopsis thaliana* ELF3 genomic region.

SEQ ID NO: 35 (also known as ATELF3~2) shows the amino acid sequence of the *Arabidopsis thaliana* ELF3 protein.

SEQ ID NO: 36 (also known as MTELF3N1) shows a portion of exon 1, including 5'UTR and start codon, of the *Medicago trunculata* ELF3 cDNA nucleotide sequence. This partial sequence was originally reported in Genbank Accession No. AW690413.

SEQ ID NO: 37 (also known as MTELF3P1) shows the peptide portion of the *Medicago trunculata* ELF3 protein encoded for by SEQ ID NO: 36.

SEQ ID NO: 38 (also known as MTELF3N4) shows a portion of exon 4, including stop codon and 3'UTR, of the *Medicago trunculata* ELF3 nucleotide sequence. This partial sequence was originally reported as Genbank Accession No. AW693560.

SEQ ID NO: 39 (also known as MTELF3P4) shows the peptide portion of the *Medicago trunculata* ELF3 protein encoded for by SEQ ID NO: 38.

SEQ ID NO: 40 (also known as PSELF3N3) shows a portion of exon 3 to exon 4 of the *Pisum sativa* genomic DNA encoding ELF3.

SEQ ID NO: 41 (also known as PSELF3P3) shows the peptide portion of the *Pisum sativa* ELF3 protein encoded for by SEQ ID NO:40.

SEQ ID NO: 42 (also known as PSELF3N4) shows a portion of exon 4 of the *Pisum sativa* genomic DNA encoding ELF3.

SEQ ID NO: 43 (also known as PSELF3P4) shows the peptide portion of the *Pisum sativa* ELF3 protein encoded for by SEQ ID NO: 42.

SEQ ID NO: 44 (also known as GMELF3N) shows a portion of the *Glycine max* cDNA encoding ELF3. This partial sequence was originally reported in Genbank Accession No. AW757137.

SEQ ID NO: 45 (also known as GMELF3P) shows the peptide portion of the *Glycine max* ELF3 protein encoded for by SEQ ID NO: 44.

SEQ ID NO: 46 (also known as XELF3N1) shows a portion of the Xanthium genomic DNA (from exon 3 to exon 4) encoding ELF3.

SEQ ID NO: 47 (also known as XELF3P1) shows the peptide portion of the Xanthium ELF3 protein encoded for by SEQ ID NO: 46.

SEQ ID NO: 48 (also known as XELF3N2) shows a portion of the Xanthium genomic DNA (from exon 3 to exon 4) encoding ELF 3.

SEQ ID NO: 49 (also known as XELF3P2) shows the peptide portion of the Xanthium ELF3 protein encoded for by SEQ ID NO: 48.

SEQ ID NO: 50 (also known as XELF3N4) shows a portion of the Xanthium genomic DNA (a portion of exon 4) encoding ELF3.

SEQ ID NO: 51 (also known as XELF3P4) shows the peptide portion of the Xanthium ELF3 protein encoded for by SEQ ID NO: 50.

SEQ ID NO: 52 (also known as POPELF3N) shows a portion of the Poplar genomic DNA (a portion of exon 4) encoding ELF3.

SEQ ID NO: 53 (also known as POPELF3P) shows the peptide portion of the Poplar ELF3 protein encoded for by SEQ ID NO: 52.

SEQ ID NO: 54 (also known as MIMELF3N) shows a portion of the Mimulus genomic DNA (a portion of exon 4) encoding ELF3.

SEQ ID NO: 55 (also known as MIMELF3P) shows the peptide portion of the Mimulus ELF3 protein encoded for by SEQ ID NO: 54.

SEQ ID NO: 56 (also known as ZMELF3N) shows a portion of the *Zea mays* contig of cDNA/genomic DNA (exon 2, exon 3, intronic sequence, and exon 4, including stop codon and 3'UTR) encoding ELF3. This partial sequence was originally reported in Genbank Accession No. AI637184.

SEQ ID NO: 57 (also known as ZMELF3P) shows the peptide portion of the *Zea mays* ELF3 protein encoded for by SEQ ID NO: 56.

SEQ ID NO: 58 (also known as LEELF3-AN) shows a portion of the Lycopersicon esculentum cDNA (exon 1, exon 2, exon 3, and exon 4, including stop codon and 3'UTR) encoding ELF3.

SEQ ID NO: 59 (also known as LEELF3-AP) shows the peptide portion of the Lycopersicon esculentum ELF3 protein encoded for by SEQ ID NO: 58.

SEQ ID NO: 60 (also known as BRELF3AN) shows a portion of the Broccoli genomic DNA (portion of exon 1, exon 2, exon 3, and portion of exon 4) encoding ELF3.

SEQ ID NO: 61 (also known as BRELF3AP) shows the peptide portion of the Broccoli ELF3 protein encoded for by SEQ ID NO: 60.

SEQ ID NO: 62 (also known as BRELF3BN) shows a portion of the Broccoli genomic DNA (a portion of exon 4) encoding ELF3.

SEQ ID NO: 63 (also known as BRELF3BP) shows the peptide portion of the Broccoli ELF3 protein encoded for by SEQ ID NO: 62.

SEQ ID NOs: 64–68 (also known as C-FWD, D-REV, B-FWD,Pea 1b-C-FWD, and C-REV, respectively) show primers used to amplify ELF3 homologous sequences.

DETAILED DESCRIPTION OF THE INVENTION

I. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

ELF3 gene/ELF3 cDNA: Nucleic acid molecules that encode an ELF3 protein. Nucleic acid molecules that encode the Arabidopsis ELF3 protein are provided in SEQ ID NO: 3 (Arabidopsis ELF3 gene), SEQ ID NO: 1 (Arabidopsis ELF3 cDNA) and SEQ ID NO:4 (Arabidopsis ELF3 open reading frame). The invention includes not only the nucleic acid molecules provided in SEQ ID NOS: 1, 3 and 4, but also homologs and orthologs of these sequences, other nucleic acid molecules that encode ELF3 proteins, and probes and primers that are derived from these sequences.

elf3 mutant: The early-flowering (elf3) mutant of Arabidopsis is insensitive to photoperiod with regard to floral initiation (Zagotta et al., 1992; Zagotta et al., 1996). In addition to being photoperiod-insensitive, all Arabidopsis elf3 mutants display the long-hypocotyl phenotype characteristic of plants defective in light reception or the transduction of light signals (Zagotta et al., 1992; Zagotta et al., 1996). Elf3 mutants are primarily defective in blue light-dependent inhibition of hypocotyl elongation, although elf3 mutants are also partially deficient in red light-dependent inhibition of hypocotyl elongation (Zagotta et al., 1996).

ELF3 protein: A protein having ELF3 protein biological activity and sharing amino acid sequence identity with the amino acid sequence of the prototypical ELF3 protein shown in SEQ ID NO: 2 (the Arabidopsis ELF3 protein). ELF3 proteins that are more distantly related to the prototypical ELF3 protein will share at least 60% amino acid sequence identity with the sequence shown in SEQ ID NO: 2, as determined by the methods described below. More closely related ELF3 proteins may share at least 70%, 75% or 80% sequence identity with the Arabidopsis ELF3 protein. ELF3 proteins that are most closely related to the Arabidopsis protein will have ELF3 protein biological activity and share at least 85%, 90% or 95% sequence identity with the Arabidopsis protein.

ELF3 protein biological activity: The ability of a protein to complement an elf3 mutant. The ability of a protein to complement an elf3 mutant may be readily determined by introducing the gene encoding the protein into an elf3 mutant plant using standard methods. If the encoded protein has ELF3 protein biological activity, this will be manifested as a proportion of the transgenic progeny plants having a wild-type phenotype for those characteristics linked to the elf3 mutant (e.g., photoperiod-insensitive flowering and elongated hypocotyl).

ELF3 promoter: The region of nucleic acid sequence upstream (5') of the ELF3 coding sequence that is responsible for spatial and temporal regulation of ELF3 transcription. ELF3 transcription is circadian regulated, but with an RNA maximum that is "later" in the 24-hour period than that of other known circadian genes, e.g., CAB, CCR2, CCA1 and LHY (Wang and Tobin, 1998; Schaffer et al., 1998). ELF3-like circadian rhythm or cyclic transcriptional regulation refers to this type of a relatively delayed transcription maximum. Because ELF3 transcription reaches a maximal level relatively late in the 24-hour period, the ELF3 promoter will allow for altering the setting of the circadian clock. For instance, if another circadian-regulated gene (e.g., chlorophyll a/b binding protein) is expressed from the ELF3 promoter, the circadian set on this protein will be delayed to match that of ELF3. In addition, the ELF3 promoter may be used to provide altered expression of other genes that are under control of the circadian clock, if clock components and/or regulators such as CCA1 and LHY are driven by the ELF3 promoter instead of their own promoters or a constitutive promoter, for instance the 35S promoter.

The ELF3 promoter region is contained within the 4071 kb 5' regulatory region sequence shown in SEQ ID NO: 5, but one of ordinary skill in the art will appreciate that expression may be controlled by using less than this entire 5' upstream region, e.g., nucleotides 500–4071, 1000–4071, 1500–4071, 2000–4071, 2500–4071, 3000–4071, 3500–4071 or 4000–4071. One embodiment of an ELF3 promoter is about nucleotides 1 through about 1900 of the 5' upstream region shown in SEQ ID NO: 5.

Sequences as short as 50 or 100 nucleotides from within the 5' regulatory region may also be employed. The degree to which such a sequence provides for ELF3-like circadian cyclic transcriptional regulation, when included in an expression vector, can be ascertained by the methods described herein. Thus, the term "biologically active ELF3 promoter" refers to a 5' regulatory region of an ELF3 gene, or a part or a variant of such a region, that, when operably linked to the 5' end of an ORF and introduced into a plant, results in ELF3-like (i.e., relatively late) circadian cyclic transcript expression of the protein encoded by the ORF.

Figure 1:
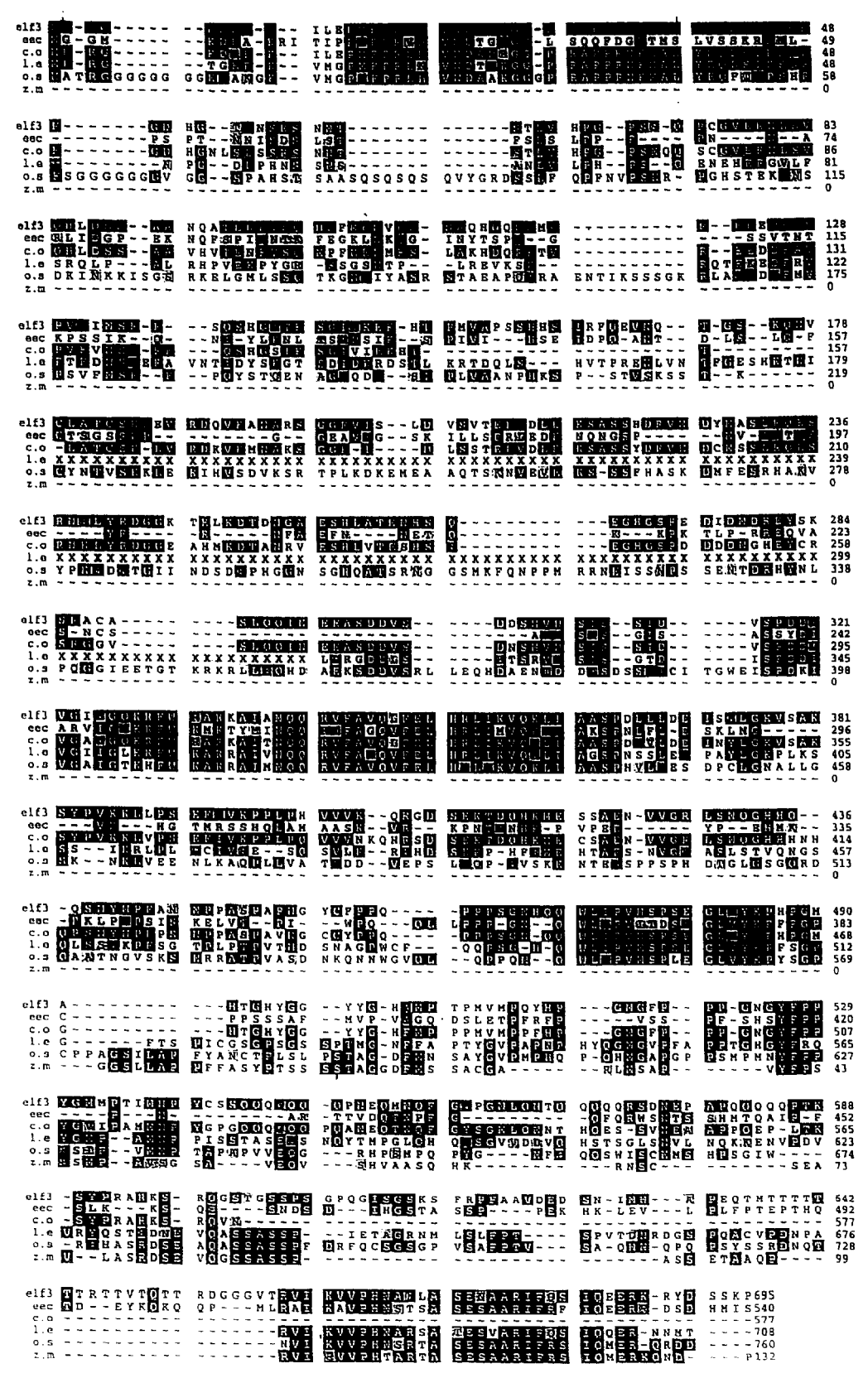

Essence of ELF3 Consensus (EEC): One or more highly conserved regions of amino acid sequence within an ELF3 protein or ELF3 protein homolog. EECs are depicted in FIGS. 1 and 2.

Oligonucleotide: A linear polynucleotide sequence of up to about 100 nucleotide bases in length.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acid molecules, typically DNA oligonucleotides 15 nucleotides or more in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al. (1990). PCR primer pairs can be derived from a known sequence, for example, by using computer programs intended for that purpose such as Primer (Version 0.5, ©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of the Arabidopsis ELF3 cDNA or gene will anneal to a target sequence such as an ELF3 gene homolog from tomato contained within a tomato genomic DNA library with a higher specificity than a corresponding primer of only 15 nucleotides. Thus, in order to obtain greater specificity, probes and primers can be selected that comprise 20, 25, 30, 35, 40, 50 or more consecutive nucleotides of the Arabidopsis ELF3 cDNA or gene sequences.

The invention thus includes isolated nucleic acid molecules that comprise specified lengths of the disclosed ELF3 cDNA or gene sequences. Such molecules may comprise at least 20, 25, 30, 35, 40, 50 or 100 consecutive nucleotides of these sequences and may be obtained from any region of the disclosed sequences. By way of example, the Arabidopsis ELF3 cDNA, ORF and gene sequences may be apportioned into halves or quarters based on sequence length, and the isolated nucleic acid molecules may be derived from the first or second halves of the molecules, or any of the four quarters. The Arabidopsis ELF3 cDNA, shown in SEQ ID NO: 1, can be used to illustrate this. The Arabidopsis ELF3 cDNA is 2518 nucleotides in length and so may be hypothetically divided into about halves (nucleotides 1–1259 and 1260–2518) or about quarters (nucleotides 1–629, 630–1259, 1260–1889 and 1890–2518). Nucleic acid molecules may be selected that comprise at least 20, 25, 30, 35, 40, 50 or 100 consecutive nucleotides of any of these or other portions of the Arabidopsis ELF3 cDNA. Thus, representative nucleic acid molecules might comprise at least 25 consecutive nucleotides of the region comprising nucleotides 1–1259 of the disclosed Arabidopsis cDNA, or of the regions comprising nucleotides 1–1135 or 2502–2518 of the cDNA.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the Arabidopsis ELF3 protein will possess a relatively high degree of sequence identity when aligned using standard methods. Methods of alignment of sequences for comparison are well known in the art. Various programs and alignment algorithms are described in: Smith & Waterman Adv. Appl. Math. 2: 482, 1981; Needleman & Wunsch J. Mol. Biol. 48: 443, 1970; Pearson & Lipman Proc. Natl. Acad. Sci. USA 85: 2444, 1988; Higgins & Sharp Gene, 73: 237–244, 1988; Higgins & Sharp CABIOS 5: 151–153, 1989; Corpet et al. Nuc. Acids Res. 16, 10881–90, 1988; Huang et al. Computer Appls. in the Biosciences 8, 155–65, 1992; and Pearson et al. Meth. Mol. Bio. 24, 307–31, 1994. Altschul et al. (J. Mol Biol. 215:403–410, 1990), presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI BLAST web-site. A description of how to determine sequence identity using this program is available at the help page of the NCBI web-site.

Homologs of the disclosed Arabidopsis ELF3 protein typically possess at least 60% sequence identity counted over full length alignment with the amino acid sequence of Arabidopsis ELF3 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 91%, at least 92%, at least 93%, at least 94% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% or more depending on their similarity to the reference sequence. Methods for determining sequence identity over such short windows are described at the NCBI web-site, frequently asked questions page. One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs. ELF3 homologs will typically also have ELF3 protein biological activity.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to the Arabidopsis ELF3 sequences will typically hybridize to a probe based on either the entire Arabidopsis ELF3 cDNA or selected portions of the cDNA under wash conditions of 0.2× SSC, 0.1% SDS at 55° C. for 1 hour. A more detailed discussion of hybridization conditions, including low stringency conditions, is presented below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Ortholog: Two nucleotide or amino acid sequences are orthologs of each other if they share a common ancestral sequence and diverged when a species carrying that ancestral sequence split into two species. Orthologous sequences are also homologous sequences.

Specific binding agent: An agent that binds substantially only to a defined target. Thus an ELF3 protein specific binding agent binds substantially only the ELF3 protein. As used herein, the term "ELF3 protein specific binding agent" includes anti-ELF3 protein antibodies and other agents that bind substantially only to the ELF3 protein.

Anti-ELF3 protein antibodies may be produced using standard procedures described in a number of texts, including Harlow and Lane (1988). The determination that a particular agent binds substantially only to the ELF3 protein may readily be made by using or adapting routine procedures. One suitable in vitro assay makes use of the Western blotting procedure (described in many standard texts, including Harlow and Lane (1988)). Western blotting may be used to determine that a given ELF3 protein binding agent, such as an anti-ELF3 protein monoclonal antibody, binds substantially only to the ELF3 protein.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules.

Purified: The term purified does not require absolute purity; rather, it is intended as a relative term. Thus, for example, a purified ELF3 protein preparation is one in which the ELF3 protein is more enriched than the protein is in its natural environment within a cell. Generally, a preparation of ELF3 protein is purified such that ELF3 represents at least 5% of the total protein content of the preparation. For particular applications, higher purity may be desired, such that preparations in which ELF3 represents at least 25%, 50% or at least 90% of the total protein content may be employed.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any internal termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. ELF3 Protein and Nucleic Acid Sequences

This invention provides ELF3 proteins and ELF3 nucleic acid molecules, including cDNA and gene sequences. The prototypical ELF3 sequences are the Arabidopsis sequences, and the invention provides for the use of these sequences to produce transgenic plants, such as corn and rice plants, having increased or decreased levels of ELF3 protein.

a. Arabidopsis ELF3

The Arabidopsis ELF3 genomic sequence is shown in SEQ ID NO: 3. The sequence comprises three introns and four exons, and encodes a protein that is 696 amino acids in length (SEQ ID NO: 2 shows the amino acid sequence of the ELF3 protein). The Arabidopsis ELF3 protein shares no significant homology to any known published proteins with assigned function. However, one published Arabidopsis EST (GenBank # N96569; Newman et al., 1994) overlaps nucleotides 853–2088 of the Arabidopsis ELF3 open reading frame (ORF) (SEQ ID NO: 4) (nucleotides 1136–2501 of the Arabidopsis ELF3 cDNA, SEQ ID NO: 1).

GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [Lycopersicon esculentum Expressed Sequence Tags (ESTs) from Clemson University Genomics Institute: AW093790 (October 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

The cDNA corresponding to the ELF3 gene is shown in SEQ ID NO: 1, and the ELF3 ORF is shown in SEQ ID NO: 4. As described below, the Arabidopsis ELF3 protein has ELF3 biological activity, i.e., it complements the defective characteristics of photoperiod-insensitive flowering and elongated hypocotyl in elf3 mutant plants when the ELF3 gene sequence is introduced into these plants and the ELF3 protein is thereby expressed. In addition, ELF3 proteins contain one or more ESSENCE of ELF3 CONSENSUS (EEC) regions (see FIG. 2).

With the provision herein of the Arabidopsis ELF3 cDNA and gene sequences, the polymerase chain reaction (PCR) may now be utilized as a preferred method for producing nucleic acid sequences encoding the Arabidopsis ELF3 protein. For example, PCR amplification of the Arabidopsis ELF3 cDNA sequence may be accomplished either by direct PCR from a plant cDNA library or by reverse-transcription PCR (RT-PCR) using RNA extracted from plant cells as a template. Methods and conditions for both direct PCR and RT-PCR are known in the art and are described in Innis et al. (1990). Any plant cDNA library would be useful for direct PCR. The ELF3 gene sequences can be isolated from other libraries, for instance the IGF Arabidopsis BAC library (Mozo et al. 1998) The selection of PCR primers will be made according to the portions of the ELF3 cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al (1990), Sambrook et al. (1989), and Ausubel et al. (1992). By way of example only, the Arabidopsis ELF3 cDNA molecule as shown in SEQ ID NO: 1 (excluding the poly A tail) may be amplified using the following combination of primers:

```
                                              (SEQ ID NO:6)
primer 1:  5'TGAAAACTCACTTTGGTTTTGTTTG 3'

(SEQ ID NO:6)
primer 2:  5'AAGACAAATTAACACATATAAATGA 3'
```

The open reading frame portion of the cDNA (SEQ ID NO: 4) may be amplified using the following primer pair:

primer 3: 5'ATGAATAGAGGGAAAGATGAGGAG 3' (SEQ ID NO: 8)

primer 4: 5'TTAAGGCTTAGAGGAGTCATAGCGT 3' (SEQ ID NO: 9)

These primers are illustrative only; one of ordinary skill in the art will appreciate that many different primers may be derived from the provided cDNA and gene sequences in order to amplify particular regions of these molecules. Resequencing of PCR products obtained by these amplification procedures is recommended; this will facilitate confirmation of the amplified sequence and will also provide information on natural variation in this sequence in different ecotypes and plant populations. Oligonucleotides derived from the Arabidopsis ELF3 sequence may be used in such sequencing methods.

Oligonucleotides that are derived from the Arabidopsis ELF3 cDNA or gene sequences are encompassed within the scope of the present invention. Preferably, such oligonucleotide primers will comprise a sequence of at least 15–20 consecutive nucleotides of the Arabidopsis ELF3 cDNA or gene sequences. To enhance amplification specificity, oligonucleotide primers comprising at least 25, 30, 35, 40, 45 or 50 consecutive nucleotides of these sequences may also be used.

b. ELF3 Genes in Other Plant Species

Orthologs of the ELF3 gene are present in a number of plant species including Chlamydomonas, Douglas fir, corn, broccoli, cauliflower, soybean, Medicago, rice, poplar, tobacco, Cardamine, and tomato (see Examples 4, 5 and 6, below). With the provision herein of the prototypical ELF3 protein from Arabidopsis and cDNA and gene sequences that encode this protein, cloning of cDNAs and genes that encode ELF3 protein orthologs in other plant species is now enabled. Standard methods, including those described herein, can be used. As described above, orthologs of the disclosed Arabidopsis ELF3 protein have ELF3 protein biological activity and typically possess at least 60% sequence identity counted over the full length alignment with the amino acid sequence of Arabidopsis ELF3 using the NCBI Blast 2.0, gapped blastp set to default parameters. Proteins with even greater similarity to the Arabidopsis sequence will show greater percentage identities when assessed by this method, such as at least 70%, at least 75%, at least 80%, at least 90%, at least 91%, at least 92%, at least 93%, at least 94% or at least 95% or more sequence identity.

Both conventional hybridization and PCR amplification procedures may be utilized to clone sequences encoding ELF3 protein orthologs. Common to these techniques is the hybridization of probes or primers derived from the Arabidopsis ELF3 cDNA or gene sequence to a target nucleotide preparation. This target may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the Arabidopsis ELF3 cDNA or gene. One of ordinary skill in the art will appreciate that sequence differences between the Arabidopsis ELF3 cDNA or gene and the target nucleic acid to be amplified may result in lower amplification efficiencies. To compensate for this difference, longer PCR primers or lower annealing temperatures may be used during the amplification cycle. Where lower annealing temperatures are used, sequential rounds of amplification using nested primer pairs may be necessary to enhance amplification specificity.

For conventional hybridization techniques, the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the Arabidopsis cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Orthologs of the Arabidopsis ELF3 may alternatively be obtained by immunoscreening an expression library. With the provision herein of the disclosed Arabidopsis ELF3 nucleic acid sequences, the protein may be expressed in and purified from a heterologous expression system (e.g. *E. coli*) and used to raise antibodies (monoclonal or polyclonal) specific for the Arabidopsis ELF3 protein. Antibodies may also be raised against synthetic peptides derived from the Arabidopsis ELF3 amino acid sequence presented herein. Methods of raising antibodies are well known in the art and are described in Harlow and Lane (1988). Such antibodies can be used to screen an expression cDNA library produced from the plant from which it is desired to clone the ELF3 ortholog, using routine methods. The selected cDNAs can be confirmed by sequencing.

c. ELF3 Sequence Variants

With the provision of the Arabidopsis ELF3 protein and ELF3 cDNA and gene sequences herein, the creation of variants of these sequences is now enabled.

Variant ELF3 proteins include proteins that differ in amino acid sequence from the Arabidopsis ELF3 sequence disclosed but which retain ELF3 protein biological activity. Such proteins may be produced by manipulating the nucleotide sequence of the Arabidopsis ELF3 cDNA or gene using standard procedures, including for instance site-directed mutagenesis or PCR. The simplest modifications involve the substitution of one or more amino acids for amino acids having similar biochemical properties. These so-called conservative substitutions are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |

TABLE 1-continued

| Original Residue | Conservative Substitutions |
| --- | --- |
| Thr | ser |
| Trp | tyr |
| Tyr | trp; phe |
| Val | ile; leu |

More substantial changes in protein functions or other features may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine). The effects of these amino acid substitutions, deletions, or additions may be assessed in ELF3 protein derivatives by analyzing the ability of a gene encoding the derivative protein to complement the photoperiod-insensitive flowering and elongated hypocotyl defects in an elf3 mutant. Alternatively, the effect may be examined by studying circadian influenced CAB-luc transcription and/or leaf movement as discussed in Example 2, below.

Variant ELF3 cDNA or genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the Arabidopsis ELF3 cDNA or gene sequences disclosed, yet which still encode a protein having ELF3 protein biological activity. DNA molecules and nucleotide sequences that are derivatives of those specifically disclosed herein and that differ from those disclosed by the deletion, addition, or substitution of nucleotides while still encoding a protein that has ELF3 protein biological activity are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed Arabidopsis ELF3 protein sequence. For example, the 23rd amino acid residue of the Arabidopsis ELF3 protein is alanine. This alanine residue is encoded for by the nucleotide codon triplet GCA. Because of the degeneracy of the genetic code, three other nucleotide codon triplets—GCT, GCC and GCG—also code for alanine. Thus, the nucleotide sequence of the Arabidopsis ELF3 ORF could be changed at this position to any of these three alternative codons without affecting the amino acid composition or other characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences that encode an ELF3 protein, but which vary from the disclosed nucleic acid sequences by virtue of the degeneracy of the genetic code.

Variants of the ELF3 protein may also be defined in terms of their sequence identity with the prototype ELF3 protein shown in SEQ ID NO: 2. As described above, ELF3 proteins have ELF3 biological activity and share at least 60% sequence identity with the Arabidopsis ELF3 protein. Nucleic acid sequences that encode such proteins may readily be determined simply by applying the genetic code to the amino acid sequence of an ELF3 protein, and such nucleic acid molecules may readily be produced by assembling oligonucleotides corresponding to portions of the sequence.

Nucleic acid molecules that are derived from the Arabidopsis ELF3 cDNA and gene sequences disclosed include molecules that hybridize under stringent conditions to the disclosed prototypical ELF3 nucleic acid molecules, or fragments thereof. Stringent conditions are hybridization at 55° C. in 6× SSC, 5× Denhardt's solution, 0.1% SDS and 100 µg sheared salmon testes DNA, followed by 15–30 minute sequential washes at 55° C. in 2× SSC, 0.1% SDS, followed by 1× SSC, 0.1% SDS and finally 0.2× SSC, 0.1% SDS.

Low stringency hybridization conditions (to detect less closely related homologs) are performed as described above but at 50° C. (both hybridization and wash conditions); however, depending on the strength of the detected signal, the wash steps may be terminated after the first 2 x SSC, 0.1% SDS wash.

The Arabidopsis ELF3 gene or cDNA, and orthologs of these sequences from other plants, may be incorporated into transformation vectors and introduced into plants to produce plants with an altered photoperiodic or circadian rhythm phenotype, as described below.

III. Introducing ELF3 into Plants

Once a nucleic acid molecule (e.g., cDNA or gene) encoding a protein involved in the determination of a particular plant characteristic has been isolated, standard techniques may be used to express the cDNA in transgenic plants in order to modify that particular plant characteristic. The basic approach is to clone, for instance, the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector that integrates into the plant cell and that contains the introduced cDNA and associated sequences for controlling expression (the introduced "transgene") may be referred to as the recombinant expression cassette.

Selection of progeny plants containing the introduced transgene may be based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology, include:

U.S. Pat. No. 5,451,514 (modification of lignin synthesis using antisense RNA and co-suppression);

U.S. Pat. No. 5,750,385 (modification of plant light-, seed- and fruit-specific gene expression using sense and antisense transformation constructs);

U.S. Pat. No. 5,583,021 (modification of virus resistance by expression of plus-sense untranslatable RNA);

U.S. Pat. No. 5,589,615 (production of transgenic plants with increased nutritional value via the expression of modified 2S storage albumins);

U.S. Pat. No. 5,268,526 (modification of phytochrome expression in transgenic plants);

U.S. Pat. No. 5,741,684 (production of plants resistant to herbicides or antibiotics through the use of anti-sense expression);

U.S. Pat. No. 5,773,692 (modification of the levels of chlorophyll by transformation of plants with anti-sense messages corresponding to chlorophyll a/b binding protein);

WO 96/13582 (modification of seed VLCFA composition using over expression, co-suppression and antisense RNA in conjunction with the Arabidopsis FAE1 gene)

These examples include descriptions of transformation vector selection, transformation techniques and the assembly of constructs designed to over-express the introduced nucleic acid, as well as techniques for sense suppression and anti-sense expression. In light of the foregoing and the provision herein of the Arabidopsis ELF3 cDNA and gene sequences, one of ordinary skill in the art will be able to introduce these nucleic acid molecules, or orthologous, homologous or derivative forms of these molecules, into plants in order to produce plants having altered ELF3 activity. Manipulating the expression of ELF3 in plants will be useful to confer altered circadian clock and/or photoperiodism function. Alteration of the ELF3 protein levels in plants could be used to re-set or customize the circadian clock, for instance in order to alter the plant developmental patterns or photoperiodic responses (e.g., the timing of floral development).

a. Plant Types

The presence of a circadian cycle appears to be universal, occurring not only in all plants thus far examined, but also in insects, including Drosophila (Hall, 1990) and microbes such as *Neurospora crassa* (Dunlap, 1993). At the molecular level, ELF3 homologs have been found in a variety of plant species (see Example 4, below). Thus, expression of the ELF3 protein may be modified in a wide range of higher plants to confer altered circadian clock and/or photoperiodism function, including monocotyledonous and dicotyledenous plants. These include, but are not limited to, Arabidopsis, Cardamine, cotton, tobacco, maize, wheat, rice, barley, soybean, beans in general, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; other trees including poplar, oak, maple, pine, spruce and other conifers; and flowers or other ornamental plants such as carnations, roses, petunias, orchids, impatiens, pansies, lilies, snapdragons, geraniums, and so forth.

b. Vector Construction, Choice of Promoters

A number of recombinant vectors suitable for stable transformation of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences, and at least one dominant selectable marker. Such plant transformation vectors typically also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing an ELF3 nucleic acid molecule include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters are regulated in response to environmental, hormonal, chemical, and/or developmental signals, and can be used for expression of the cDNA in plant cells. Such promoters include, for instance, those regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wun1, Siebertz et al., 1989); and (e) chemicals such as methyl jasminate or salicylic acid (see also Gatz et al., 1997).

Alternatively, tissue specific (root, leaf, flower, or seed, for example) promoters (Carpenter et al 1992, Denis et al. 1993, Opperman et al. 1993, Stockhause et al. 1997; Roshal et al., 1987; Schernthaner et al., 1988; and Bustos et al., 1989) can be fused to the coding sequence to obtained protein expression in specific organs.

Promoters responsive to the circadian cycle can also be used in plant gene expression vectors. Such promoters include the native ELF3 promoter as described herein, and the promoter from the chlorophyll a/b binding protein (Millar et al. 1992).

Plant transformation vectors may also include RNA processing signals, for example, introns, which may be positioned upstream or downstream of the ORF sequence in the transgene. In addition, the expression vectors may include further regulatory sequences from the 3'-untranslated region of plant genes, e.g., a 3' terminator region to increase mRNA stability of the mRNA, such as the PI-11 terminator region of potato or the Agrobacterium octopine or nopaline synthase 3' terminator regions. The 3' region of the ELF3 gene can also be used.

Finally, as noted above, plant transformation vectors may include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g. phosphinothricin acetyltransferase).

c. Arrangement of ELF3 Sequence in the Vector

The particular arrangement of the ELF3 sequence in the transformation vector will be selected according to the type of expression of the sequence that is desired.

Where enhanced ELF3 protein activity is desired in the plant, an ELF3 ORF may be operably linked to a constitutive high-level promoter such as the CaMV 35S promoter. As noted below, modification of ELF3 synthesis may also be achieved by introducing into a plant a transformation vector containing a variant form of an ELF3 cDNA or gene.

In contrast, a reduction of ELF3 activity in the transgenic plant may be obtained by introducing into plants an anti-sense construct based on an ELF3 cDNA or gene sequence. For antisense suppression, an ELF3 cDNA or gene is arranged in reverse orientation relative to the promoter sequence in the transformation vector. The introduced sequence need not be a full length ELF3 cDNA or gene, and need not be exactly homologous to the native ELF3 cDNA or gene found in the plant type to be transformed. Generally, however, where the introduced sequence is of shorter length, a higher degree of homology to the native ELF3 sequence will be needed for effective antisense suppression. The introduced antisense sequence in the vector generally will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous ELF3 gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA. The production and use of antisense constructs are disclosed, for instance, in U.S. Pat. No. 5,773,692 (using constructs encoding anti-sense RNA for chlorophyll a/b binding protein to reduce plant chlorophyll content), and U.S. Pat. No. 5,741,684 (regulating the fertility of pollen in various plants through the use of anti-sense RNA to genes involved in pollen development or function).

Suppression of endogenous ELF3 gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. Inclusion of ribozyme sequences within antisense RNAs may be used to confer RNA cleaving activity on the antisense RNA, such that endogenous mRNA molecules that bind to the antisense RNA are cleaved, leading to an enhanced antisense inhibition of endogenous gene expression.

Constructs in which an ELF3 cDNA or gene (or variants thereof) are over-expressed may also be used to obtain co-suppression of the endogenous ELF3 gene in the manner described in U.S. Pat. No. 5,231,021 to Jorgensen. Such co-suppression (also termed sense suppression) does not require that the entire ELF3 cDNA or gene be introduced into the plant cells, nor does it require that the introduced sequence be exactly identical to the endogenous ELF3 gene. However, as with antisense suppression, the suppressive efficiency will be enhanced as (1) the introduced sequence is lengthened and (2) the sequence similarity between the introduced sequence and the endogenous ELF3 gene is increased.

Constructs expressing an untranslatable form of an ELF3 mRNA may also be used to suppress the expression of endogenous ELF3 activity. Methods for producing such constructs are described in U.S. Pat. No. 5,583,021 to Dougherty et al. Preferably, such constructs are made by introducing a premature stop codon into an ELF3 ORF.

Finally, dominant negative mutant forms of the disclosed sequences may be used to block endogenous ELF3 activity. Such mutants require the production of mutated forms of the ELF3 protein that interact with the same molecules as ELF3 but do not have ELF3 activity.

d. Transformation and Regeneration Techniques

Transformation and regeneration of both monocotyledonous and dicotyledonous plant cells is now routine, and the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether the circadian cycle or photoperiodism of the transformed plant has been altered as a result of the introduced transgene.

IV. Production of Recombinant ELF3 Protein in Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (1989). Such systems may be used to express ELF3 at high levels to facilitate purification of the protein. The purified ELF3 protein may be used for a variety of purposes. For example, the purified recombinant enzyme may be used as an immunogen to raise anti-ELF3 antibodies. Such antibodies are useful as both research reagents (such as in the study of circadian clock and photoperiodism mechanisms in plants) as well as diagnostically to determine expression levels of the protein in plants that are being developed for agricultural or other use. Thus, the antibodies may be used to quantify the level of ELF3 protein both in non-transgenic plant varieties and in transgenic varieties that are designed to over-express or under-express the ELF3 protein. Such quantification may be performed using standard immunoassay techniques, such as ELISA and in situ immunofluorescence and others described in Harlow & Lane (1988).

By way of example only, high level expression of the ELF3 protein may be achieved by cloning and expressing the ELF3 cDNA in yeast cells using the pYES2 yeast expression vector (INVITROGEN, Carlsbad, Calif.). Alternatively, a genetic construct may be produced to direct secretion of the recombinant ELF3 protein from yeast cells into the growth medium. This approach will facilitate the purification of the ELF3 protein, if this is necessary. Secretion of the recombinant protein from the yeast cells may be achieved by placing a yeast signal sequence adjacent to the ELF3 coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

Alternatively, the enzyme may be expressed at high level in prokaryotic expression systems, such as *E. coli*, as described in Sambrook et al. (1989). Commercially available prokaryotic expression systems include the pBAD expression system and the ThioFusion expression system (INVITROGEN, Carlsbad, Calif.).

V. ELF3 Promoter

The 5' regulatory region of the ELF3 gene is also provided herein (SEQ ID NO: 5). This regulatory region confers ELF3-like circadian rhythm-based expression on open reading frames to which it is operably linked. Approximately 4 kb of the ELF3 5' regulatory region is provided in SEQ ID NO: 5. While this entire ca. 4 kb regulatory sequence may be employed, one of ordinary skill in the art will appreciate that less than this entire sequence may be sufficient to confer ELF3-like circadian rhythm expression. For example, sequences comprising nucleotides 1–4071 of SEQ ID NO: 5 or shorter sequences such as those spanning nucleotides 500–4071, 1000–4071, 1500–4071, 2000–4071, 2500–4071, 3000–4071, 3500–4071 and 4000–4071 may be employed. One embodiment of an ELF3 promoter is about nucleotides 1 through about 1900 of the 5' upstream region shown in SEQ ID NO: 5. Other particular embodiments include about nucleotides 50–1900, 150–1900, 250–1900, 350–1900, 450–1900, 550–1900 and so forth.

Sequences as short as 50 or 100 nucleotides from within the 5' regulatory region of ELF3 may also be employed. The determination of whether a particular sub-region of the disclosed sequence operates to confer effective ELF3-like circadian rhythm expression in a particular system (taking into account the plant species into which the construct is being introduced, the level of expression required, etc.) will be performed using known methods. These include, for instance, operably linking the promoter sub-region to a marker gene (e.g. GUS or luciferase), introducing such constructs into plants, and determining the level of expression of the marker gene.

The present invention therefore facilitates the production, by standard molecular biology techniques, of nucleic acid molecules comprising this promoter sequence operably linked to a nucleic acid sequence, such as an open reading frame. Suitable open reading frames include open reading frames encoding any protein for which ELF3-like circadian rhythm expression is desired.

EXAMPLES

Example 1

Cloning Arabidopsis ELF3

The ELF3 gene was isolated by map-based positional cloning. Molecular markers tightly linked to the ELF3 gene were identified by random fragment length polymorphism (RFLP) analysis, and a high resolution genetic map of the locus was constructed. The region containing the ELF3 gene was narrowed down to 30 kb contained on a single bacterial artificial chromosome (BAC). This BAC was sequenced, and cDNAs with homology to sequences within the BAC were isolated from a variety of cDNA libraries. The ELF3 sequence was further localized by complementation experiments to a 10 kb subcloned fragment contained within the BAC. Identification of the appropriate gene within the subcloned fragment was confirmed through isolation and sequencing of elf 3 alleles from various Arabidopsis elf3 mutants.

The isolated ELF3 gene (SEQ ID NO: 3) has no significant sequence similarity to other DNA or protein sequences with assigned function. However, a published EST (GenBank # N96569; Newman et al., 1994) overlaps nucleotide 1235–2501 of the corresponding cDNA (SEQ ID NO: 1). ELF3 has four exons, and is transcribed as an mRNA of about 2.4 kb in Arabidopsis 35 seedlings and in mature leaves. The putative protein (SEQ ID NO: 2) encoded by the ELF3 ORF (SEQ ID NO: 4) is 695 amino acids in length and has a predicted molecular weight of approximately 80 KDa.

Research by this group has recently identified several putative ELF3 orthologs from other plant species, including *Cardamine oligosperma*, tomato, rice, and maize (see Examples 4 and 5, below). GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [*Lycopersicon esculentum* Expressed Sequence Tags (ESTs) from Clemson University Genomics Institute: AW093790 (October 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

Example 2

Analysis of ELF3 Phenotype

Sensitive assays for monitoring circadian rhythm responses in Arabidopsis have been developed (Millar and Kay, 1991; Millar et al., 1992). One assay system is based on the observation that the transcription of the chlorophyll a/b binding protein gene, CAB2, cycles on a 24-hour period. Transcription from the CAB2 promoter increases prior to subjective dawn, peaks in late morning, and falls to a low level late in the day (Millar and Kay, 1991). Cycling of CAB mRNA continues under constant light conditions. In order to follow expression in vivo, the CAB2 promoter has been fused to the gene encoding firefly luciferase (luc), and this fusion has been transformed in wild-type Arabidopsis (Millar et al., 1992). Transcriptional expression from the CAB2-luc fusion construct is monitored by imaging single transgenic seedlings using a low-light video camera and a photon-counting image processor; the results from imaging the CAB2-luc fusion is comparable to the transcriptional expression of the endogenous CAB2 gene. With this system, over one hundred individual seedlings can be imaged every 30 minutes, thus allowing the collection of thousands of data points in less than one week. This very powerful system has recently been used to characterize several known photomorphogenic Arabidopsis mutants (Millar et al., 1995a) and to isolate a short-period mutant of Arabidopsis (Millar et al., 1995b). Elf3 mutants examined using this system are defective in circadian regulated CAB2 transcription (Hicks et al., 1996).

An automatic video imaging system can also be used to monitor a second circadian regulated process, leaf movement (Millar and Kay, 1991). Plant leaves turn down (open) during the day and turn up (closed) during the night in a circadian fashion. Arabidopsis seedlings display this circadian leaf movement in constant light, and this can be assayed and quantified using a relatively inexpensive video and computer system (Millar and Kay, 1991). The analysis of leaf movements provides an independent circadian regulated process with which to evaluate potential circadian rhythm mutants (see, for instance, Schaffer et al. 1998, using leaf movement to analyze circadian cycle disruption in late elongated hypocotyl (Ihy) mutants in Arabidopsis). Elf3 mutants are also defective in circadian regulated leaf movements.

These assays may be used to assess the effect that modifying ELF3 protein expression level (e.g., through introduction of ELF3 antisense or sense constructs into plants) has on plant phenotype.

Example 3

Introducing ELF3 Sequences into Plants Plasmid Construction

Arabidopsis ELF3 cDNA (SEQ ID NO: 1) and full-length genomic (SEQ ID NO: 3) sequences were used in the construction of over-expression and antisense vectors. These sequences were operably linked to the CaMV 35S (constitutive) promoter, in both the sense and antisense orientations, and cloned using standard molecular biology techniques into pSJL4 (Jones et al. 1992).

The over-expression and antisense expression cassettes were removed from the above vectors and inserted into pMON505 for Agrobacterium-mediated plant transformation.

Plant Transformation

Wild-type and elf3 mutant Arabidopsis plants (ecotype Columbia) were transformed using standard in planta Agrobacterium-mediated techniques (Chang et al. 1994, Katavic et al. 1994). Transformed seeds were selected on kanamycin, and Kan$^R$ seedlings transferred to soil and grown for further analysis.

Over-expression of ELF3 protein in elf3 mutant plants comprising the ELF3 genomic gene sequence as the transgene resulted in full complementation of the elf3 mutant phenotype in some transformed plants. In some instances, over-expression of ELF3 protein from cDNA-based transgenes in wild-type plants produced elf3 mutant-like plants or plants having intermediate phenotype; this is probably the result of co-suppression. Antisense expression of the full-length ELF3 cDNA in wild-type plants produced some transformants with an elf3 mutant-like phenotype.

Example 4

ELF3 Orthologs

As noted above, orthologs of ELF3 exist in a number of plant species including corn, tomato and tobacco. The existence of these sequences may be demonstrated by hybridization techniques, such as Southern blotting. Hybridization was performed using a probe based on the entire ELF3 cDNA sequence (SEQ ID NO: 1). This probe was hybridized to genomic DNA from Arabidopsis, Chlamydomonas, Douglas fir, corn, rice, poplar, tobacco, and tomato. High stringency hybridization was performed at 55° C. in 6× SSC, 5× Denhardt's solution, 0.1% SDS and 100 µg sheared salmon testes DNA, followed by 15–30 minute sequential washes at 55° C. in 2× SSC, 0.1% SDS, followed by 1× SSC, 0.1% SDS and finally 0.2× SSC, 0.1% SDS. A single, clean hybridizing band was observed on the Southern blot in Arabidopsis, rice, and tobacco genomic DNA preparations.

Lower stringency hybridization conditions were used to detect less closely related ELF3 homologs. Such hybridization was performed at 50° C. for 24 hours in the hybridization solution described above, followed by washing in 2× SSC, 0.1% SDS at 500 C for 3 hours, with five sequential changes of wash solution. Hybridization of full length cDNA probe under low stringency hybridization conditions detected ELF3 homologs (indicated by one or more bands on the Southern) in Arabidopsis, Chlamydomonas, Douglas fir, corn, rice, poplar, tobacco, and tomato and other plant species.

Once an ELF3-hybridizing band is detected in a plant species, standard techniques such as screening cDNA or genomic libraries from the plant with the ELF3 probe may be used. Alternatively, ELF3 homologs may be isolated by screening an expression library from the plant in question using a ELF3 protein specific binding agent, such as an anti-ELF3 antibody produced as described above. Such homologs may be introduced into plants using the methods described above in order to produce altered circadian rhythm and/or photoperiodic phenotypes.

It is also possible to use primers complementary to the Arabidopsis ELF3 sequence to amplify orthologous nucleic acid sequences. For example, an ELF3 ortholog has been isolated in this manner from a Cardamine genomic DNA preparation, using the following PCR amplification primers:

```
                                                (SEQ ID NO:10)
primer 5: 5'ATGAAGAGAGGGAAAGATGAGG 3'

(SEQ ID NO:11)
primer 6: 5'GCCACCATCTCGGTATAACC 3'.
```

Degenerate mixtures of oligonucleotides may also be used to amplify orthologous nucleic acid sequences. The construction of degenerate oligonucleotides is well known to one of ordinary skill in the art.

Nucleotide sequences from C. oligosperma (a member of the family Brassicaceae) were obtained by sequencing polymerase chain reaction products using degenerate oligonucleotides to the Arabidopsis ELF3 gene and genomic DNA or cDNA prepared from C oligosperma seedlings using standard techniques. The sequence of the amplified Cardamine ELF3 ortholog (cELF3) is shown in SEQ ID NO: 12.

Example 5

Consensus Sequences Within the ELF3 Protein and Homologs Thereof

Computerized, searchable databases were searched for sequences having significant homology the Arabidopsis ELF3 cDNA and genomic nucleotide sequences depicted herein, and the Cardamine ELF3 ortholog nucleotide sequence (SEQ ID NO: 12).

This search yielded several putative ELF3 homologs. GenBank accession numbers for ELF3 and the putative ELF3 homologs identified as such by this research group are as follows: AtELF3 (*A. thaliana* genomic DNA: AC004747), AtEEC (*A. thaliana* genomic DNA: AB023045), cELF3 (yet to be submitted), tELF3 (*Lycopersicon esculentum* Expressed Sequence Tags (ESTs) from Clemson University Genomics Institute: AW093790, AI894513, AI488927, AI486934, AI894398), rELF3 (*Oryza sativa* genomic DNA: AP000399), and mELF3 (*Zea mays* EST from Stanford University Genome Center: AI637184).

Multiple sequence alignment of the ELF3 proteins (FIGS. 1 and 2) shows four highly conserved regions within ELF3 and putative ELF3 homologs from *Arabidopsis thaliana* (Essence of ELF3 Consensus, EEC) and other plant species (*Cardamine oligosperma*, tomato, rice, and maize) (FIG. 2). Sequences were aligned and analyzed using CLUSTAL W (Thompson et al., *Nucleic Acids Res.* 22, 4673–80, 1994) and PrettyBox (Genetics Computer Group, Inc.). Protein designations are given on the left. Amino acid residues are numbered on both the left and right. Residues shaded in black indicate identity of at least three ELF3/ELF3-related sequences in the alignment; light-shaded residues indicate similarity to consensus.

Example 6

Additional ELF3 Orthologs

The ELF3 sequences and consensus sequences isolated as described above were used additional similar sequences from other plant species, using nucleic acid amplification and/or computer database searches. Additional ELF3 orthologs have been identified in *Medicago trunculata* (SEQ ID NOs: 36–39), *Pisum sativa* (SEQ ID NOs: 40–43), *Glycine max* (SEQ ID NOs: 44- and 45),Xanthium (SEQ ID NOs: 46–51), Poplar (SEQ ID NOs: 52–53), Mimulus (SEQ ID NOs: 54 and 55), *Zea mays* (SEQ ID NOs: 56 and 57), *Lycopersicon esculentum* (SEQ ID NOs: 58 and 59), and Broccoli (SEQ ID NOs: 60–63). Nucleic acid amplification, particularly polymerase chain amplification (PCR) also was used to confirm several of these sequences. For isolation and/or confirmation, amplification reactions were annealed at 55° C. and extended for 35 seconds per round. The primers used were as follows:

| Amplified ortholog | Forward primer | Reverse primer |
| --- | --- | --- |
| *Pisum sativa* (SEQ ID NO: 40) | B-FWD, SEQ ID NO: 66 | C-REV, SEQ ID NO: 68 |
| *Pisum sativa* (SEQ ID NO: 42) first round | Pea1b-C-FWD, SEQ ID NO: 67 | D-REV, SEQ ID NO: 65 |
| *Pisum sativa* (SEQ ID NO: 42) second round | C-FWD, SEQ ID NO: 64 | D-REV, SEQ ID NO: 65 |
| Xanthia (SEQ ID NO: 46) | B-FWD, SEQ ID NO: 66 | C-REV, SEQ ID NO: 68 |
| Xanthia (SEQ ID NO: 48) | B-FWD, SEQ ID NO: 66 | C-REV, SEQ ID NO: 68 |
| Xanthia (SEQ ID NO: 50) | C-FWD, SEQ ID NO: 64 | D-REV, SEQ ID NO: 65 |
| Poplar (SEQ ID NO: 52) | C-FWD, SEQ ID NO: 64 | D-REV, SEQ ID NO: 65 |
| Mimulus (SEQ ID NO: 54) | C-FWD, SEQ ID NO: 64 | D-REV, SEQ ID NO: 65 |
| *Zea mays* (SEQ ID NO: 56) | B-FWD, SEQ ID NO: 66 | C-REV, SEQ ID NO: 68 |
| *Zea mays* (SEQ ID NO: 56) | C-FWD, SEQ ID NO: 64 | D-REV, SEQ ID NO: 65 |
| Broccoli (SEQ ID NO: 62) | C-FWD, SEQ ID NO: 64 | D-REV, SEQ ID NO: 65 |

The amplified products were of the expected sizes.

The foregoing examples are provided by way of illustration only. One of skill in the art will appreciate that numerous variations on the biological molecules and methods described above may be employed to make and use the ELF3 gene, corresponding protein, and promoter region. We claim all such subject matter that falls within the scope and spirit of the following claims.

REFERENCES

Ainley et al. (1993) *Plant Mol. Biol.* 22:13–23.
Altschul et al. (1990). *J Mol. Biol.*, 215, 403–10
Altschul et al. (1994). *Nature Genet.*, 6, 119–29.
An et al. (1988) *Plant Physiol.* 88:547.
Aronson et al. (1994) *Science* 263:1578–1584.
Ausubel et al. (1987) In *Current Protocols in Molecular Biology*, Greene Publishing Associates and Wiley-Intersciences.
Benfey and Chua (1990) *Science* 250:959–966.
Bernier (1988) *Ann. Rev. Plant Phys. and Plant Mol. Bio.* 39:175–219.
Bustos et al. (1989) *Plant Cell* 1:839.
Callis et al. (1988) *Plant Physiol.* 88:965.
Carpenter et al. (1992) *The Plant Cell* 4:557–571.
Chang et al. (1994) *Plant J.* 5:551–558.
Chang et al. (1986) *Mol. And Cell. Biol.* 6:1812–1819.
Corpet et al. (1988). *Nucleic Acids Research* 16, 10881–90.
Dekeyser et al. (1990) *Plant Cell* 2:591.
Denis et al. (1993) *Plant Physiol.* 101:1295–1304.
Dunlap (1993) *Annu. Rev. Physiol* 55:683.
Edery et al. (1994) *Science* 263:237–240.
Fromm et al. (1989) *Plant Cell* 1:977.
Gatz et al. (1997) *Ann. Rev. Plant Physiol. Plant Mol. Biol.* 48:89–108.
Gelvin et al. (1990) *Plant Molecular Biology Manual*, Kluwer Academic Publishers.
Gilmartin et al. (1992) *The Plant Cell* 4:839–949.
Hall (1990) *Ann. Rev. Genet.* 24:659.
Harlow & Lane (1988) *Antibodies, A Laboratory Manual*, Cold Spring Harbor Laboratory, New York.
Hicks et al. (1996) *Science* 274(5288):790–792.
Higgins and Sharp (1988). *Gene*, 73: 237–244.
Higgins and Sharp (1989). *CABIOS* 5:151–153.
Huang et al. (1992). *Computer Applications in the Biosciences* 8, 155–65.
Hülskamp et al. (1990) *Nature* 346:577–580.
Innis et al. (eds.) (1990) *PCR Protocols, A Guide to Methods and Applications, Academic Press, Inc., San Diego, Calif.*
Jones et al. (1992) *Transgenic Res.* 1:285–297.
Katavic et al. (1994) *Mol. Gen. Genet.* 245:363–370.
Koornneef et al. (1991) *Mol. Gen. Genet.* 229:57–66.
Kuhlemeier et al. (1989) *Plant Cell* 1: 471.
Lambie and Kimble (1991) *Development* 112:231–240.
Liang & Richardson (1993) *J. Agric. Food Chem.* 41:1800–1807.
Marcotte et al. (1989) *Plant Cell* 1:969.
Millar et al. (1995a) *Science* 267(5201): 1163–1166.
Millar et al. (1995b) *Science* 267(5201): 1161–1163.
Millar et al. (1992) *Plant Cell* 4:1075–1087.
Millar and Kay (1991) *Plant Cell* 3:541–550.
Mozo et al. (1998) *Mo. Gen. Genet.* 258(5):562–570.
Murfet (1985) *Pisum sativum*. In *Handbook of Flowering Plants* Vol. IV, ed. A.H. Halevy. (CRC Press: Boca Raton, Fla.), pp. 97–126.
Needleman and Wunsch (1970). *J. Mol. Biol.* 48: 443.
Newman et al. (1994) *Plant Physiol.* 106(4): 1241–1255.
Odel et al. (1985) *Nature* 313:810.
Opperman et al. (1993) *Science* 263:221–223.
Pearson and Lipman (1988). *Proc. Natl. Acad. Sci. USA* 85: 2444.
Pearson et al. (1994). *Methods in Molecular Biology* 24, 307–31.
Pouwels et al. (1987) *Cloning Vectors: A Laboratory Manual*, 1985, supp.
Roshal et al. (1987) *EMBO J.* 6:1155.
Sambrook et al. (1989) In *Molecular Cloning: A Laboratory Manual*, Cold Spring Harbor, N.Y.
Schaffer et al. (1998) *Cell* 93:1219–1229.
Schaffner & Sheen (1991) *Plant Cell* 3:997.

Schernthaner et al. (1988) *EMBO J.* 7:1249.
Shannon and Meeks-Wagner (1991) *Plant Cell* 3:877–892.
Siebertz et al. (1989) *Plant Cell* 1:961.
Smith et al. (1985) *Science* 229:1219–1224.
Smith and Waterman (1981). *Adv. Appl. Math.* 2: 482.
Stockhause et al. (1997) *The Plant Cell* 9:479–489.
Terada & Shimamoto (1990) *Mol. Gen. Genet.* 220:389.
Tijssen (1993). *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.
Wang & Tobin (1998) *Cell* 93:1207–1217.
Weissbach & Weissbach (1989) *Methods for Plant Molecular Biology*, Academic Press.
Zagotta et al. (1992) *Aust. J. Plant Physiol.* 19:411–418.
Zagotta et al. (1996) *Plant J.* 10(4):691–702.

We claim:

1. An isolated nucleic acid molecule encoding a protein comprising the amino acid sequence shown in SEQ ID NO: 2.

2. The nucleic acid molecule according to claim 1, wherein the nucleic acid molecule comprises a nucleotide sequence selected from the group consisting of:
   (a) SEQ ID NO: 1;
   (b) SEQ ID NO: 3; and
   (c) SEQ ID NO: 4.

3. A recombinant nucleic acid molecule comprising a promoter sequence operably linked to the nucleic acid molecule according to claim 1.

4. A host cell transformed with the recombinant nucleic acid molecule according to claim 3.

5. The cell of claim 4, wherein the cell is a plant cell or a bacterial cell.

6. A transgenic plant comprising the recombinant nucleic acid molecule according to claim 3.

7. The transgenic plant according to claim 6, wherein the plant is selected from the group consisting of Arabidopsis, Cardamine, Medicago, Mimulus, Xanthium, pepper, tomato, carrot, tobacco, broccoli, cauliflower, cabbage, canola, bean, pea, soybean, rice, corn, wheat barley, flax, citrus, cotton, cassava, walnut, and conifer.

8. The transgenic plant of claim 6, wherein the plant is selected from the group consisting of flowers, petunias, orchids, carnations, roses, impatiens, pansies, lilies, snapdragons, and geraniums.

9. A method of modifying the level of expression of an ELF3 protein in a plant, wherein the method comprises expressing in the plant a recombinant genetic construct comprising a promoter operably linked to a nucleic acid molecule, wherein the nucleic acid molecule comprises the sequence as set forth in SEQ ID NO: 1, 3, or 4.

10. The method of claim 9, wherein the nucleic acid molecule is in antisense orientation relative to the promoter.

* * * * *

UNITED STATES PATENT AND TRADEMARK OFFICE
CERTIFICATE OF CORRECTION

PATENT NO. : 6,689,940 B2  Page 1 of 1
APPLICATION NO. : 09/746801
DATED : February 10, 2004
INVENTOR(S) : Wagner et al.

It is certified that error appears in the above-identified patent and that said Letters Patent is hereby corrected as shown below:

<u>In the Specification, insert at Column 1, line 15</u>:

--ACKNOWLEDGMENT OF GOVERNMENT SUPPORT

This invention was made with government support under Grant No. MCB9507218 awarded by the National Science Foundation. The government has certain rights in the invention.--

Signed and Sealed this

Fourth Day of December, 2007

JON W. DUDAS
*Director of the United States Patent and Trademark Office*

SEQUENCE LISTING

<160> NUMBER OF SEQ ID NOS: 68

<210> SEQ ID NO 1
<211> LENGTH: 2518
<212> TYPE: DNA
<213> ORGANISM: Arabidopsis thaliana
<220> FEATURE:
<221> NAME/KEY: CDS
<222> LOCATION: (284)..(2371)
<223> OTHER INFORMATION:

<400> SEQUENCE: 1

```
                tgaaaactca ctttggtttt gtttgattcc tctttagtct gttttcgat ttcgttttct    60
                ctgattggtt tggtggtgag atctctatcg tagtttgtcc tttgggttaa gatatttcat   120
                ttgattggtg ggtttgtttt attgaagctt attgttgtga aagttggagt ctttctcagt   180
                ttttaggttg aattattaag agaaagggaa gatttttggt gtgaagttag gttatttggg   240
                gtttgagaag tttgcaagtg aaaaaggttg tgaattgtga gtg atg aag aga ggg       295
                                                            Met Lys Arg Gly
                                                              1
    aaa gat gag gag aag ata ttg gaa cct atg ttt cct cgg ctt cat gtg          343
    Lys Asp Glu Glu Lys Ile Leu Glu Pro Met Phe Pro Arg Leu His Val
      5                  10                  15                  20
    aat gat gca gat aaa gga ggg cct aga gct cct cct aga aac aag atg          391
    Asn Asp Ala Asp Lys Gly Gly Pro Arg Ala Pro Pro Arg Asn Lys Met
                     25                  30                  35
    gct ctt tat gag cag ctt agt att cct tct cag agg ttt ggt gat cat          439
    Ala Leu Tyr Glu Gln Leu Ser Ile Pro Ser Gln Arg Phe Gly Asp His
                 40                  45                  50
    gga acg atg aat tct cgt agt aac aac aca agc act ttg gtt cat cct          487
    Gly Thr Met Asn Ser Arg Ser Asn Asn Thr Ser Thr Leu Val His Pro
             55                  60                  65
    gga cca tct agt cag cct tgt ggt gtg gaa aga aac tta tct gtc cag          535
    Gly Pro Ser Ser Gln Pro Cys Gly Val Glu Arg Asn Leu Ser Val Gln
     70                  75                  80
    cat ctt gat tct tca gcc gca aac caa gca act gag aag ttt gtc tcc          583
    His Leu Asp Ser Ser Ala Ala Asn Gln Ala Thr Glu Lys Phe Val Ser
     85                  90                  95                 100
    caa atg tcc ttc atg gaa aat gtg aga tct tcg gca cag cat gat cag          631
    Gln Met Ser Phe Met Glu Asn Val Arg Ser Ser Ala Gln His Asp Gln
                105                 110                 115
    agg aaa atg gtg aga gag gaa gaa gat ttt gca gtt cca gta tat att          679
    Arg Lys Met Val Arg Glu Glu Glu Asp Phe Ala Val Pro Val Tyr Ile
            120                 125                 130
    aac tca aga aga tct cag tct cat ggc aga acc aag agt ggt att gag          727
    Asn Ser Arg Arg Ser Gln Ser His Gly Arg Thr Lys Ser Gly Ile Glu
        135                 140                 145
    aag gaa aaa cac acc cca atg gtg gca cct agc tct cat cac tcc att          775
    Lys Glu Lys His Thr Pro Met Val Ala Pro Ser Ser His His Ser Ile
    150                 155                 160
    cga ttt caa gaa gtg aat cag aca ggc tca aag caa aac gta tgt ttg          823
    Arg Phe Gln Glu Val Asn Gln Thr Gly Ser Lys Gln Asn Val Cys Leu
    165                 170                 175                 180
    gct act tgt tca aaa cct gaa gtt agg gat cag gtc aag gcg aat gca          871
    Ala Thr Cys Ser Lys Pro Glu Val Arg Asp Gln Val Lys Ala Asn Ala
                185                 190                 195
    agg tca ggt ggc ttt gta atc tct tta gat gta tca gtc aca gag gag          919
    Arg Ser Gly Gly Phe Val Ile Ser Leu Asp Val Ser Val Thr Glu Glu
            200                 205                 210
    att gat ctc gaa aaa tca gca tca agt cat gat aga gta aat gat tat          967
    Ile Asp Leu Glu Lys Ser Ala Ser Ser His Asp Arg Val Asn Asp Tyr
        215                 220                 225
    aat gct tcc ttg aga caa gag tct aga aat cgg tta tac cga gat ggt         1015
    Asn Ala Ser Leu Arg Gln Glu Ser Arg Asn Arg Leu Tyr Arg Asp Gly
```

```
                    230                 235                 240
ggc aaa act cgt ctg aag gac act gat aat gga gct gaa tct cac ttg    1063
Gly Lys Thr Arg Leu Lys Asp Thr Asp Asn Gly Ala Glu Ser His Leu
245                 250                 255                 260
gca acg gaa aat cat tca caa gag ggt cat ggc agt cct gaa gac att    1111
Ala Thr Glu Asn His Ser Gln Glu Gly His Gly Ser Pro Glu Asp Ile
                265                 270                 275
gat aat gat cgt gaa tac agc aaa agc aga gca tgc gcc tct ctg cag    1159
Asp Asn Asp Arg Glu Tyr Ser Lys Ser Arg Ala Cys Ala Ser Leu Gln
            280                 285                 290
cag ata aat gaa gag gca agt gat gac gtt tct gat gat tcg atg gtg    1207
Gln Ile Asn Glu Glu Ala Ser Asp Asp Val Ser Asp Asp Ser Met Val
        295                 300                 305
gat tct ata tcc agc ata gat gtc tct ccc gat gat gtt gtg ggt ata    1255
Asp Ser Ile Ser Ser Ile Asp Val Ser Pro Asp Asp Val Val Gly Ile
    310                 315                 320
tta ggt caa aaa cgt ttc tgg aga gca agg aaa gcc att gcc aat caa    1303
Leu Gly Gln Lys Arg Phe Trp Arg Ala Arg Lys Ala Ile Ala Asn Gln
325                 330                 335                 340
caa aga gta ttt gct gtt caa cta ttt gag ttg cac aga ctg att aag    1351
Gln Arg Val Phe Ala Val Gln Leu Phe Glu Leu His Arg Leu Ile Lys
                345                 350                 355
gtt caa aaa ctt att gct gca tca ccg gat ctc ttg ctc gat gag atc    1399
Val Gln Lys Leu Ile Ala Ala Ser Pro Asp Leu Leu Leu Asp Glu Ile
            360                 365                 370
agt ttt ctt gga aaa gtt tct gct aaa agc tat cca gtg aag aag ctc    1447
Ser Phe Leu Gly Lys Val Ser Ala Lys Ser Tyr Pro Val Lys Lys Leu
        375                 380                 385
ctt cca tca gaa ttt ctg gta aag cct cct cta cca cat gtt gtc gtc    1495
Leu Pro Ser Glu Phe Leu Val Lys Pro Pro Leu Pro His Val Val Val
    390                 395                 400
aaa caa agg ggt gac tcg gag aag act gac caa cat aaa atg gaa agc    1543
Lys Gln Arg Gly Asp Ser Glu Lys Thr Asp Gln His Lys Met Glu Ser
405                 410                 415                 420
tca gct gag aac gta gtt ggg agg ttg tca aat caa ggt cat cat caa    1591
Ser Ala Glu Asn Val Val Gly Arg Leu Ser Asn Gln Gly His His Gln
                425                 430                 435
caa tcc aac tac atg cct ttt gca aac aac cca ccg gct tca ccg gct    1639
Gln Ser Asn Tyr Met Pro Phe Ala Asn Asn Pro Pro Ala Ser Pro Ala
            440                 445                 450
cca aat gga tat tgc ttt cct cct cag cct cct cct tca gga aat cat    1687
Pro Asn Gly Tyr Cys Phe Pro Pro Gln Pro Pro Pro Ser Gly Asn His
        455                 460                 465
cag caa tgg ttg atc cct gta atg tct ccc tcg gaa gga ctg ata tac    1735
Gln Gln Trp Leu Ile Pro Val Met Ser Pro Ser Glu Gly Leu Ile Tyr
    470                 475                 480
aag cct cac cca ggt atg gca cac acg ggg cat tat gga gga tat tat    1783
Lys Pro His Pro Gly Met Ala His Thr Gly His Tyr Gly Gly Tyr Tyr
485                 490                 495                 500
ggt cat tat atg cct aca cca atg gta atg cct caa tat cac ccc ggc    1831
Gly His Tyr Met Pro Thr Pro Met Val Met Pro Gln Tyr His Pro Gly
                505                 510                 515
atg gga ttc cca cct cct ggt aat ggc tac ttc cct cca tat gga atg    1879
Met Gly Phe Pro Pro Pro Gly Asn Gly Tyr Phe Pro Pro Tyr Gly Met
            520                 525                 530
atg ccc acc ata atg aac cca tat tgt tca agc caa caa caa caa caa    1927
Met Pro Thr Ile Met Asn Pro Tyr Cys Ser Ser Gln Gln Gln Gln Gln
        535                 540                 545
caa caa ccc aat gag caa atg aac cag ttt gga cat cct gga aat ctt    1975
Gln Gln Pro Asn Glu Gln Met Asn Gln Phe Gly His Pro Gly Asn Leu
    550                 555                 560
cag aac acc caa caa caa caa cag aga tct gat aat gaa cct gct cca    2023
Gln Asn Thr Gln Gln Gln Gln Arg Ser Asp Asn Glu Pro Ala Pro
565                 570                 575                 580
cag caa cag caa cag cca aca aag tct tat ccg cga gca aga aag agc    2071
Gln Gln Gln Gln Gln Pro Thr Lys Ser Tyr Pro Arg Ala Arg Lys Ser
                585                 590                 595
agg caa ggg agc aca gga agc agt cca agt ggg cca cag gga atc tct    2119
Arg Gln Gly Ser Thr Gly Ser Ser Pro Ser Gly Pro Gln Gly Ile Ser
            600                 605                 610
ggt agc aag tcc ttt cgg cca ttc gca gcc gtt gat gag gac agc aac    2167
Gly Ser Lys Ser Phe Arg Pro Phe Ala Ala Val Asp Glu Asp Ser Asn
        615                 620                 625
atc aac aat gca cct gag caa acg atg aca aca acc aca acg acg aca    2215
Ile Asn Asn Ala Pro Glu Gln Thr Met Thr Thr Thr Thr Thr Thr Thr
    630                 635                 640
aga aca act gtt act cag aca aca aga gat ggg gga gga gtg acg aga    2263
Arg Thr Thr Val Thr Gln Thr Thr Arg Asp Gly Gly Gly Val Thr Arg
645                 650                 655                 660
```

```
        gtg ata aag gtg gta cct cac aac gca aag ctc gcg agt gag aat gct    2311
        Val Ile Lys Val Val Pro His Asn Ala Lys Leu Ala Ser Glu Asn Ala
                        665                 670                 675
        gcc aga att ttc cag tca ata caa gaa gaa cgt aaa cgc tat gac tcc    2359
        Ala Arg Ile Phe Gln Ser Ile Gln Glu Glu Arg Lys Arg Tyr Asp Ser
                        680                 685                 690
        tct aag cct taa tcctctctat gcgtattgta cttgatatgt attttacaaa        2411
        Ser Lys Pro
                695
        attagaaaaa ttgtgataga tgttatcctc aatatatgta ccatgtaaac gtattatggt  2471
        gtaagcctca tttatatgtg ttaatttgtc ttaaaaaaaa aaaaaaa                2518

<210> SEQ ID NO 2
<211> LENGTH: 695
<212> TYPE: PRT
<213> ORGANISM: Arabidopsis thaliana

<400> SEQUENCE: 2

Met Lys Arg Gly Lys Asp Glu Glu Lys Ile Leu Glu Pro Met Phe Pro
        1               5                   10                  15
        Arg Leu His Val Asn Asp Ala Asp Lys Gly Gly Pro Arg Ala Pro Pro
                        20                  25                  30
        Arg Asn Lys Met Ala Leu Tyr Glu Gln Leu Ser Ile Pro Ser Gln Arg
                        35                  40                  45
        Phe Gly Asp His Gly Thr Met Asn Ser Arg Ser Asn Asn Thr Ser Thr
                50                  55                  60
        Leu Val His Pro Gly Pro Ser Ser Gln Pro Cys Gly Val Glu Arg Asn
        65                  70                  75                  80
        Leu Ser Val Gln His Leu Asp Ser Ser Ala Ala Asn Gln Ala Thr Glu
                        85                  90                  95
        Lys Phe Val Ser Gln Met Ser Phe Met Glu Asn Val Arg Ser Ser Ala
                        100                 105                 110
        Gln His Asp Gln Arg Lys Met Val Arg Glu Glu Asp Phe Ala Val
                        115                 120                 125
        Pro Val Tyr Ile Asn Ser Arg Arg Ser Gln Ser His Gly Arg Thr Lys
                        130                 135                 140
        Ser Gly Ile Glu Lys Glu Lys His Thr Pro Met Val Ala Pro Ser Ser
        145                 150                 155                 160
        His His Ser Ile Arg Phe Gln Glu Val Asn Gln Thr Gly Ser Lys Gln
                        165                 170                 175
        Asn Val Cys Leu Ala Thr Cys Ser Lys Pro Glu Val Arg Asp Gln Val
                        180                 185                 190
        Lys Ala Asn Ala Arg Ser Gly Gly Phe Val Ile Ser Leu Asp Val Ser
                        195                 200                 205
        Val Thr Glu Glu Ile Asp Leu Glu Lys Ser Ala Ser Ser His Asp Arg
                        210                 215                 220
        Val Asn Asp Tyr Asn Ala Ser Leu Arg Gln Glu Ser Arg Asn Arg Leu
        225                 230                 235                 240
        Tyr Arg Asp Gly Gly Lys Thr Arg Leu Lys Asp Thr Asp Asn Gly Ala
                        245                 250                 255
        Glu Ser His Leu Ala Thr Glu Asn His Ser Gln Glu Gly His Gly Ser
                        260                 265                 270
        Pro Glu Asp Ile Asp Asn Asp Arg Glu Tyr Ser Lys Ser Arg Ala Cys
                        275                 280                 285
        Ala Ser Leu Gln Gln Ile Asn Glu Glu Ala Ser Asp Val Ser Asp
                        290                 295                 300
        Asp Ser Met Val Asp Ser Ile Ser Ser Ile Asp Val Ser Pro Asp Asp
        305                 310                 315                 320
        Val Val Gly Ile Leu Gly Gln Lys Arg Phe Trp Arg Ala Arg Lys Ala
                        325                 330                 335
        Ile Ala Asn Gln Gln Arg Val Phe Ala Val Gln Leu Phe Glu Leu His
                        340                 345                 350
        Arg Leu Ile Lys Val Gln Lys Leu Pro Ile Ala Ala Ser Asp Leu Leu
                        355                 360                 365
        Leu Asp Glu Ile Ser Phe Leu Gly Lys Val Ser Ala Lys Ser Tyr Pro
                370                 375                 380
        Val Lys Lys Leu Leu Pro Ser Glu Phe Leu Val Lys Pro Pro Leu Pro
        385                 390                 395                 400
        His Val Val Lys Gln Arg Gly Asp Ser Glu Lys Thr Asp Gln His
                        405                 410                 415
        Lys Met Glu Ser Ser Ala Glu Asn Val Val Gly Arg Leu Ser Asn Gln
                        420                 425                 430
        Gly His His Gln Gln Ser Asn Tyr Met Pro Phe Ala Asn Asn Pro Pro
                        435                 440                 445
        Ala Ser Pro Ala Pro Asn Gly Tyr Cys Phe Pro Pro Gln Pro Pro
                        450                 455                 460
        Ser Gly Asn His Gln Gln Trp Leu Ile Pro Val Met Ser Pro Ser Glu
```

```
                465                 470                 475                 480
        Gly Leu Ile Tyr Lys Pro His Pro Gly Met Ala His Thr Gly His Tyr
                        485                 490                 495
        Gly Gly Tyr Tyr Gly His Tyr Met Pro Thr Pro Met Val Met Pro Gln
                        500                 505                 510
        Tyr His Pro Gly Met Gly Phe Pro Pro Gly Asn Gly Tyr Phe Pro
                        515                 520                 525
        Pro Tyr Gly Met Met Pro Thr Ile Met Asn Pro Tyr Cys Ser Ser Gln
                    530                 535                 540
        Gln Gln Gln Gln Gln Gln Pro Asn Glu Gln Met Asn Gln Phe Gly His
        545                 550                 555                 560
        Pro Gly Asn Leu Gln Asn Thr Gln Gln Gln Gln Arg Ser Asp Asn
                        565                 570                 575
        Glu Pro Ala Pro Gln Gln Gln Gln Pro Thr Lys Ser Tyr Pro Arg
                    580                 585                 590
        Ala Arg Lys Ser Arg Gln Gly Ser Thr Gly Ser Ser Pro Ser Gly Pro
                    595                 600                 605
        Gln Gly Ile Ser Gly Ser Lys Ser Phe Arg Pro Phe Ala Ala Val Asp
                    610                 615                 620
        Glu Asp Ser Asn Ile Asn Asn Ala Pro Glu Gln Thr Met Thr Thr Thr
        625                 630                 635                 640
        Thr Thr Thr Arg Thr Thr Val Thr Gln Thr Thr Arg Asp Gly Gly
                        645                 650                 655
        Gly Val Thr Arg Val Ile Lys Val Pro His Asn Ala Lys Leu Ala
                    660                 665                 670
        Ser Glu Asn Ala Ala Arg Ile Phe Gln Ser Ile Gln Glu Glu Arg Lys
                675                 680                 685
        Arg Tyr Asp Ser Ser Lys Pro
        690                 695

<210> SEQ ID NO 3
<211> LENGTH: 4221
<212> TYPE: DNA
<213> ORGANISM: Arabidopsis thaliana
<220> FEATURE:
<221> NAME/KEY: promoter
<222> LOCATION: (1)..(142)
<223> OTHER INFORMATION:
<221> NAME/KEY: 5'UTR
<222> LOCATION: (143)..(425)
<223> OTHER INFORMATION:
<221> NAME/KEY: exon
<222> LOCATION: (426)..(644)
<223> OTHER INFORMATION:
<221> NAME/KEY: exon
<222> LOCATION: (1007)..(1803)
<223> OTHER INFORMATION:
<221> NAME/KEY: exon
<222> LOCATION: (2984)..(3037)
<223> OTHER INFORMATION:
<221> NAME/KEY: exon
<222> LOCATION: (3128)..(4142)
<223> OTHER INFORMATION:
<221> NAME/KEY: Intron
<222> LOCATION: (645)..(1006)
<223> OTHER INFORMATION:
<221> NAME/KEY: Intron
<222> LOCATION: (1804)..(2983)
<223> OTHER INFORMATION:
<221> NAME/KEY: Intron
<222> LOCATION: (3038)..(3127)
<223> OTHER INFORMATION:
<221> NAME/KEY: 3'UTR
<222> LOCATION: (4146)..(4221)
<223> OTHER INFORMATION:

<400> SEQUENCE: 3
tatctttggg ggctccactt ttcctatctc tttttgcccc ttcctctct ctgttcacaa      60
    gtcatcttct tccttcctct gaatcttgtt ccttttgct ctctctactt gattcaccca    120
    ctctgtttct cgattagtac gttgaaaact cactttggtt ttgtttgatt cctctttagt    180
    ctgttttcg atttcgtttt ctctgattgg tttggtggtg agatctctat cgtagtttgt    240
    cctttgggtt aagatatttc atttgattgg tgggtttgtt ttattgaagc ttattgtttgt    300
    gaaagttgga gtctttctca gtttttaggt tgaattatta agagaaaggg aagattttg    360
    gtgtgaagtt aggttatttg gggtttgaga agtttgcaag tgaaaaaggt tgtgaattgt    420
    gagtg atg aag aga ggg aaa gat gag gag aag ata ttg gaa cct atg ttt    470
          Met Lys Arg Gly Lys Asp Glu Glu Lys Ile Leu Glu Pro Met Phe
            1               5                  10                  15
```

```
cct cgg ctt cat gtg aat gat gca gat aaa gga ggg cct aga gct cct        518
Pro Arg Leu His Val Asn Asp Ala Asp Lys Gly Gly Pro Arg Ala Pro
             20                  25                  30
cct aga aac aag atg gct ctt tat gag cag ctt agt att cct tct cag        566
Pro Arg Asn Lys Met Ala Leu Tyr Glu Gln Leu Ser Ile Pro Ser Gln
         35                  40                  45
agg ttt ggt gat cat gga acg atg aat tct cgt agt aac aac aca agc        614
Arg Phe Gly Asp His Gly Thr Met Asn Ser Arg Ser Asn Asn Thr Ser
     50                  55                  60
act ttg gtt cat cct gga cca tct agt cag gtattgtttt gattttgatc          664
Thr Leu Val His Pro Gly Pro Ser Ser Gln
 65                  70
attgtatagg ctcttgatgt tattagttgt atgagtttgg atgttatata gcctgaaaga       724
gaaagtagga cattggttga tctatgtttc aattgttatc agatcatagt atcttctttt       784
tgcttatgga ttgagctttt aggattgaat tctcctgtat atatgagact cttgtagaca       844
caagtttatc taagtgtggt ttatttctta aaactaacat tcttgttgtg cctgattctt       904
tttatgttct gaagttcgat gaaagtttct tgtgattgcc ctgagcattc agactattgc       964
aaggacatga gaaataatcc ttttttaccc tcttcaatgc ag cct tgt ggt gtg         1018
                                              Pro Cys Gly Val
                                                           75
gaa aga aac tta tct gtc cag cat ctt gat tct tca gcc gca aac caa       1066
Glu Arg Asn Leu Ser Val Gln His Leu Asp Ser Ser Ala Ala Asn Gln
             80                  85                  90
gca act gag aag ttt gtc tcc caa atg tcc ttc atg gaa aat gtg aga       1114
Ala Thr Glu Lys Phe Val Ser Gln Met Ser Phe Met Glu Asn Val Arg
         95                 100                 105
tct tcg gca cag cat gat cag agg aaa atg gtg aga gag gaa gaa gat       1162
Ser Ser Ala Gln His Asp Gln Arg Lys Met Val Arg Glu Glu Glu Asp
110                 115                 120                 125
ttt gca gtt cca gta tat att aac tca aga aga tct cag tct cat ggc       1210
Phe Ala Val Pro Val Tyr Ile Asn Ser Arg Arg Ser Gln Ser His Gly
             130                 135                 140
aga acc aag agt ggt att gag aag gaa aaa cac acc cca atg gtg gca       1258
Arg Thr Lys Ser Gly Ile Glu Lys Glu Lys His Thr Pro Met Val Ala
         145                 150                 155
cct agc tct cat cac tcc att cga ttt caa gaa gtg aat cag aca ggc       1306
Pro Ser Ser His His Ser Ile Arg Phe Gln Glu Val Asn Gln Thr Gly
     160                 165                 170
tca aag caa aac gta tgt ttg gct act tgt tca aaa cct gaa gtt agg       1354
Ser Lys Gln Asn Val Cys Leu Ala Thr Cys Ser Lys Pro Glu Val Arg
175                 180                 185
gat cag gtc aag gcg aat gca agg tca ggt ggc ttt gta atc tct tta       1402
Asp Gln Val Lys Ala Asn Ala Arg Ser Gly Gly Phe Val Ile Ser Leu
190                 195                 200                 205
gat gta tca gtc aca gag gag att gat ctc gaa aaa tca gca tca agt       1450
Asp Val Ser Val Thr Glu Glu Ile Asp Leu Glu Lys Ser Ala Ser Ser
             210                 215                 220
cat gat aga gta aat gat tat aat gct tcc ttg aga caa gag tct aga       1498
His Asp Arg Val Asn Asp Tyr Asn Ala Ser Leu Arg Gln Glu Ser Arg
         225                 230                 235
aat cgg tta tac cga gat ggt ggc aaa act cgt ctg aag gac act gat       1546
Asn Arg Leu Tyr Arg Asp Gly Gly Lys Thr Arg Leu Lys Asp Thr Asp
     240                 245                 250
aat gga gct gaa tct cac ttg gca acg gaa aat cat tca caa gag ggt       1594
Asn Gly Ala Glu Ser His Leu Ala Thr Glu Asn His Ser Gln Glu Gly
255                 260                 265
cat ggc agt cct gaa gac att gat aat gat cgt gaa tac agc aaa agc       1642
His Gly Ser Pro Glu Asp Ile Asp Asn Asp Arg Glu Tyr Ser Lys Ser
270                 275                 280                 285
aga gca tgc gcc tct ctg cag cag ata aat gaa gag gca agt gat gac       1690
Arg Ala Cys Ala Ser Leu Gln Gln Ile Asn Glu Glu Ala Ser Asp Asp
             290                 295                 300
gtt tct gat gat tcg atg gtg gat tct ata tcc agc ata gat gtc tct       1738
Val Ser Asp Asp Ser Met Val Asp Ser Ile Ser Ser Ile Asp Val Ser
         305                 310                 315
ccc gat gat gtt gtg ggt ata tta ggt caa aaa cgt ttc tgg aga gca       1786
Pro Asp Asp Val Val Gly Ile Leu Gly Gln Lys Arg Phe Trp Arg Ala
     320                 325                 330
agg aaa gcc att gcc aa gtaagttcac tagaaattta cagtttggtt              1833
Arg Lys Ala Ile Ala Asn
     335
atttattctc cgctctttct atttatctcc ttctttgata ccaacatttt ttgcttgaaa      1893
gaagttaata tttaagcatt gttccgtagt cttactgaag cttttttcctc tgttgttttt    1953
tgctattttc attgaggact gtggtagggc atatttcact atcaccaaat ttcaaatttc     2013
tagaacactc tccttcatat tttttttcat gattaatgct gcaattgatt gctgatatac     2073
atatatgact ataactcagt ttcatattct gtctcatttt gggagaaaga gatttcaggt     2133
ttatgcttga gaagtgatgg ttctatagtt gagaggcccc tgattcatct aaaatggtcc     2193
tattatgtgt ttagttgtag agtcctcggt agaatattaa cgcgtttaac acgttggatc     2253
atgttatagc agggagggac attctctgtt gacctatatt gtgcaaggtg cccgccgatg     2313
```

-continued

```
gctttattac tataccttct ttgcatctgg ttgttggaac atgtccctgt ctcggtttgg         2373
tattgctttt attctgcact gtcgtcttgg gcattttccc tacttgtcat tcaaggggtt         2433
gaaccaggta gggaaatgtt tttccgagga ccccaggatc taaattttag ttaaccatac         2493
gtaaagttag ttttgagtct tatgacgatg cagaattata gtttcttctt actactgctt         2553
aagaggatcc ttagtgtggt tgtgaactac agagttttta tgattgtagg cttcatgact         2613
taacttttaa ggttcaatgt actctaatcc atatggtaag gtatcggatt cacgaccaat         2673
gcaaataata agatttttat ttccttgcttc ttgttaaata tctgacatct cattttgcag         2733
aggataagct gcgctgtaag ctagatttca ataagcccgt cctttgcatt gttatctatg         2793
ctttaatatg tcattggacc cattgatttg gttttcttct atctttttttg attggctatg         2853
tattctgtt tctttttttcc tatctcattt cgatcgtatt gttccattag ctgttcaacc         2913
taaactatgt ctctctttgt tgaactttttg atggataatc ttcttaatgt gactctgttt         2973
```

| | | | |
|---|---|---|---|
| ctcattacag t caa caa aga gta ttt gct gtt caa cta ttt gag ttg cac<br>           Gln Gln Arg Val Phe Ala Val Gln Leu Phe Glu Leu His<br>           340                   345                350 | | | 3023 |
| aga ctg att aag gt  aaagtcattc agaaacttct catatgtttc catgagtatt<br>Arg Leu Ile Lys Val<br>           355 | | | 3077 |
| tgtttcttct cgagctgaaa caaacctctt caactgtgta ataatcaggt t caa aaa<br>                                                                                      Gln Lys | | | 3134 |

```
ctt att gct gca tca ccg gat ctc ttg ctc gat gag atc agt ttt ctt          3182
Leu Ile Ala Ala Ser Pro Asp Leu Leu Leu Asp Glu Ile Ser Phe Leu
360                 365                 370                 375
gga aaa gtt tct gct aaa agc tat cca gtg aag aag ctc ctt cca tca          3230
Gly Lys Val Ser Ala Lys Ser Tyr Pro Val Lys Lys Leu Leu Pro Ser
        380                 385                 390
gaa ttt ctg gta aag cct cct cta cca cat gtt gtc gtc aaa caa agg          3278
Glu Phe Leu Val Lys Pro Pro Leu Pro His Val Val Val Lys Gln Arg
    395                 400                 405
ggt gac tcg gag aag act gac caa cat aaa atg gaa agc tca gct gag          3326
Gly Asp Ser Glu Lys Thr Asp Gln His Lys Met Glu Ser Ser Ala Glu
410                 415                 420
aac gta gtt ggg agg ttg tca aat caa ggt cat cat caa caa tcc aac          3374
Asn Val Val Gly Arg Leu Ser Asn Gln Gly His His Gln Gln Ser Asn
    425                 430                 435
tac atg cct ttt gca aac aac cca ccg gct tca ccg gct cca aat gga          3422
Tyr Met Pro Phe Ala Asn Asn Pro Pro Ala Ser Pro Ala Pro Asn Gly
440                 445                 450                 455
tat tgc ttt cct cct cag cct cct cct tca gga aat cat cag caa tgg          3470
Tyr Cys Phe Pro Pro Gln Pro Pro Pro Ser Gly Asn His Gln Gln Trp
        460                 465                 470
ttg atc cct gta atg tct ccc tcg gaa gga ctg ata tac aag cct cac          3518
Leu Ile Pro Val Met Ser Pro Ser Glu Gly Leu Ile Tyr Lys Pro His
    475                 480                 485
cca ggt atg gca cac acg ggg cat tat gga gga tat tat ggt cat tat          3566
Pro Gly Met Ala His Thr Gly His Tyr Gly Gly Tyr Tyr Gly His Tyr
490                 495                 500
atg cct aca cca atg gta atg cct caa tat cac ccc ggc atg gga ttc          3614
Met Pro Thr Pro Met Val Met Pro Gln Tyr His Pro Gly Met Gly Phe
    505                 510                 515
cca cct cct ggt aat ggc tac ttc cct cca tat gga atg atg ccc acc          3662
Pro Pro Pro Gly Asn Gly Tyr Phe Pro Pro Tyr Gly Met Met Pro Thr
520                 525                 530                 535
ata atg aac cca tat tgt tca agc caa caa caa caa caa caa caa ccc          3710
Ile Met Asn Pro Tyr Cys Ser Ser Gln Gln Gln Gln Gln Gln Gln Pro
        540                 545                 550
aat gag caa atg aac cag ttt gga cat cct gga aat ctt cag aac acc          3758
Asn Glu Gln Met Asn Gln Phe Gly His Pro Gly Asn Leu Gln Asn Thr
    555                 560                 565
caa caa caa caa cag aga tct gat aat gaa cct gct cca cag caa cag          3806
Gln Gln Gln Gln Gln Arg Ser Asp Asn Glu Pro Ala Pro Gln Gln Gln
570                 575                 580
caa cag cca aca aag tct tat ccg cga gca aga aag agc agg caa ggg          3854
Gln Gln Pro Thr Lys Ser Tyr Pro Arg Ala Arg Lys Ser Arg Gln Gly
    585                 590                 595
agc aca gga agc agt cca agt ggg cca cag gga tct ggt agc aag          3902
Ser Thr Gly Ser Ser Pro Ser Gly Pro Gln Gly Ile Ser Gly Ser Lys
600                 605                 610                 615
tcc ttt cgg cca ttc gca gcc gtt gat gag gac agc aac atc aac aat          3950
Ser Phe Arg Pro Phe Ala Ala Val Asp Glu Asp Ser Asn Ile Asn Asn
        620                 625                 630
gca cct gag caa acg atg aca aca acc aca acg aca aga aca act          3998
Ala Pro Glu Gln Thr Met Thr Thr Thr Thr Thr Thr Arg Thr Thr
    635                 640                 645
gtt act cag aca aca aga gat ggg gga gtg acg aga gtg ata aag          4046
Val Thr Gln Thr Thr Arg Asp Gly Gly Val Thr Arg Val Ile Lys
650                 655                 660
gtg gta cct cac aac gca aag ctc gcg agt gag aat gct gcc aga att          4094
Val Val Pro His Asn Ala Lys Leu Ala Ser Glu Asn Ala Ala Arg Ile
    665                 670                 675
```

```
ttc cag tca ata caa gaa gaa cgt aaa cgc tat gac tcc tct aag cct    4142
Phe Gln Ser Ile Gln Glu Glu Arg Lys Arg Tyr Asp Ser Ser Lys Pro
680             685                 690                 695
taatcctctc tatgcgtatt gtacttgata tgtattttac aaaattagaa aaattgtgat   4202
agatgttatc ctcaatata                                               4221
```

<210> SEQ ID NO 4
<211> LENGTH: 2088
<212> TYPE: DNA
<213> ORGANISM: Arabidopsis thaliana

<400> SEQUENCE: 4

```
atgaagagag ggaaagatga ggagaagata ttggaaccta tgtttcctcg gcttcatgtg     60
aatgatgcag ataaaggagg gcctagagct cctcctagaa acaagatggc tctttatgag    120
cagcttagta ttccttctca gaggtttggt gatcatggaa cgatgaattc tcgtagtaac    180
aacacaagca ctttggttca tcctggacca tctagtcagc cttgtggtgt ggaaagaaac    240
ttatctgtcc agcatcttga ttcttcagcc gcaaaccaag caactgagaa gtttgtctcc    300
caaatgtcct tcatggaaaa tgtgagatct tcggcacagc atgatcagag gaaaatggtg    360
agagaggaag aagatttttgc agttccagta tatattaact caagaagatc tcagtctcat    420
ggcagaacca agagtggtat tgagaaggaa aaacacaccc caatggtggc acctagctct    480
catcactcca ttcgatttca agaagtgaat cagacaggct caaagcaaaa cgtatgtttg    540
gctacttgtt caaaacctga agttagggat caggtcaagg cgaatgcaag gtcaggtggc    600
tttgtaatct ctttagatgt atcagtcaca gaggagattg atctcgaaaa atcagcatca    660
agtcatgata gagtaaatga ttataatgct tccttgagac aagagtctag aaatcggtta    720
taccgagatg gtggcaaaac tcgtctgaag gacactgata tggagctga atctcacttg    780
gcaacggaaa atcattcaca agagggtcat ggcagtcctg aagacattga taatgatcgt    840
gaatacagca aaagcagagc atgcgcctct ctgcagcaga taatgaagaa ggcaagtgat    900
gacgtttctg atgattcgat ggtggattct atatccagca tagatgtctc tcccgatgat    960
gttgtgggta tattaggtca aaaacgtttc tggagagcaa ggaaagccat tgccaatcaa   1020
caaagagtat ttgctgttca actatttgag ttgcacagac tgattaaggt tcaaaaactt   1080
attgctgcat caccggatct cttgctcgat gagatcagtt ttcttggaaa agtttctgct   1140
aaaagctatc cagtgaagaa gctccttcca tcagaatttc tggtaaagcc tcctctacca   1200
catgttgtcg tcaaacaaag gggtgactcg gagaagactg accaacataa aatggaaagc   1260
tcagctgaga acgtagttgg gaggttgtca aatcaaggtc atcatcaaca atccaactac   1320
atgccttttg caaacaaccc accggcttca ccggctccaa atggatattg cttttcctcct   1380
cagcctcctc cttcaggaaa tcatcagcaa tggttgatcc ctgtaatgtc tccctcggaa   1440
ggactgatat acaagcctca cccaggtatg gcacacacgg gcattatgg aggatattat    1500
ggtcattata tgcctacacc aatggtaatg cctcaatatc accccggcat gggattccca   1560
cctcctggta atggctactt ccctccatat ggaatgatgc ccaccataat gaacccatat   1620
tgttcaagcc aacaacaaca caacaacaa cccaatgagc aaatgaacca gtttggacat   1680
cctggaaatc ttcagaacac ccaacaacaa caacagagat ctgataatga acctgctcca   1740
cagcaacagc aacagccaac aaagtcttat ccgcgagcaa gaaagagcag gcaagggagc   1800
acaggaagca gtccaagtgg gccacaggga atctctggta gcaagtcctt tcggccattc   1860
gcagccgttg atgaggacag caacatcaac aatgcacctg agcaaacgat gacaacaacc   1920
acaacgacga caagaacaac tgttactcag acaacaagag atggggggag agtgacgaga   1980
gtgataaagg tggtacctca caacgcaaag ctcgcgagtg agaatgctgc cagaattttc   2040
cagtcaatac aagaagaacg taaacgctat gactcctcta agccttaa                2088
```

<210> SEQ ID NO 5
<211> LENGTH: 4071
<212> TYPE: DNA
<213> ORGANISM: Arabidopsis thaliana

<400> SEQUENCE: 5

```
tgtgttagtg actttcctcc tgaagaattc aactcaagac atgagacaat agattcatga     60
caatatctac tacagtactt gcataacaca aatgtaaact aactaacaat tgatagttta    120
gtacacaatc caaattgcaa aagagagata ctgcaaattga tctaatcaaa actcatgcat    180
tctacagttc cataagacat ttcaaatcac taatctgaag aaatatatga cattaataac    240
aaatatttga taactaaaca gacatttgga tcagaaatga agttaaatta agcatttaat    300
tgcttaataa tttaattgat tgattcaaag gcgtaataac acaaaattct tcgggggaat    360
ttgaagggat agagcaaatc gcttagggta aaatgaaaac agcgataagt aacgaattat    420
caaagtctga gttaagaatc aggaaattga gggattgaag aagaataaag ggacctggtt    480
caggaggaat tgagacgtga gtacgctgtg ttggagagga cgacgtcatt ttcgatcaaa    540
gcagcagatt cagcaacgga tggatgggtc tttactcttt gggctgaaga taaccgcaac    600
tagattcttc ctgagttttt tttttctttt tgataaaacg agagcccta caggtaaaaa    660
cccaataaaa accacgatca attttattt ggacatttaa tatttaatta tttttaaatta   720
gaaaataatt acacgaatta ctaaattgta taatatgata ttaaaaaatt aagtgttatt    780
gatgtgtttt cggtctgact gtctataaaa aaaatcccca acataagag ttgttgttgg    840
agtcattaaa ggatctaatg gtttgtggtg gtgtgaccat tggagaggg tttgttgatg    900
ggtcgtgtgt ttcaccatta atattatcaa atggttctcg gttgattggt cattttttga    960
gtcatcaaat ggctcatatg ttacgctatg tatcacgaaa atatatattt ttctcttaaa   1020
accattcttc cttttccaat aaatatggat tataaattcc cgtgaagata aatatgtggt   1080
ttttactttt cgtttttttc ctaggtgagg agggtgttat tggttgctaa tttaaaagga   1140
atttttgatga tttttaataat atcataaaaa gtaaattaag attttaaact attgctaggg   1200
agttttttta tgatcttgtt aattagtttt tcacagtctt gtaaagttttt tcaaacaatc   1260
```

```
tctctatttt gatgatattt ttttacttta ttttgtgaac aaaagtgtag aaaattatta    1320
aacaataaca caatatttta attcattaac aatcatagtt tttttaaaa aaaattgaa     1380
taacgccaaa cttttagtga ctttataatt tttttaatta taaggtaagt ctcctaagat   1440
atatgttttg ggttaaagta ttcacaatgt ccaccatgtt atgtgatata ttacccatgt   1500
atattcattt tgtcatttaa tcttaccttt ttgcattttt gtttggctta aaatctacaa   1560
tatcgtttta ctattaaaaa aacctgtaat attcatttac aaatcaatat tttattcttt   1620
ttagacatat cctatttta tttctacatt cttttcaaaa tagttactaa aataattttt    1680
ttctaaaagc catgaatata aacacaacaa ctaatcaatc tccacaatat atattatata   1740
ttaacaaaaa gtgtattggt gataaaaagt acttgatgat acactaaaca aaaaggataa   1800
atgggagaat ttttatttt gaaagatgaa acattttagg ttatatattt catgaccctt    1860
ataaataaaa ttcctggctc caccactgga tatctctaca tatttccaac atcaatatcc   1920
attgatattt gataatcttt accaaaaatt cgcaatctcc tttagagtga aagcgagtat   1980
aaccgtatga ccaaactatt ttgagtacca ttggtaattc cttaccttaa gcttccagag   2040
gtattagtgc tatatattca tagtgccacc gagtatttg aactccgaaa tgatttctca    2100
ctatccgacc actcccaatt atataacatg cttagaatta ttcgtaagat ggatcgtagt   2160
tgcattttac gacaccatac aggacaagtc catgatagtt tgagttggtg gattttgaa    2220
cccctgcaaa tttatttat acataacaaa ggcccaatc cattccttag catcacaact     2280
tgggacttct atcttttgaa ggatacattc acttgttggt tttggtaaat atgattgttt   2340
ctttacttcc gaataagcaa tatataaaag tatctaaaaa cggaagtaac ttttgatgat   2400
cctaaaggtt ttgtaattga tacatgtcca aaaacctctt aatattcttt ctcacaaact   2460
gttgatggag ttaacaaagg gagacaaggt aattgggaca atatcaacgt tagatacagg   2520
acaagtgaaa aatgtggggt tgatgtcttc agctgcagca tatcaccgtt ggtatatatt   2580
gtcaattatt agtcctatgg atttgaaacg tgttttagta aataagagtg tccaagtggg   2640
acatttccaa taacgtatca cagctcctag agcttttgct atgtttctct aggcctgggc   2700
cgcctagccc acattccaag caaggaaatg aatggagttg ggcatcaaaa ttttggaagc   2760
attttttaaga caaatatcct tttaagttc ctttttttaaa cataaactat attttaggct   2820
tttttaagat aaatattatt tggatttct ttcactcata tttttggatt tcaacttaac    2880
aaaacatagg gcgtgtctat ttgactccac ctacccaccc tactggagtt cgatcccact   2940
aaatcgcgtt atcccgcata gtagggattg actatggatc ggactttgtc gatccaaaga   3000
tatctaagaa attcagaaaa gattgtataa aattcagaaa cgattttacg aaattcatga   3060
aaaatgagaa atacatgttt tttttaattt acgtcggcat taaaaacgtt ggaccggctc   3120
tgtgtttcac caaagaaatt gtttcagttt atgcatgatc ttcaacttcc atattcttgt   3180
tttcaattct ggaaatccct aacagatcgg agctccctc attcagtgag ttggaagatt    3240
gcatgattat ataattactc ttcacatcca catatattac attatattcc cctataattt   3300
catacaaccc tagaaaagaa tcttcaagta atcaatcgt gtcgatgact ccactcattt    3360
gctagaaaag aaaaaacaaa cagacttcat ttagcttgaa acaatctttt attcaacatt   3420
acaaagcact gatcaaagaa cctctaacat ggtaatatat ctatgacatt ttacgtatcc   3480
taaaagaaaa caaaaagtga tgtattggat gatgtttttt ttttttactt tctagtttct   3540
tattacaacg acaaaagag tccacgtcgt cacgcacttt tccggtggtg aaaaaaatgt    3600
ccaaatggat taaatctata atatctccag agagatcctc tccttctatc tttgggggct   3660
ccacttttcc tatctctttt tgcccctttc ctctctctgt tcacaagtca tcttcttcct   3720
tcctctgaat cttgttcctt tttgctctct ctacttgatt cacccactct gtttctcgat   3780
tagtacgttg aaaactcact ttggttttgt ttgattcctc tttagtctgt ttttcgattt   3840
cgttttctct gattggtttg gtggtgagat ctctatcgta gtttgtcctt tgggttaaga   3900
tatttcattt gattggtggg tttgttttat tgaagcttat tgttgtgaaa gttgtgagtct   3960
ttctcagttt ttaggttgaa ttattaagag aaagggaaga tttttggtgt gaagttaggt   4020
tatttggggt ttgagaagtt tgcaagtgaa aaaggttgtg aattgtgagt g            4071
```

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: synthetic oligonucleotide corresponding to a portion of the Arabi
      doposis ELF3 sequence

<400> SEQUENCE: 6

```
tgaaaactca ctttggtttt gttt                                           24
```

<210> SEQ ID NO 7
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a portion of the Arabi
      doposis ELF3 sequence

<400> SEQUENCE: 7

```
aagacaaatt aacacatata aatga                                          25
```

<210> SEQ ID NO 8
<211> LENGTH: 24
<212> TYPE: DNA
<213> ORGANISM: ARTIFICIAL SEQUENCE

```
<220> FEATURE:
<223> OTHER INFORMATION: synthetic oligonucleotide corresponding to a portion of the Arabi
      doposis ELF3 sequence

<400> SEQUENCE: 8
atgaatagag ggaaagatga ggag                                          24

<210> SEQ ID NO 9
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a portion of the Arabi
      doposis ELF3 sequence

<400> SEQUENCE: 9
ttaaggctta gaggagtcat agcgt                                         25

<210> SEQ ID NO 10
<211> LENGTH: 22
<212> TYPE: DNA
<213> ORGANISM: ARTIFICIAL SEQUENCE
<220> FEATURE:
<223> OTHER INFORMATION: synthetic oligonucleotide corresponding to a portion of the Arabi
      doposis ELF3 sequence

<400> SEQUENCE: 10
agtaagagag ggaaagatga gg                                            22

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: synthetic oligonucleotide corresponding to a portion of the Arabi
      doposis ELF3 sequence

<400> SEQUENCE: 11
gccaccatct cggtataacc                                               20

<210> SEQ ID NO 12
<211> LENGTH: 1960
<212> TYPE: DNA
<213> ORGANISM: Cardamine oligosperma
<220> FEATURE:
<221> NAME/KEY: CDS
<222> LOCATION: (1)..(1959)
<223> OTHER INFORMATION:

<400> SEQUENCE: 12 atg aag aga ggg aaa gat gat gag aag ata ctg gaa cct atg ttt cct     48
    Met Lys Arg Gly Lys Asp Asp Glu Lys Ile Leu Glu Pro Met Phe Pro
    1               5                   10                  15
    aga ctt cat gtg aat gat gca gat aaa gga gga cct aga gct cct cct     96
    Arg Leu His Val Asn Asp Ala Asp Lys Gly Gly Pro Arg Ala Pro Pro
                20                  25                  30
    aga aac aag atg gct ctt tat gag cag ctt agt atc cct tct cag agg     144
    Arg Asn Lys Met Ala Leu Tyr Glu Gln Leu Ser Ile Pro Ser Gln Arg
            35                  40                  45
    ttt ggt gat cat gga aat ttg tct ctg agt tct cgt agt aac aac aca     192
    Phe Gly Asp His Gly Asn Leu Ser Leu Ser Ser Arg Ser Asn Asn Thr
        50                  55                  60
    agt act ttg gtt cac cct gga cca tct aat cag cag tct tgt ggt gtg     240
    Ser Thr Leu Val His Pro Gly Pro Ser Asn Gln Gln Ser Cys Gly Val
    65                  70                  75                  80
    gaa cga aac tta tct gtc cag cat ctt gat tct tca gct gca gtc cat     288
    Glu Arg Asn Leu Ser Val Gln His Leu Asp Ser Ser Ala Ala Val His
                    85                  90                  95
    gta act gag aat ttt gtc tcc caa atg ccc ttc atg gaa aat atg aga     336
    Val Thr Glu Asn Phe Val Ser Gln Met Pro Phe Met Glu Asn Met Arg
```

-continued

```
                    100                 105                 110
    tct ttg gca aag cat gat cag agg aaa aca gta aga gag gaa gat gac    384
    Ser Leu Ala Lys His Asp Gln Arg Lys Thr Val Arg Glu Glu Asp Asp
                115                 120                 125
    ttt gca gtt cca gtg ttt gtt aac tca aga aga ttc cag agt cat ggt    432
    Phe Ala Val Pro Val Phe Val Asn Ser Arg Arg Phe Gln Ser His Gly
    130                 135                 140
    agt acc aag agt ggg att gtg att gaa aaa cac acg aca ttg gct act    480
    Ser Thr Lys Ser Gly Ile Val Ile Glu Lys His Thr Thr Leu Ala Thr
    145                 150                 155                 160
    tgt tca aaa ctt gtt aga gat aag gtg aag atg aac gca aag tca ggt    528
    Cys Ser Lys Leu Val Arg Asp Lys Val Lys Met Asn Ala Lys Ser Gly
                165                 170                 175
    ggc ttt ata gat tta tca tca aca gag gaa gtg gat ctc gaa aaa tca    576
    Gly Phe Ile Asp Leu Ser Ser Thr Glu Glu Val Asp Leu Glu Lys Ser
                180                 185                 190
    gca tca agt tat gac aga gta aat gat tgt aat tct tcc ttg aga caa    624
    Ala Ser Ser Tyr Asp Arg Val Asn Asp Cys Asn Ser Ser Leu Arg Gln
                195                 200                 205
    gag tct aga aat aag tta tac cga gat ggt ggc gaa gct cat atg aag    672
    Glu Ser Arg Asn Lys Leu Tyr Arg Asp Gly Gly Glu Ala His Met Lys
    210                 215                 220
    gac act gct aat aga gtt gaa tct cac ttg gta acg gaa agt cat tct    720
    Asp Thr Ala Asn Arg Val Glu Ser His Leu Val Thr Glu Ser His Ser
    225                 230                 235                 240
    gag gag ggt cat ggc agt cct gat gat gat gac aac ggt cat gaa tac    768
    Glu Glu Gly His Gly Ser Pro Asp Asp Asp Asp Asn Gly His Glu Tyr
                245                 250                 255
    tgc aga agc aga gga ggc gtc tct cta cag cag ata aat gaa gag gca    816
    Cys Arg Ser Arg Gly Gly Val Ser Leu Gln Gln Ile Asn Glu Glu Ala
                260                 265                 270
    agt gat gac gtt tct gat aat tcg atg gtg gat tct ata tcc agc ata    864
    Ser Asp Asp Val Ser Asp Asn Ser Met Val Asp Ser Ile Ser Ser Ile
                275                 280                 285
    gat gtt tct cct gat gat gtt gtg gga gca tta ggt caa aaa cgt ttc    912
    Asp Val Ser Pro Asp Asp Val Val Gly Ala Leu Gly Gln Lys Arg Phe
    290                 295                 300
    tgg agg gca agg aag gct att acc aat caa caa aga gta ttt gct gtt    960
    Trp Arg Ala Arg Lys Ala Ile Thr Asn Gln Gln Arg Val Phe Ala Val
    305                 310                 315                 320
    caa cta ttt gag ttg cac aga ctg att aag gtt caa aga ctt att gct   1008
    Gln Leu Phe Glu Leu His Arg Leu Ile Lys Val Gln Arg Leu Ile Ala
                325                 330                 335
    gca tca ccg gat atc gtg ctc gac gaa atc aat tac ctt gga aaa gtt   1056
    Ala Ser Pro Asp Ile Val Leu Asp Glu Ile Asn Tyr Leu Gly Lys Val
                340                 345                 350
    tct gct aaa agc tat cca gtg aag aag ctc gtt cca tca gaa ttt atc   1104
    Ser Ala Lys Ser Tyr Pro Val Lys Lys Leu Val Pro Ser Glu Phe Ile
                355                 360                 365
    gta aag cct cct cta cca caa gtt gtc gtc aac aaa cag cac agg agc   1152
    Val Lys Pro Pro Leu Pro Gln Val Val Val Asn Lys Gln His Arg Ser
    370                 375                 380
    gac tcc gaa aag act gac caa cat aaa atg gaa tgt tca gct gag aat   1200
    Asp Ser Glu Lys Thr Asp Gln His Lys Met Glu Cys Ser Ala Glu Asn
    385                 390                 395                 400
    gtt gtt ggt agg ttg tca aac caa gga cat cat cat aat cat caa cct   1248
    Val Val Gly Arg Leu Ser Asn Gln Gly His His His Asn His Gln Pro
                405                 410                 415
    tcc aac tac atg cct ttt cca agc aac cca ccc gct tca cca gct gta   1296
    Ser Asn Tyr Met Pro Phe Pro Ser Asn Pro Pro Ala Ser Pro Ala Val
                420                 425                 430
    aac gga tgt tgc tat cct cct cag cct cct cct tca gga aac cag caa   1344
    Asn Gly Cys Cys Tyr Pro Pro Gln Pro Pro Pro Ser Gly Asn Gln Gln
                435                 440                 445
    tgg tta atc cct gtt atg tct cct tct gaa gga ctt ata tac aag cct   1392
    Trp Leu Ile Pro Val Met Ser Pro Ser Glu Gly Leu Ile Tyr Lys Pro
    450                 455                 460
    cat cct ggt atg gga cac acg ggg cac tac gga gga tat tat ggt cat   1440
    His Pro Gly Met Gly His Thr Gly His Tyr Gly Gly Tyr Tyr Gly His
    465                 470                 475                 480
    ttt atg cct ccg ccg atg gta atg cct ccg ttt cat ccg ggc atg gga   1488
    Phe Met Pro Pro Pro Met Val Met Pro Pro Phe His Pro Gly Met Gly
                485                 490                 495
    ttc cca cct cct ggt aat ggc tac ttc cct cct tat ggt gta atc cca   1536
    Phe Pro Pro Pro Gly Asn Gly Tyr Phe Pro Pro Tyr Gly Val Ile Pro
                500                 505                 510
    gcc atg atg aac cct tat ggt cca ggc caa caa caa caa caa caa cca   1584
    Ala Met Met Asn Pro Tyr Gly Pro Gly Gln Gln Gln Gln Gln Gln Pro
    515                 520                 525
```

-continued

```
caa gcc aat gaa caa acg aat cag ttt ggg tat tct ggg aat ctt cag      1632
Gln Ala Asn Glu Gln Thr Asn Gln Phe Gly Tyr Ser Gly Asn Leu Gln
    530                 535                 540
aac aac acc cat caa gaa agc tcc gtt aat gaa gct gct cct cca cag      1680
Asn Asn Thr His Gln Glu Ser Ser Val Asn Glu Ala Ala Pro Pro Gln
545                 550                 555                 560
gaa cca cta aca aag tct tat ccg cgg gct aga aag agc agg caa gtg      1728
Glu Pro Leu Thr Lys Ser Tyr Pro Arg Ala Arg Lys Ser Arg Gln Val
                565                 570                 575
agc aca gca agc agt gca agt ggg cga gag gga atc tcc ggt agc act      1776
Ser Thr Ala Ser Ser Ala Ser Gly Arg Glu Gly Ile Ser Gly Ser Thr
            580                 585                 590
tcc ttt cgt cca ttc tca gcc gtt gat gag gat aac aac gat aac aac      1824
Ser Phe Arg Pro Phe Ser Ala Val Asp Glu Asp Asn Asn Asp Asn Asn
        595                 600                 605
aac gac gca cct gat caa atg atg aca acc acc acc acg aca aga          1872
Asn Asp Ala Pro Asp Gln Met Met Thr Thr Thr Thr Thr Thr Arg
    610                 615                 620
aca act gtt act cag aca aca aga gat gga gga gaa gtg acg aga gtg      1920
Thr Thr Val Thr Gln Thr Thr Arg Asp Gly Gly Glu Val Thr Arg Val
625                 630                 635                 640
ata aag ggg ttc ctc aca atg cga agc tcg cta gtg aga a                1960
Ile Lys Gly Phe Leu Thr Met Arg Ser Ser Leu Val Arg
                645                 650
```

<210> SEQ ID NO 13
<211> LENGTH: 653
<212> TYPE: PRT
<213> ORGANISM: Cardamine oligosperma

<400> SEQUENCE: 13

```
Met Lys Arg Gly Lys Asp Asp Glu Lys Ile Leu Glu Pro Met Phe Pro
1               5                   10                  15
Arg Leu His Val Asn Asp Ala Asp Lys Gly Gly Pro Arg Ala Pro Pro
                20                  25                  30
Arg Asn Lys Met Ala Leu Tyr Glu Gln Leu Ser Ile Pro Ser Gln Arg
            35                  40                  45
Phe Gly Asp His Gly Asn Leu Ser Leu Ser Ser Arg Ser Asn Asn Thr
        50                  55                  60
Ser Thr Leu Val His Pro Gly Pro Ser Asn Gln Gln Ser Cys Gly Val
65                  70                  75                  80
Glu Arg Asn Leu Ser Val Gln His Leu Asp Ser Ser Ala Ala Val His
                85                  90                  95
Val Thr Glu Asn Phe Val Ser Gln Met Pro Phe Met Glu Asn Met Arg
                100                 105                 110
Ser Leu Ala Lys His Asp Gln Arg Lys Thr Val Arg Glu Glu Asp Asp
            115                 120                 125
Phe Ala Val Pro Val Phe Val Asn Ser Arg Phe Gln Ser His Gly
        130                 135                 140
Ser Thr Lys Ser Gly Ile Val Ile Glu Lys His Thr Thr Leu Ala Thr
145                 150                 155                 160
Cys Ser Lys Leu Val Arg Asp Lys Val Lys Met Asn Ala Lys Ser Gly
                165                 170                 175
Gly Phe Ile Asp Leu Ser Ser Thr Glu Glu Val Asp Leu Glu Lys Ser
                180                 185                 190
Ala Ser Ser Tyr Asp Arg Val Asn Asp Cys Asn Ser Ser Leu Arg Gln
            195                 200                 205
Glu Ser Arg Asn Lys Leu Tyr Arg Asp Gly Gly Glu Ala His Met Lys
        210                 215                 220
Asp Thr Ala Asn Arg Val Glu Ser His Leu Val Thr Glu Ser His Ser
225                 230                 235                 240
Glu Glu Gly His Gly Ser Pro Asp Asp Asp Asn Gly His Glu Tyr
                245                 250                 255
Cys Arg Ser Arg Gly Gly Val Ser Leu Gln Gln Ile Asn Glu Glu Ala
                260                 265                 270
Ser Asp Val Ser Asp Asn Ser Met Val Asp Ser Ile Ser Ser Ile
            275                 280                 285
Asp Val Ser Pro Asp Asp Val Gly Ala Leu Gly Gln Lys Arg Phe
        290                 295                 300
Trp Arg Ala Arg Lys Ala Ile Thr Asn Gln Gln Arg Val Phe Ala Val
305                 310                 315                 320
Gln Leu Phe Glu Leu His Arg Leu Ile Lys Val Gln Arg Leu Ile Ala
                325                 330                 335
Ala Ser Pro Asp Ile Val Leu Asp Glu Ile Asn Tyr Leu Gly Lys Val
                340                 345                 350
Ser Ala Lys Ser Tyr Pro Val Lys Lys Leu Val Pro Ser Glu Phe Ile
            355                 360                 365
```

```
            Val Lys Pro Pro Leu Pro Gln Val Val Asn Lys Gln His Arg Ser
                370                 375                 380
            Asp Ser Glu Lys Thr Asp Gln His Lys Met Glu Cys Ser Ala Glu Asn
            385                 390                 395                 400
            Val Val Gly Arg Leu Ser Asn Gln Gly His His Asn His Gln Pro
                            405                 410                 415
            Ser Asn Tyr Met Pro Phe Pro Ser Asn Pro Pro Ala Ser Pro Ala Val
                        420                 425                 430
            Asn Gly Cys Cys Tyr Pro Pro Gln Pro Pro Ser Gly Asn Gln Gln
                        435                 440                 445
            Trp Leu Ile Pro Val Met Ser Pro Ser Glu Gly Leu Ile Tyr Lys Pro
                450                 455                 460
            His Pro Gly Met Gly His Thr Gly His Tyr Gly Gly Tyr Tyr Gly His
            465                 470                 475                 480
            Phe Met Pro Pro Pro Met Val Met Pro Pro Phe His Pro Gly Met Gly
                            485                 490                 495
            Phe Pro Pro Pro Gly Asn Gly Tyr Phe Pro Pro Tyr Gly Val Ile Pro
                        500                 505                 510
            Ala Met Met Asn Pro Tyr Gly Pro Gly Gln Gln Gln Gln Gln Pro
                        515                 520                 525
            Gln Ala Asn Glu Gln Thr Asn Gln Phe Gly Tyr Ser Gly Asn Leu Gln
                530                 535                 540
            Asn Asn Thr His Gln Glu Ser Ser Val Asn Glu Ala Ala Pro Pro Gln
            545                 550                 555                 560
            Glu Pro Leu Thr Lys Ser Tyr Pro Arg Ala Arg Lys Ser Arg Gln Val
                            565                 570                 575
            Ser Thr Ala Ser Ser Ala Ser Gly Arg Glu Gly Ile Ser Gly Ser Thr
                        580                 585                 590
            Ser Phe Arg Pro Phe Ser Ala Val Asp Glu Asp Asn Asn Asp Asn Asn
                        595                 600                 605
            Asn Asp Ala Pro Asp Gln Met Met Thr Thr Thr Thr Thr Thr Thr Arg
            610                 615                 620
            Thr Thr Val Thr Gln Thr Thr Arg Asp Gly Gly Glu Val Thr Arg Val
            625                 630                 635                 640
            Ile Lys Gly Phe Leu Thr Met Arg Ser Ser Leu Val Arg
                            645                 650

<210> SEQ ID NO 14
<211> LENGTH: 3617
<212> TYPE: DNA
<213> ORGANISM: Cardamine oligosperma
<220> FEATURE:
<221> NAME/KEY: 5'UTR
<222> LOCATION: (1)..(306)
<223> OTHER INFORMATION:
<221> NAME/KEY: exon
<222> LOCATION: (307)..(531)
<223> OTHER INFORMATION:
<221> NAME/KEY: exon
<222> LOCATION: (819)..(1531)
<223> OTHER INFORMATION:
<221> NAME/KEY: exon
<222> LOCATION: (2510)..(2561)
<223> OTHER INFORMATION:
<221> NAME/KEY: exon
<222> LOCATION: (2646)..(3615)
<223> OTHER INFORMATION: partial
<221> NAME/KEY: Intron
<222> LOCATION: (532)..(818)
<223> OTHER INFORMATION:
<221> NAME/KEY: Intron
<222> LOCATION: (1532)..(2509)
<223> OTHER INFORMATION:
<221> NAME/KEY: Intron
<222> LOCATION: (2562)..(2645)
<223> OTHER INFORMATION:
<221> NAME/KEY: unsure
<222> LOCATION: (1412)..(1412)
<223> OTHER INFORMATION: W = a or t/u
<221> NAME/KEY: Unsure
<222> LOCATION: (1409)..(1412)
<223> OTHER INFORMATION: encoded amino acid is unsure due to nucleotide uncertainty
<221> NAME/KEY: unsure
<222> LOCATION: (1406)..(1406)
<223> OTHER INFORMATION: K = g or t/u
<221> NAME/KEY: unsure
<222> LOCATION: (1404)..(1406)
<223> OTHER INFORMATION: encoded amino acid is unsure due to nucleotide uncertainty
```

<221> NAME/KEY: unsure
<222> LOCATION: (1419)..(1419)
<223> OTHER INFORMATION: R = a or c
<221> NAME/KEY: unsure
<222> LOCATION: (1419)..(1421)
<223> OTHER INFORMATION: encoded amino acid is unsure due to nucleotide uncertainty

<400> SEQUENCE: 14

```
tacttgattt accatctctc ttaatttatc agctcgtgga gctctcatat ccttcgtttg      60
atttcagttc actcggtttt aaaactttgt tttctctgat tggggagatc taccgtagtc     120
ggtggtcaat tagtgggttt tgttttgagt ttcatttgat ttgtgggttt agttttttga     180
agcttattgt tacgaaattt tgggtctttt tcaattttag gtcaaataat tggggaaaag     240
ttgagaaatc gtgtgaaatt aggttatttg ggttgagaaa ttttgaagca aagtttgtga     300
gttgtg atg aag aga ggg aaa gat gat gag aag ata ctg gaa cct atg        348
       Met Lys Arg Gly Lys Asp Asp Glu Lys Ile Leu Glu Pro Met
         1               5                  10
ttt cct aga ctt cat gtg aat gat gca gat aaa gga gga cct aga gct       396
Phe Pro Arg Leu His Val Asn Asp Ala Asp Lys Gly Gly Pro Arg Ala
 15                  20                  25                  30
cct cct aga aac aag atg gct ctt tat gag cag ctt agt atc cct tct       444
Pro Pro Arg Asn Lys Met Ala Leu Tyr Glu Gln Leu Ser Ile Pro Ser
                 35                  40                  45
gag agg ttt ggt gat cat gga aat ttg tct ctg agt tct cgt agt aac       492
Glu Arg Phe Gly Asp His Gly Asn Leu Ser Leu Ser Ser Arg Ser Asn
         50                  55                  60
aac aca agt act ttg gtt cac cct gga cca tct aat cag                   541
Asn Thr Ser Thr Leu Val His Pro Gly Pro Ser Asn Gln
         65                  70                  75  gtatggagtt
gtggaaattg atgttatata gcttgcaaga gagtagtagg agttgattgt tcaatgtttt     601
cagttgtttt ttagctcatt ttagcttctt ttgttcatgg attgaactca cttgtagata     661
tcggaatata gtggatgtat atctattcta gtgtgtgaaga tttttttatgt ttgaaagttt    721
tatgatgct tcttgtgatt ggcctgaaca ttctggttac tgtattcaac ttgataagga      781
cattggaaat aatcgttttt ggtgctcttt cctgcag cag tct tgt ggt gtg gaa      836
                                          Gln Ser Cys Gly Val Glu
                                                              80
cga aac tta tct gtc cag cat ctt gat tct tca gct gca gtc cat gta       884
Arg Asn Leu Ser Val Gln His Leu Asp Ser Ser Ala Ala Val His Val
         85                  90                  95
act gag aat ttt gtc tcc caa atg ccc ttc atg gaa aat atg aga tct       932
Thr Glu Asn Phe Val Ser Gln Met Pro Phe Met Glu Asn Met Arg Ser
        100                 105                 110
ttg gca aag cat gat cag agg aaa aca gta aga gag gaa gat gac ttt       980
Leu Ala Lys His Asp Gln Arg Lys Thr Val Arg Glu Glu Asp Asp Phe
 115                 120                 125
gca gtt cca gtg ttt gtt aac tca aga aga ttc cag agt cat ggt agt      1028
Ala Val Pro Val Phe Val Asn Ser Arg Arg Phe Gln Ser His Gly Ser
 130                 135                 140                 145
acc aag agt ggg att gtg att gaa aaa cac acg aca ttg gct act tgt      1076
Thr Lys Ser Gly Ile Val Ile Glu Lys His Thr Thr Leu Ala Thr Cys
                 150                 155                 160
tca aaa ctt gtt aga gat aag gtg aag atg aac gca aag tca ggt ggc      1124
Ser Lys Leu Val Arg Asp Lys Val Lys Met Asn Ala Lys Ser Gly Gly
         165                 170                 175
ttt ata gat tta tca tca aca gag gaa gtg gat ctc gaa aaa tca gca      1172
Phe Ile Asp Leu Ser Ser Thr Glu Glu Val Asp Leu Glu Lys Ser Ala
 180                 185                 190
tca agt tat gac aga gta aat gat tgt aat tct tcc ttg aga caa gag      1220
Ser Ser Tyr Asp Arg Val Asn Asp Cys Asn Ser Ser Leu Arg Gln Glu
 195                 200                 205
tct aga aat aag tta tac cga gat ggt ggc gaa gct cat atg aag gac      1268
Ser Arg Asn Lys Leu Tyr Arg Asp Gly Gly Glu Ala His Met Lys Asp
 210                 215                 220                 225
act gct aat aga gtt gaa tct cac ttg gta acg gaa agt cat tct gag      1316
Thr Ala Asn Arg Val Glu Ser His Leu Val Thr Glu Ser His Ser Glu
                 230                 235                 240
gag ggt cat ggc agt cct gat gat gat gac aac ggt cat gaa tac tgc      1364
Glu Gly His Gly Ser Pro Asp Asp Asp Asp Asn Gly His Glu Tyr Cys
         245                 250                 255
aga agc aga gga ggc gtc tct cta cag cag ata aat gaa gak gca agw      1412
Arg Ser Arg Gly Gly Val Ser Leu Gln Gln Ile Asn Glu Xaa Ala Xaa
 260                 265                 270
gat gac rtt tct gat aat tcg atg gtg gat tct ata tcc agc ata gat      1460
Asp Asp Xaa Ser Asp Asn Ser Met Val Asp Ser Ile Ser Ser Ile Asp
 275                 280                 285
gtt tct cct gat gat gtt gtg gga gca tta ggt caa aaa cgt ttc tgg      1508
Val Ser Pro Asp Asp Val Val Gly Ala Leu Gly Gln Lys Arg Phe Trp
 290                 295                 300                 305
agg gca agg aag gct att acc aa  gtaagttcac tagttttttt ttacggttta     1561
Arg Ala Arg Lys Ala Ile Thr
```

```
                              Arg Ala Arg Lys Ala Ile Thr Asn
                                              310
gttaactttg ttatttattt tccgctcttt ctatccatct ctttctttga taccgacttt      1621
gctacttgca agaagttaat gctgaagcat agttacctaa ttagactgaa gctttcctct      1681
gctgttttt ggacactttc ttttagtttc tttgctttt catgcatact gatacaatgg       1741
atatataact cggttatat tgtgtctcaa tttgggagaa acgatttcgg gttttggct        1801
tgagacatga tggtactata gtggagaagc ccccccttga ttcctcgtaa aatggtcctg      1861
ttatatgtta gttgacgagc cctcggtagc atattaacgc gttggatcat gttatagcag     1921
ggagggacat tctctgttga cgtacattgt acaaggtgcc cgccgagaca gttcatggct     1981
ttatactctt gtcttctttg catctgcttg ttggaacatg tccctgtctc ggtttggtat     2041
tgcttttatt ctgcacttc gtcttgggca tttcccttc ttgtcattca agggttgaa        2101
ccaggtaggg gaacttgttt tcgaggaccc tgggatctaa attttagtta accgtacata     2161
gaacctagtt atgagtctta tgacagtgca gaattatagt tgcttttgc tactgcttaa     2221
taggatcctt agagtggttg tgaactacgg ttttttctat ggatttaga ctctaggtgt     2281
tcttatcgct acgataaggt atcacgatac atgaccaact catataacaa gctttttcta    2341
gcttttcgtt gagggtaagc tagaaatcta ttaacccatc ctttgcttaa cccattcttg    2401
catttaattt cttttttgtgt tattgcttct gttttcccttt cgtatttctt cattttacta   2461
ttcgattagc tggtcatatt ccttatgaaa ttccgtttct cattacag t caa caa        2516
                                                         Gln Gln
                                                            315
aga gta ttt gct gtt caa cta ttt gag ttg cac aga ctg att aag           2561
Arg Val Phe Ala Val Gln Leu Phe Glu Leu His Arg Leu Ile Lys
        320                 325                 330
gtaaagtaat tcagaaaact tctcctataa atattttgc tgaaacaaac gtcttcatct     2621
gtgctttgtt tctgtaatac tcag gtt caa aga ctt att gct gca tca ccg        2672
                              Val Gln Arg Leu Ile Ala Ala Ser Pro
                                                  335
gat atc gtg ctc gac gaa atc aat tac ctt gga aaa gtt tct gct aaa       2720
Asp Ile Val Leu Asp Glu Ile Asn Tyr Leu Gly Lys Val Ser Ala Lys
340                 345                 350                 355
agc tat cca gtg aag aag ctc gtt cca tca gaa ttt atc gta aag cct       2768
Ser Tyr Pro Val Lys Lys Leu Val Pro Ser Glu Phe Ile Val Lys Pro
            360                 365                 370
cct cta cca caa gtt gtc gtc aac aaa cag cac agg agc gac tcc gaa       2816
Pro Leu Pro Gln Val Val Val Asn Lys Gln His Arg Ser Asp Ser Glu
        375                 380                 385
aag act gac caa cat aaa atg gaa tgc tca gct gag aat gtt gtt ggt       2864
Lys Thr Asp Gln His Lys Met Glu Cys Ser Ala Glu Asn Val Val Gly
    390                 395                 400
agg ttg tca aac caa gga cat cat cat aat cat caa cct tcc aac tac       2912
Arg Leu Ser Asn Gln Gly His His His Asn His Gln Pro Ser Asn Tyr
405                 410                 415
atg cct ttt cca agc aac cca ccc gct tca cca gct gta aac gga tgt       2960
Met Pro Phe Pro Ser Asn Pro Pro Ala Ser Pro Ala Val Asn Gly Cys
420                 425                 430                 435
tgc tat cct cct cag cct cct cct tca gga aac cag caa tgg tta atc       3008
Cys Tyr Pro Pro Gln Pro Pro Pro Ser Gly Asn Gln Gln Trp Leu Ile
            440                 445                 450
cct gtt atg tct cct tct gaa gga ctt ata tac aag cct cat cct ggt       3056
Pro Val Met Ser Pro Ser Glu Gly Leu Ile Tyr Lys Pro His Pro Gly
        455                 460                 465
atg gga cac acg ggg cac tac gga gga tat tat ggt cat ttt atg cct       3104
Met Gly His Thr Gly His Tyr Gly Gly Tyr Tyr Gly His Phe Met Pro
    470                 475                 480
ccg ccg atg gta atg cct ccg ttt cat ccg ggc atg gga ttc cca cct       3152
Pro Pro Met Val Met Pro Pro Phe His Pro Gly Met Gly Phe Pro Pro
485                 490                 495
cct ggt aat ggc tac ttc cct cct tat ggt gta atc cca gcc atg atg       3200
Pro Gly Asn Gly Tyr Phe Pro Pro Tyr Gly Val Ile Pro Ala Met Met
500                 505                 510                 515
aac cct tat ggt cca ggc caa caa caa caa caa caa cca caa gcc aat       3248
Asn Pro Tyr Gly Pro Gly Gln Gln Gln Gln Gln Gln Pro Gln Ala Asn
            520                 525                 530
gaa caa acg aat cag ttt ggg tat tct ggg aat ctt cag aac aac acc       3296
Glu Gln Thr Asn Gln Phe Gly Tyr Ser Gly Asn Leu Gln Asn Asn Thr
        535                 540                 545
cat caa gaa agc tcc gtt aat gaa gct gct cct cca cag gaa cca cta       3344
His Gln Glu Ser Ser Val Asn Glu Ala Ala Pro Pro Gln Glu Pro Leu
    550                 555                 560
aca aag tct tat ccg cgg gct aga aag agc agg caa gtg agc aca gca       3392
Thr Lys Ser Tyr Pro Arg Ala Arg Lys Ser Arg Gln Val Ser Thr Ala
565                 570                 575
agc agt gca agt ggg cga gag gga atc tcc ggt agc act tcc ttt cgt       3440
Ser Ser Ala Ser Gly Arg Glu Gly Ile Ser Gly Ser Thr Ser Phe Arg
580                 585                 590                 595
cca ttc tca gcc gtt gat gag gat aac aac gat aac aac aac gac gca       3488
Pro Phe Ser Ala Val Asp Glu Asp Asn Asn Asp Asn Asn Asn Asp Ala
            600                 605                 610
cct gat caa atg atg aca acc acc acg acc acg aca aga aca act gtt       3536
```

-continued

```
        Pro Asp Gln Met Met Thr Thr Thr Thr Thr Thr Arg Thr Thr Val
                        615                 620                 625
        act cag aca aca aga gat gga gga gaa gtg acg aga gtg ata aag gtg          3584
        Thr Gln Thr Thr Arg Asp Gly Gly Glu Val Thr Arg Val Ile Lys Val
                        630                 635                 640
        gtt cct cac aat gcg aag ctc gct agt gag a at                              3617
        Val Pro His Asn Ala Lys Leu Ala Ser Glu
        645                 650
```

<210> SEQ ID NO 15
<211> LENGTH: 430
<212> TYPE: DNA
<213> ORGANISM: Pisum sativum
<220> FEATURE:
<221> NAME/KEY: exon
<222> LOCATION: (2)..(13)
<223> OTHER INFORMATION: partial
<221> NAME/KEY: exon
<222> LOCATION: (95)..(430)
<223> OTHER INFORMATION: partial
<221> NAME/KEY: Intron
<222> LOCATION: (14)..(94)
<223> OTHER INFORMATION: partial

<400> SEQUENCE: 15

```
        t aga ctg ata aag gtaaattatc tttgacattg atcagtgctc tcacacaccc            53
          Arg Leu Ile Lys
          1
        ttgagtctta ctgtaatgat taattctttt tacttaagca g gtc caa caa cta att         109
                                                    Val Gln Gln Leu Ile
                                                                    5
        gcc gga tcg cca gat ctt ttg ttt gat gat ggt gct ttt ctg gga aag          157
        Ala Gly Ser Pro Asp Leu Leu Phe Asp Asp Gly Ala Phe Leu Gly Lys
        10                  15                  20                  25
        tct ctt cca gat gga tct act cct aaa aaa ctc tca ttg gaa tat gtt          205
        Ser Leu Pro Asp Gly Ser Thr Pro Lys Lys Leu Ser Leu Glu Tyr Val
                        30                  35                  40
        gta aaa gct cgg cta caa aat ctt aag cgc aaa gtt gat tct gaa aag          253
        Val Lys Ala Arg Leu Gln Asn Leu Lys Arg Lys Val Asp Ser Glu Lys
                        45                  50                  55
        ata aat caa aac atg gaa tgt tct gca gag aat gct gtt ggt aaa aca          301
        Ile Asn Gln Asn Met Glu Cys Ser Ala Glu Asn Ala Val Gly Lys Thr
                        60                  65                  70
        tct att tcg tcc gtg aaa aat acg agc cac ctt tct agt tcc atg cct          349
        Ser Ile Ser Ser Val Lys Asn Thr Ser His Leu Ser Ser Ser Met Pro
        75                  80                  85
        ttt gcc gga aat cca cac caa gga aat gtg gca gct gat aat ggg atg          397
        Phe Ala Gly Asn Pro His Gln Gly Asn Val Ala Ala Asp Asn Gly Met
        90                  95                  100                 105
        ggt ccc tgg tgt ttc aat cag tca cct ggg cat                              430
        Gly Pro Trp Cys Phe Asn Gln Ser Pro Gly His
                        110                 115
```

<210> SEQ ID NO 16
<211> LENGTH: 116
<212> TYPE: PRT
<213> ORGANISM: Pisum sativum

<400> SEQUENCE: 16

```
        Arg Leu Ile Lys Val Gln Gln Leu Ile Ala Gly Ser Pro Asp Leu Leu
        1               5                   10                  15
        Phe Asp Asp Gly Ala Phe Leu Gly Lys Ser Leu Pro Asp Gly Ser Thr
                        20                  25                  30
        Pro Lys Lys Leu Ser Leu Glu Tyr Val Val Lys Ala Arg Leu Gln Asn
                        35                  40                  45
        Leu Lys Arg Lys Val Asp Ser Glu Lys Ile Asn Gln Asn Met Glu Cys
        50                  55                  60
        Ser Ala Glu Asn Ala Val Gly Lys Thr Ser Ile Ser Ser Val Lys Asn
        65                  70                  75                  80
        Thr Ser His Leu Ser Ser Ser Met Pro Phe Ala Gly Asn Pro His Gln
                        85                  90                  95
        Gly Asn Val Ala Ala Asp Asn Gly Met Gly Pro Trp Cys Phe Asn Gln
                        100                 105                 110
        Ser Pro Gly His
                        115
```

<210> SEQ ID NO 17
<211> LENGTH: 74
<212> TYPE: PRT
<213> ORGANISM: Broccoli/Cauliflower

<400> SEQUENCE: 17

```
Arg Leu Ile Met Val Gln Lys Met Val Ala Lys Ser Pro Asn Leu Val
 1               5                  10                  15
Leu Lys Asn Lys Ile Asn Gly Gly Ser Lys Phe Lys Lys Pro Asn Thr
            20                  25                  30
Glu Asn Gln Lys Pro Val Thr Glu Ala Tyr Pro Glu His Met Lys Pro
        35                  40                  45
Lys Ile Pro Leu Pro Phe Ile Ser Lys Glu Leu Met Thr Pro Ile Trp
    50                  55                  60
Gln Gln Gln Leu Leu Pro Pro Gln Glu Asn
65                  70
```

<210> SEQ ID NO 18
<211> LENGTH: 555
<212> TYPE: DNA
<213> ORGANISM: Glycine max

<400> SEQUENCE: 18

```
acgcgtccga gcacctctca gtgctacttt catgaatccc gcctatcaat tcccagcttc      60
tcatccagta gttgggggttt caccgtttgt ccctccggcc agtcacacct acttcgctcc    120
ctttggcatg ccggtaatga atcaagcaac atcaggatca gccgttgaac aggtgaacca    180
gtttgctgca caaggttctc atggtcaaaa tggtcattca tctgtagagg gagccgattt    240
taacactcat cataaccaaa gctcatctaa cttgccagtt cagaagaatg gagctaggtt    300
acatgttaaa aaatctcagg ccctgaagga gagagggtta caagggagca caagaagcag    360
tcctagtgaa atggcacagg gaatcagagc acggaaaatt gctgacggaa gtgatgcacg    420
tctctttctc ttcacgctga tgaaaccaga cagcaaacac aagccatcaa agttgtaccc    480
cataaccgga aatccgcgac ggaatcagca gctagaattg ttcaatccat tcaagaagag    540
agaaaacagc atgat                                                      555
```

<210> SEQ ID NO 19
<211> LENGTH: 185
<212> TYPE: PRT
<213> ORGANISM: Glycine max

<400> SEQUENCE: 19

```
Arg Val Arg Ala Pro Leu Ser Ala Thr Phe Met Asn Pro Ala Tyr Gln
 1               5                  10                  15
Phe Pro Ala Ser His Pro Val Val Gly Val Ser Pro Phe Val Pro Pro
            20                  25                  30
Ala Ser His Thr Tyr Phe Ala Pro Phe Gly Met Pro Val Met Asn Gln
        35                  40                  45
Ala Thr Ser Gly Ser Ala Val Glu Gln Val Asn Gln Phe Ala Ala Gln
    50                  55                  60
Gly Ser His Gly Gln Asn Gly His Ser Ser Val Glu Gly Ala Asp Phe
65                  70                  75                  80
Asn Thr His His Asn Gln Ser Ser Ser Asn Leu Pro Val Gln Lys Asn
                85                  90                  95
Gly Ala Arg Leu His Val Lys Lys Ser Gln Ala Leu Lys Glu Arg Gly
            100                 105                 110
Leu Gln Gly Ser Thr Arg Ser Ser Pro Ser Glu Met Ala Gln Gly Ile
        115                 120                 125
Arg Ala Arg Lys Ile Ala Asp Gly Ser Asp Ala Gln Ser Leu Ser Leu
    130                 135                 140
His Ala Asp Glu Thr Arg Gln Gln Thr Gln Ala Ile Lys Val Val Pro
145                 150                 155                 160
His Asn Arg Lys Ser Ala Thr Glu Ser Ala Ala Arg Ile Val Gln Ser
                165                 170                 175
Ile Gln Glu Glu Arg Lys Gln His Asp
            180                 185
```

<210> SEQ ID NO 20
<211> LENGTH: 577
<212> TYPE: DNA
<213> ORGANISM: Lycopersicon esculentum

<400> SEQUENCE: 20

```
     tccattttca cacagtcgtt tgatcttttg ccgactcttc ccttgttttt ttttctcaac      60
     tgtaatctct ttcttcatat tattgtgctt accaacaagg cctgttacat gatcacagaa     120
     aaatataata gtaattttgt gaaattatac atcttttttg cttctgtgtg cttcagaaat     180
     ctcttgattt ctatgtaaag attgtgtttt gggtatttgg gtcggtagaa ttcttgtttt     240
     tttaggtggg gtttgcttgg ttttcttcaa ttttgattgg ttttgttgaa aagttcagaa     300
     atttgatgta attgtacgga tttctttgaa ttttgaagt tgaatgtata gtaaagtttc      360
     gttttttttgg tttaatttaa tgaatgttgg agattgggtg aacctgttga gaagctatta   420
     aagggaagaa atgaagagag gaaagggtga agagaagttg atgggaccta tgtttccaag     480
     gcttcatgtt aatgatacag aaaagggagg tccaaaagca cctccaagaa acaaaatggc     540
     tctttatgag cagctcagta ttccttctca gagattc                              577
```

<210> SEQ ID NO 21
<211> LENGTH: 582
<212> TYPE: DNA
<213> ORGANISM: Lycopersicon esculentum
<220> FEATURE:
<221> NAME/KEY: 5'UTR
<222> LOCATION: (1)..(43)
<223> OTHER INFORMATION:
<221> NAME/KEY: exon
<222> LOCATION: (44)..(582)
<223> OTHER INFORMATION:

<400> SEQUENCE: 21

```
     attattcgtg agttttggag gctaactact gaggtagagg aag atg aaa aga ggt        55
                                                     Met Lys Arg Gly
                                                       1
     aca ggt gaa gag aaa gtt atg ggg cct atg ttt cca agg ctt aat gtt       103
     Thr Gly Glu Glu Lys Val Met Gly Pro Met Phe Pro Arg Leu Asn Val
      5                  10                  15                  20
     aat gat aca gaa aaa gga ggt cca aga gca cct cca agg aac aag atg       151
     Asn Asp Thr Glu Lys Gly Gly Pro Arg Ala Pro Pro Arg Asn Lys Met
                      25                  30                  35
     gct ctt tat gaa caa ctg agt atc cct tcc caa cga tac aac cct ggt       199
     Ala Leu Tyr Glu Gln Leu Ser Ile Pro Ser Gln Arg Tyr Asn Pro Gly
              40                  45                  50
     gat ttg cct cat aac agt agt aac agt gca aat ttg gtc ctt cct cac       247
     Asp Leu Pro His Asn Ser Ser Asn Ser Ala Asn Leu Val Leu Pro His
      55                  60                  65
     cca agc cag gag aat gaa cac gaa aga ggt gta tta ttc tct aga caa       295
     Pro Ser Gln Glu Asn Glu His Glu Arg Gly Val Leu Phe Ser Arg Gln
      70                  75                  80
     ctt cct gca tta aga cat cca gtt gaa aag cca tat gga cgt agt tct       343
     Leu Pro Ala Leu Arg His Pro Val Glu Lys Pro Tyr Gly Arg Ser Ser
     85                  90                  95                 100
     ggt tca aat act cca ttg cgg gaa gtt aag tct aaa agg cag aca gaa       391
     Gly Ser Asn Thr Pro Leu Arg Glu Val Lys Ser Lys Arg Gln Thr Glu
                     105                 110                 115
     aag gaa gat ttt aga gtt ccc act ttt gat aac tcc aag gag cgt gca       439
     Lys Glu Asp Phe Arg Val Pro Thr Phe Asp Asn Ser Lys Glu Arg Ala
                 120                 125                 130
     gta aac aca gag gac tat tct aaa ggt acc tca gat ata gat aag cga       487
     Val Asn Thr Glu Asp Tyr Ser Lys Gly Thr Ser Asp Ile Asp Lys Arg
             135                 140                 145
     gac agt act ttg aag cgg act gat caa ctc tcc cat gtc aca ccg aga       535
     Asp Ser Thr Leu Lys Arg Thr Asp Gln Leu Ser His Val Thr Pro Arg
         150                 155                 160
     gag aat ctt gtt aat acc ttt ggt gaa tca cat aag acc aat ata gt        582
     Glu Asn Leu Val Asn Thr Phe Gly Glu Ser His Lys Thr Asn Ile
     165                 170                 175
```

<210> SEQ ID NO 22
<211> LENGTH: 1347
<212> TYPE: DNA
<213> ORGANISM: Lycopersicon esculentum
<220> FEATURE:
<221> NAME/KEY: exon
<222> LOCATION: (2)..(1171)
<223> OTHER INFORMATION:
<221> NAME/KEY: 3'UTR
<222> LOCATION: (1172)..(1347)
<223> OTHER INFORMATION:

<400> SEQUENCE: 22

-continued

```
t ttg gac cga ggt gac gac tta tct gag act tcc aga gtg aaa tct att         49
  Leu Asp Arg Gly Asp Asp Leu Ser Glu Thr Ser Arg Val Glu Ser Ile
  1               5                   10                  15
tct gga aca gac atc tct cct gat gac att gta gga ata att ggc tta           97
Ser Gly Thr Asp Ile Ser Pro Asp Asp Ile Val Gly Ile Ile Gly Leu
                20                  25                  30
aag cgt ttc tgg aaa gcc aga aga gca att gtc aac cag caa aga gtg          145
Lys Arg Phe Trp Lys Ala Arg Arg Ala Ile Val Asn Gln Gln Arg Val
            35                  40                  45
ttt gca atc caa gtg ttc gag ttg cat cga cta ata aag gta caa agg          193
Phe Ala Ile Gln Val Phe Glu Leu His Arg Leu Ile Lys Val Gln Arg
        50                  55                  60
ctc att gcc ggg tca cca aat agt tcg ctc gaa gat cct gct tat tta          241
Leu Ile Ala Gly Ser Pro Asn Ser Ser Leu Glu Asp Pro Ala Tyr Leu
65                  70                  75                  80
ggc aaa cct tta aag agt tca tcg atc aaa aga ctt cca ttg gac tgt          289
Gly Lys Pro Leu Lys Ser Ser Ser Ile Lys Arg Leu Pro Leu Asp Cys
                85                  90                  95
att gtt aga gaa tct caa agt gtt ctg aag cgc aag cat gat tct gag          337
Ile Val Arg Glu Ser Gln Ser Val Leu Lys Arg Lys His Asp Ser Glu
            100                 105                 110
aag cct cac ttc agg atg gaa cac act gcc gaa agc aat gtg gga aag          385
Lys Pro His Phe Arg Met Glu His Thr Ala Glu Ser Asn Val Gly Lys
        115                 120                 125
gca tct ctc tct act gtg caa aat ggt agt caa ctc tct agc cac aaa          433
Ala Ser Leu Ser Thr Val Gln Asn Gly Ser Gln Leu Ser Ser His Lys
    130                 135                 140
cca ttt tca gga act cca ctg cct aca cct gta aca aat gat tct aat          481
Pro Phe Ser Gly Thr Pro Leu Pro Thr Pro Val Thr Asn Asp Ser Asn
145                 150                 155                 160
gcg ggt cct tgg tgc ttc caa caa cct tcc ggg cac caa tgg ttg atc          529
Ala Gly Pro Trp Cys Phe Gln Gln Pro Ser Gly His Gln Trp Leu Ile
                165                 170                 175
cca gtg atg tct cct tct gag gga ctt gta tac aag cca ttt tct gga          577
Pro Val Met Ser Pro Ser Glu Gly Leu Val Tyr Lys Pro Phe Ser Gly
            180                 185                 190
cct gga ttc acg agt cct att tgt gga agt ggg cct tca gga tcg agt          625
Pro Gly Phe Thr Ser Pro Ile Cys Gly Ser Gly Pro Ser Gly Ser Ser
        195                 200                 205
cca aca atg ggg aac ttt ttt gct cca aca tat gga gtt cct gct cct          673
Pro Thr Met Gly Asn Phe Phe Ala Pro Thr Tyr Gly Val Pro Ala Pro
    210                 215                 220
aat cct cac tat caa ggt atg gga gtt cct ttt gca cct ccg act ggt          721
Asn Pro His Tyr Gln Gly Met Gly Val Pro Phe Ala Pro Pro Thr Gly
225                 230                 235                 240
cat ggt tac ttt cgg caa tat ggc atg cca gct atg aat cca cca att          769
His Gly Tyr Phe Arg Gln Tyr Gly Met Pro Ala Met Asn Pro Pro Ile
                245                 250                 255
tca tca act gct agt gaa gaa tcg aac cag tat acc atg cct ggt tta          817
Ser Ser Thr Ala Ser Glu Glu Ser Asn Gln Tyr Thr Met Pro Gly Leu
            260                 265                 270
caa cac cag ttt tct gga gta gtt gat gac gtt caa cat tca aca tca          865
Gln His Gln Phe Ser Gly Val Val Asp Asp Val Gln His Ser Thr Ser
        275                 280                 285
gga ctc agt aat gtt cta aat cag aag aaa gaa aat gtc ccg gat gtt          913
Gly Leu Ser Asn Val Leu Asn Gln Lys Lys Glu Asn Val Pro Asp Val
    290                 295                 300
gta agg tat caa tcc aca aaa gat aat gag gta caa gcc agc agt gca          961
Val Arg Tyr Gln Ser Thr Lys Asp Asn Glu Val Gln Ala Ser Ser Ala
305                 310                 315                 320
agt agt cct att gag aca gca gga aga aac atg ctc tct ctt ttt ccc         1009
Ser Ser Pro Ile Glu Thr Ala Gly Arg Asn Met Leu Ser Leu Phe Pro
                325                 330                 335
acg tct cca gtt act gac aac cgt gat ggt agc cct cag gct tgt gtg         1057
Thr Ser Pro Val Thr Asp Asn Arg Asp Gly Ser Pro Gln Ala Cys Val
            340                 345                 350
cct gat aat cca gcc aga gtt atc aag gtt gta cct cac aat gca agg         1105
Pro Asp Asn Pro Ala Arg Val Ile Lys Val Val Pro His Asn Ala Arg
        355                 360                 365
tct gct aca gaa tcc gta gct cgg ata ttt cag tct att caa caa gag         1153
Ser Ala Thr Glu Ser Val Ala Arg Ile Phe Gln Ser Ile Gln Gln Glu
    370                 375                 380
aga aat aat atg act tag gtttaacaca tctataagta gcttaccttg                 1201
Arg Asn Asn Met Thr
385
tgaatatgac catttgctca tcctggcaaa atgtagtagt ttcagtcaat ttgttgtatc       1261
tttctttttct acagaaagta tgtaatagct gtattttaat ttggttgctg tagataagca      1321
tacctgcaaa aaaaaaaaaa aaaaac                                            1347
```

<210> SEQ ID NO 23
<211> LENGTH: 389
<212> TYPE: PRT
<213> ORGANISM: Lycopersicon esculentum

<400> SEQUENCE: 23

```
Leu Asp Arg Gly Asp Asp Leu Ser Glu Thr Ser Arg Val Glu Ser Ile
1               5                   10                  15
Ser Gly Thr Asp Ile Ser Pro Asp Asp Ile Val Gly Ile Ile Gly Leu
            20                  25                  30
Lys Arg Phe Trp Lys Ala Arg Arg Ala Ile Val Asn Gln Gln Arg Val
        35                  40                  45
Phe Ala Ile Gln Val Phe Glu Leu His Arg Leu Ile Lys Val Gln Arg
    50                  55                  60
Leu Ile Ala Gly Ser Pro Asn Ser Ser Leu Glu Asp Pro Ala Tyr Leu
65                  70                  75                  80
Gly Lys Pro Leu Lys Ser Ser Ile Lys Arg Leu Pro Leu Asp Cys
                85                  90                  95
Ile Val Arg Glu Ser Gln Ser Val Leu Lys Arg Lys His Asp Ser Glu
            100                 105                 110
Lys Pro His Phe Arg Met Glu His Thr Ala Glu Ser Asn Val Gly Lys
        115                 120                 125
Ala Ser Leu Ser Thr Val Gln Asn Gly Ser Gln Leu Ser Ser His Lys
    130                 135                 140
Pro Phe Ser Gly Thr Pro Leu Pro Thr Pro Val Thr Asn Asp Ser Asn
145                 150                 155                 160
Ala Gly Pro Trp Cys Phe Gln Gln Pro Ser Gly His Gln Trp Leu Ile
                165                 170                 175
Pro Val Met Ser Pro Ser Glu Gly Leu Val Tyr Lys Pro Phe Ser Gly
            180                 185                 190
Pro Gly Phe Thr Ser Pro Ile Cys Gly Ser Gly Pro Ser Gly Ser Ser
        195                 200                 205
Pro Thr Met Gly Asn Phe Phe Ala Pro Thr Tyr Gly Val Pro Ala Pro
    210                 215                 220
Asn Pro His Tyr Gln Gly Met Gly Val Pro Phe Ala Pro Pro Thr Gly
225                 230                 235                 240
His Gly Tyr Phe Arg Gln Tyr Gly Met Pro Ala Met Asn Pro Pro Ile
                245                 250                 255
Ser Ser Thr Ala Ser Glu Glu Ser Asn Gln Tyr Thr Met Pro Gly Leu
            260                 265                 270
Gln His Gln Phe Ser Gly Val Val Asp Asp Val Gln His Ser Thr Ser
        275                 280                 285
Gly Leu Ser Asn Val Leu Asn Gln Lys Lys Glu Asn Val Pro Asp Val
    290                 295                 300
Val Arg Tyr Gln Ser Thr Lys Asp Asn Glu Val Gln Ala Ser Ser Ala
305                 310                 315                 320
Ser Ser Pro Ile Glu Thr Ala Gly Arg Asn Met Leu Ser Leu Phe Pro
                325                 330                 335
Thr Ser Pro Val Thr Asp Asn Arg Asp Gly Ser Pro Gln Ala Cys Val
            340                 345                 350
Pro Asp Asn Pro Ala Arg Val Ile Lys Val Pro His Asn Ala Arg
        355                 360                 365
Ser Ala Thr Glu Ser Val Ala Arg Ile Phe Gln Ser Ile Gln Gln Glu
    370                 375                 380
Arg Asn Asn Met Thr
385
```

<210> SEQ ID NO 24
<211> LENGTH: 179
<212> TYPE: PRT
<213> ORGANISM: Lycopersicon esculentum

<400> SEQUENCE: 24

```
Met Lys Arg Gly Thr Gly Glu Glu Lys Val Met Gly Pro Met Phe Pro
1               5                   10                  15
Arg Leu Asn Val Asn Asp Thr Glu Lys Gly Gly Pro Arg Ala Pro Pro
            20                  25                  30
Arg Asn Lys Met Ala Leu Tyr Glu Gln Leu Ser Ile Pro Ser Gln Arg
        35                  40                  45
Tyr Asn Pro Gly Asp Leu Pro His Asn Ser Ser Asn Ser Ala Asn Leu
    50                  55                  60
Val Leu Pro His Pro Ser Gln Glu Asn Glu His Glu Arg Gly Val Leu
65                  70                  75                  80
Phe Ser Arg Gln Leu Pro Ala Leu Arg His Pro Val Glu Lys Pro Tyr
                85                  90                  95
```

```
          Gly Arg Ser Ser Gly Ser Asn Thr Pro Leu Arg Glu Val Lys Ser Lys
                          100                 105                 110
          Arg Gln Thr Glu Lys Glu Asp Phe Arg Val Pro Thr Phe Asp Asn Ser
                      115                 120                 125
          Lys Glu Arg Ala Val Asn Thr Glu Asp Tyr Ser Lys Gly Thr Ser Asp
          130                 135                 140
          Ile Asp Lys Arg Asp Ser Thr Leu Lys Arg Thr Asp Gln Leu Ser His
          145                 150                 155                 160
          Val Thr Pro Arg Glu Asn Leu Val Asn Thr Phe Gly Glu Ser His Lys
                          165                 170                 175
          Thr Asn Ile

<210> SEQ ID NO 25
<211> LENGTH: 49
<212> TYPE: PRT
<213> ORGANISM: Lycopersicon esculentum

<400> SEQUENCE: 25

Met Lys Arg Gly Lys Gly Glu Glu Lys Leu Met Gly Pro Met Phe Pro
          1               5                   10                  15
          Arg Leu His Val Asn Asp Thr Glu Lys Gly Gly Pro Lys Ala Pro Pro
                      20                  25                  30
          Arg Asn Lys Met Ala Leu Tyr Glu Gln Leu Ser Ile Pro Ser Gln Arg
                      35                  40                  45
          Phe

<210> SEQ ID NO 26
<211> LENGTH: 4478
<212> TYPE: DNA
<213> ORGANISM: Oryza sativa
<220> FEATURE:
<221> NAME/KEY: exon
<222> LOCATION: (1)..(261)
<223> OTHER INFORMATION:
<221> NAME/KEY: exon
<222> LOCATION: (1660)..(2645)
<223> OTHER INFORMATION:
<221> NAME/KEY: exon
<222> LOCATION: (3330)..(3381)
<223> OTHER INFORMATION:
<221> NAME/KEY: exon
<222> LOCATION: (3495)..(4478)
<223> OTHER INFORMATION:
<221> NAME/KEY: Intron
<222> LOCATION: (262)..(1659)
<223> OTHER INFORMATION:
<221> NAME/KEY: Intron
<222> LOCATION: (2646)..(3329)
<223> OTHER INFORMATION:
<221> NAME/KEY: Intron
<222> LOCATION: (3382)..(3494)
<223> OTHER INFORMATION:

<400> SEQUENCE: 26 atg gcg acg agg gga gga ggc gga gga gga gga ggg aag gag gcg aag        48
          Met Ala Thr Arg Gly Gly Gly Gly Gly Gly Gly Gly Lys Glu Ala Lys
          1               5                   10                  15
          ggg aag gtg atg ggc ccg ctg ttc ccg cgg ctc cac gtc aac gac gcg        96
          Gly Lys Val Met Gly Pro Leu Phe Pro Arg Leu His Val Asn Asp Ala
                      20                  25                  30
          gcc aag ggc gga ggc ccg cgg gcg ccg ccc cgg aac aag atg gcg ctc       144
          Ala Lys Gly Gly Gly Pro Arg Ala Pro Pro Arg Asn Lys Met Ala Leu
                      35                  40                  45
          tac gag cag ttc acc gtg ccc tcg cat cgc ttc agc ggc gga gga ggc       192
          Tyr Glu Gln Phe Thr Val Pro Ser His Arg Phe Ser Gly Gly Gly Gly
                      50                  55                  60
          ggc ggc gga gta gga ggc agc ccc gcg cac tcg acg tcg gcg gcg agc       240
          Gly Gly Gly Val Gly Gly Ser Pro Ala His Ser Thr Ser Ala Ala Ser
          65                  70                  75                  80
          cag agc cag agc cag agc cag gtgactcgac gtcctgcccg tatgatcgat          291
          Gln Ser Gln Ser Gln Ser Gln
                      85
          tcgattgggg gtagtgtgtg cgactgctaa attggtacta gtaggcgaca attctgtgca     351
          aatgagcta  aacgccttgc aaatcgaatc gaattagaag cctaaattgg taggcaataa     411
          ttctgtgcaa tggagctaaa cttccttgca aatcgaatag aactaaaagc tggaagata      471
```

-continued

```
atttcgaggc acaaatggtg ccctcgacgt cgacgagcta ggtcagaggg ggcgtttcac    531
gccttaccct ttgtagttat ctcggttggg atagatgaat tgatgggcga atttagtgca    591
acggagctaa acacatggaa aaattggata agattaaggc agagaagccc agtttgaggc    651
acaaatgcca tgttcctttt gtgctgatta atctatcatg ccgtcgacat gtgattcaat    711
tacttgcaaa tatagtcata caattgtggt aggagtaaca tgcttgcacg ttgtcatagt    771
gtcattattg atctttctcc gtgctgataa ctcacttgtg ttgaaggcga aagagcagaa    831
caaaaccatt atatgcagtt tacatccagct cttccggtag attttggag acggggcata    891
agttccttgc aaacaatatc ggatattata gcttattgca aattgtatat ggccagatat    951
gctatgattg tgtttgctga ggtctggtgt ttgtaatata caaacaaaaa ggtccacatg   1011
tgaaactgca tgtagcgcag gtggcaaaga gtagccgtag tgctgctcaa cgtactgtgt   1071
tctattctcc ctgacgtgct caccttcctt aaatcattga cactaggttc ctccttagtg   1131
tcttgcattt ttgcctgccg aaaaaaaaag gtccacgtga aagggaatga taaaaatggt   1191
ggttgatatg ctttgattgt caggcacacg ttcaacctgt atgtgataaa tatcaacggt   1251
tttctaatac tgttttcagc aaggatttag gagtggaaaa tattctttag aacaaatctg   1311
caatagcctc ccacaacaca tccaactacc ttttgataat gggatagtta tagacatgaa   1371
gtgcgaatgg caaaagtcca agtcatagat ttccaaatga agaaatgtga acaaaataag   1431
aaagaaagaa gtccatttgc agtattatgt ctcttttgcc cttctttggg tcgaaaataa   1491
aataaaaaat cgagatctta ccatgagata cttaatctcc caccactttt tctaattcaa   1551
catggaagtt cttggatagt ttaaatacgc ttcctaccaa ttagcgtgga atcctcgcaa   1611
tttttcacta aatctagtag tactgaaatg gattttattt tcttccag gtt tat gga   1668
                                                        Val Tyr Gly
                                                                 90
cgt gac agt tct ctg ttc cag ccg ttc aat gtg cct tcc aat cga cct    1716
Arg Asp Ser Ser Leu Phe Gln Pro Phe Asn Val Pro Ser Asn Arg Pro
             95                 100                 105
ggc cat tct act gaa aag atc aat tca gat aag atc aac aag aag att    1764
Gly His Ser Thr Glu Lys Ile Asn Ser Asp Lys Ile Asn Lys Lys Ile
        110                 115                 120
agt ggt tca aga aaa gaa ctg ggg atg tta tcc tct cag act aag ggc    1812
Ser Gly Ser Arg Lys Glu Leu Gly Met Leu Ser Ser Gln Thr Lys Gly
    125                 130                 135
atg gat att tat gct tca aga tca act gct gag gca cca caa aga aga    1860
Met Asp Ile Tyr Ala Ser Arg Ser Thr Ala Glu Ala Pro Gln Arg Arg
140                 145                 150
gca gaa aat aca ata aag agt tct tcg gga aag aga ttg gcc gat gat    1908
Ala Glu Asn Thr Ile Lys Ser Ser Ser Gly Lys Arg Leu Ala Asp Asp
155                 160                 165                 170
gat gaa ttt atg gtt cct tct gtc ttc aat tcc aga ttt cct caa tat    1956
Asp Glu Phe Met Val Pro Ser Val Phe Asn Ser Arg Phe Pro Gln Tyr
            175                 180                 185
agt act caa gag aat gca ggg gtt caa gac caa tca aca ccc ctt gtt    2004
Ser Thr Gln Glu Asn Ala Gly Val Gln Asp Gln Ser Thr Pro Leu Val
        190                 195                 200
gct gca aat cca cac aaa agc cct tca aca gtg tcc aaa tca tcc aca    2052
Ala Ala Asn Pro His Lys Ser Pro Ser Thr Val Ser Lys Ser Ser Thr
    205                 210                 215
aag tgt tat aac act gtt agc aag aaa ttg gag aga atc cat gtt tct    2100
Lys Cys Tyr Asn Thr Val Ser Lys Lys Leu Glu Arg Ile His Val Ser
220                 225                 230
gat gtg aaa tca agg acc cct ttg aaa gac aag gag atg gaa gca gca    2148
Asp Val Lys Ser Arg Thr Pro Leu Lys Asp Lys Glu Met Glu Ala Ala
235                 240                 245                 250
cag aca tcc aaa aac gtg gaa gtt gaa aaa agt tca tcc ttt cat gct    2196
Gln Thr Ser Lys Asn Val Glu Val Glu Lys Ser Ser Ser Phe His Ala
            255                 260                 265
tcc aaa gat atg ttt gaa agc agg cat gct aaa gta tat cct aag atg    2244
Ser Lys Asp Met Phe Glu Ser Arg His Ala Lys Val Tyr Pro Lys Met
        270                 275                 280
gat aag acg ggc att ata aat gat tct gat gag cca cat ggt gga aat    2292
Asp Lys Thr Gly Ile Ile Asn Asp Ser Asp Glu Pro His Gly Gly Asn
    285                 290                 295
agt ggg cat caa gcg aca agc aga aat gga ggt tcc atg aaa ttt cag    2340
Ser Gly His Gln Ala Thr Ser Arg Asn Gly Gly Ser Met Lys Phe Gln
300                 305                 310
aac cct cca atg aga aga aat gaa att tcc tct aat cca tct tct gaa    2388
Asn Pro Pro Met Arg Arg Asn Glu Ile Ser Ser Asn Pro Ser Ser Glu
315                 320                 325                 330
aat act gat agg cat tat aat tta ccg caa gga ggc ata gag gaa aca    2436
Asn Thr Asp Arg His Tyr Asn Leu Pro Gln Gly Gly Ile Glu Glu Thr
            335                 340                 345
ggt aca aag aga aaa agg ttg cta gaa caa cac gat gca gag aaa agt    2484
Gly Thr Lys Arg Lys Arg Leu Leu Glu Gln His Asp Ala Glu Lys Ser
        350                 355                 360
gat gat gtg tca agg ttg cta gaa caa cac gat gca gag aac att gat    2532
Asp Asp Val Ser Arg Leu Leu Glu Gln His Asp Ala Glu Asn Ile Asp
    365                 370                 375
gat gtg tct gat tcc tcg gtg gag tgt ata act ggt tgg gag att tct    2580
Asp Val Ser Asp Ser Ser Val Glu Cys Ile Thr Gly Trp Glu Ile Ser
380                 385                 390
```

-continued

```
cca gat aaa att gtt gga gcc att ggt aca aag cat ttc tgg aaa gca      2628
Pro Asp Lys Ile Val Gly Ala Ile Gly Thr Lys His Phe Trp Lys Ala
395                 400                 405                 410
aga cgt gct att atg aa  gtaagtaaaa ctatccttt gagcttagtt              2675
Arg Arg Ala Ile Met Asn
                415
tggcccactc aaactagact tgtttgcagc tctaattacg tataggtagc tttgatgaat    2735
aaaatttgtt ttgtttccct tgctttactg ttatttgctc ttaatttgcg gttgatctta    2795
atcatcttag acagaaaaac atgatgacta tctcgtttgt ttttggttta tttcatattt    2855
gaatgccaat agatgtcagc tccagatgat atttcaaata cctcatgcat ggaaactgtg    2915
catacttatg ccaaattttg ggcttacaag tcagcatgtc tacaaatttc tttggcagaa    2975
ttaatatata tctagttcaa catttgctga tttgtaattg gattagttgt ctgcagaatg    3035
ccggcatgtt ttattttcct ttcaactagg tcaatcagtt ttgttgttgt ctgttgttct    3095
tgtccaccta cacctgtact actgaaatgt tctcttttgg agatgtcaat gaaaattta     3155
atctatagtg gtttcaattt tattttcatt ttagtcaaga agaatggcat aatctcattt    3215
aaaagattg taaagtgtc cctgttaaag tgatattgta ggtattgctt taccaagcta      3275
ctgtatgatt cccttattg ttttacactc taatcttctt taaactctat gcag t caa     3333
                                                              Gln
cag agg gtg ttt gct gtc cag gtt ttt gag ctg cat aag ttg gta aaa      3381
Gln Arg Val Phe Ala Val Gln Val Phe Glu Leu His Lys Leu Val Lys
            420                 425                 430
gtgagtctag caaatttctc ttccttctag ccactcttaa gcaggttaat tcgtggatag    3441
gattttgtcc ataatctgtt tataacccac acttgtattt gacttacaat cag gtg       3497
                                                             Val
cag aag ttg att gca gca tcg cca cat gta ctt att gaa agt gat cct      3545
Gln Lys Leu Ile Ala Ala Ser Pro His Val Leu Ile Glu Ser Asp Pro
435                 440                 445                 450
tgc ctt ggc aat gcc ttg ctt ggt agc aag aac aag ctg gtg gaa gaa      3593
Cys Leu Gly Asn Ala Leu Leu Gly Ser Lys Asn Lys Leu Val Glu Glu
                455                 460                 465
aac ctg aaa gca caa cct ctt tta gtc gca acc atc gat gac gtg gag      3641
Asn Leu Lys Ala Gln Pro Leu Leu Val Ala Thr Ile Asp Asp Val Glu
            470                 475                 480
cca agt cta cag caa ccg gag gta tca aaa gaa aac act gaa gac agc      3689
Pro Ser Leu Gln Gln Pro Glu Val Ser Lys Glu Asn Thr Glu Asp Ser
        485                 490                 495
cca ccc tcc cct cat gat act ggg ctt ggc agt ggt caa cgt gat caa      3737
Pro Pro Ser Pro His Asp Thr Gly Leu Gly Ser Gly Gln Arg Asp Gln
    500                 505                 510
gct gca aca aat ggc gtc tct aaa agc aat cgt cga gct aca cct gtt      3785
Ala Ala Thr Asn Gly Val Ser Lys Ser Asn Arg Arg Ala Thr Pro Val
515                 520                 525                 530
gct tct gat aac aaa caa aat aac tgg ggc gtt caa ctt caa cca cct      3833
Ala Ser Asp Asn Lys Gln Asn Asn Trp Gly Val Gln Leu Gln Pro Pro
                535                 540                 545
caa aat caa tgg ctt gtc cct gtc atg tct cct ttg gaa ggc ctt gtc      3881
Gln Asn Gln Trp Leu Val Pro Val Met Ser Pro Leu Glu Gly Leu Val
            550                 555                 560
tat aag cct tat tct ggt ccg tgc cct gct ggt agc ata ttg gcc          3929
Tyr Lys Pro Tyr Ser Gly Pro Cys Pro Pro Ala Gly Ser Ile Leu Ala
        565                 570                 575
ccg ttt tat gcc aac tgt act cct ttg agt ctt cca tca aca gct gga      3977
Pro Phe Tyr Ala Asn Cys Thr Pro Leu Ser Leu Pro Ser Thr Ala Gly
    580                 585                 590
gat ttc atg aac tcg gca tac ggt gtt cct atg cct cat cag cca caa      4025
Asp Phe Met Asn Ser Ala Tyr Gly Val Pro Met Pro His Gln Pro Gln
595                 600                 605                 610
cat atg ggt gct cct ggc cct cct tcc atg cct atg aac tac ttc ccg      4073
His Met Gly Ala Pro Gly Pro Pro Ser Met Pro Met Asn Tyr Phe Pro
                615                 620                 625
cct ttc agc ata cca gtg atg aac cca act gca ccg gca cct gta gtc      4121
Pro Phe Ser Ile Pro Val Met Asn Pro Thr Ala Pro Ala Pro Val Val
            630                 635                 640
gaa caa ggg aga cat cct tcg atg cca cag cct tat ggg aac ttt gag      4169
Glu Gln Gly Arg His Pro Ser Met Pro Gln Pro Tyr Gly Asn Phe Glu
        645                 650                 655
cag cag tcg tgg atc tca tgt aac atg tca cat cca agt ggc att tgg      4217
Gln Gln Ser Trp Ile Ser Cys Asn Met Ser His Pro Ser Gly Ile Trp
    660                 665                 670
aga ttt cat gcc tca aga gat agc gag gca cag gcc agc agc gct agc      4265
Arg Phe His Ala Ser Arg Asp Ser Glu Ala Gln Ala Ser Ser Ala Ser
675                 680                 685                 690
agt cct ttt gac agg ttc caa tgc agt gga agt ggt cct gta tcc gcc      4313
Ser Pro Phe Asp Arg Phe Gln Cys Ser Gly Ser Gly Pro Val Ser Ala
                695                 700                 705
ttc ccc aca gta tca gct cag aac aac cag cct cag ccc tca tat agc      4361
Phe Pro Thr Val Ser Ala Gln Asn Asn Gln Pro Gln Pro Ser Tyr Ser
            710                 715                 720
agc cgg gac aac cag acc aat gtt atc aag gtt gtt cca cat aat tca      4409
```

```
            Ser Arg Asp Asn Gln Thr Asn Val Ile Lys Val Pro His Asn Ser
                    725                 730                 735
            cga act gct tca gag tca gca gca cgg att ttc cgg tca ata caa atg    4457
            Arg Thr Ala Ser Glu Ser Ala Ala Arg Ile Phe Arg Ser Ile Gln Met
                    740                 745                 750
            gaa cgg caa cga gat gat tga                                         4478
            Glu Arg Gln Arg Asp Asp
            755                 760
```

<210> SEQ ID NO 27
<211> LENGTH: 760
<212> TYPE: PRT
<213> ORGANISM: Oryza sativa

<400> SEQUENCE: 27

```
            Met Ala Thr Arg Gly Gly Gly Gly Gly Gly Lys Glu Ala Lys
            1               5                   10                  15
            Gly Lys Val Met Gly Pro Leu Phe Pro Arg Leu His Val Asn Asp Ala
                            20                  25                  30
            Ala Lys Gly Gly Pro Arg Ala Pro Arg Asn Lys Met Ala Leu
                        35                  40                  45
            Tyr Glu Gln Phe Thr Val Pro Ser His Arg Phe Ser Gly Gly Gly
                50                  55                  60
            Gly Gly Gly Val Gly Gly Ser Pro Ala His Ser Thr Ser Ala Ala Ser
            65                  70                  75                  80
            Gln Ser Gln Ser Gln Ser Gln Val Tyr Gly Arg Asp Ser Ser Leu Phe
                            85                  90                  95
            Gln Pro Phe Asn Val Pro Ser Asn Arg Pro Gly His Ser Thr Glu Lys
                        100                 105                 110
            Ile Asn Ser Asp Lys Ile Asn Lys Lys Ile Ser Gly Ser Arg Lys Glu
                    115                 120                 125
            Leu Gly Met Leu Ser Ser Gln Thr Lys Gly Met Asp Ile Tyr Ala Ser
                130                 135                 140
            Arg Ser Thr Ala Glu Ala Pro Gln Arg Arg Ala Glu Asn Thr Ile Lys
            145                 150                 155                 160
            Ser Ser Ser Gly Lys Arg Leu Ala Asp Asp Glu Phe Met Val Pro
                            165                 170                 175
            Ser Val Phe Asn Ser Arg Phe Pro Gln Tyr Ser Thr Gln Glu Asn Ala
                        180                 185                 190
            Gly Val Gln Asp Gln Ser Thr Pro Leu Val Ala Ala Asn Pro His Lys
                    195                 200                 205
            Ser Pro Ser Thr Val Ser Lys Ser Ser Thr Lys Cys Tyr Asn Thr Val
                210                 215                 220
            Ser Lys Lys Leu Glu Arg Ile His Val Ser Asp Val Lys Ser Arg Thr
            225                 230                 235                 240
            Pro Leu Lys Asp Lys Glu Met Glu Ala Ala Gln Thr Ser Lys Asn Val
                            245                 250                 255
            Glu Val Glu Lys Ser Ser Ser Phe His Ala Ser Lys Asp Met Phe Glu
                        260                 265                 270
            Ser Arg His Ala Lys Val Tyr Pro Lys Met Asp Lys Thr Gly Ile Ile
                    275                 280                 285
            Asn Asp Ser Asp Glu Pro His Gly Gly Asn Ser Gly His Gln Ala Thr
                290                 295                 300
            Ser Arg Asn Gly Gly Ser Met Lys Phe Gln Asn Pro Pro Met Arg Arg
            305                 310                 315                 320
            Asn Glu Ile Ser Ser Asn Pro Ser Ser Glu Asn Thr Asp Arg His Tyr
                            325                 330                 335
            Asn Leu Pro Gln Gly Gly Ile Glu Glu Thr Gly Thr Lys Arg Lys Arg
                        340                 345                 350
            Leu Leu Glu Gln His Asp Ala Glu Lys Ser Asp Val Ser Arg Leu
                    355                 360                 365
            Leu Glu Gln His Asp Ala Glu Asn Ile Asp Asp Val Ser Asp Ser Ser
                370                 375                 380
            Val Glu Cys Ile Thr Gly Trp Glu Ile Ser Pro Asp Lys Ile Val Gly
            385                 390                 395                 400
            Ala Ile Gly Thr Lys His Phe Trp Lys Ala Arg Arg Ala Ile Met Asn
                            405                 410                 415
            Gln Gln Arg Val Phe Ala Val Gln Val Phe Glu Leu His Lys Leu Val
                        420                 425                 430
            Lys Val Gln Lys Leu Ile Ala Ala Ser Pro His Val Leu Ile Glu Ser
                    435                 440                 445
            Asp Pro Cys Leu Gly Asn Ala Leu Gly Ser Lys Asn Lys Leu Val
                450                 455                 460
            Glu Glu Asn Leu Lys Ala Gln Pro Leu Leu Val Ala Thr Ile Asp Asp
            465                 470                 475                 480
            Val Glu Pro Ser Leu Gln Gln Pro Glu Val Ser Lys Glu Asn Thr Glu
                            485                 490                 495
```

```
        Asp Ser Pro Pro Ser Pro His Asp Thr Gly Leu Gly Ser Gly Gln Arg
                    500                 505                 510
        Asp Gln Ala Ala Thr Asn Gly Val Ser Lys Ser Asn Arg Arg Ala Thr
                515                 520                 525
        Pro Val Ala Ser Asp Asn Lys Gln Asn Asn Trp Gly Val Gln Leu Gln
                530                 535                 540
        Pro Pro Gln Asn Gln Trp Leu Val Pro Val Met Ser Pro Leu Glu Gly
        545                 550                 555                 560
        Leu Val Tyr Lys Pro Tyr Ser Gly Pro Cys Pro Ala Gly Ser Ile
                        565                 570                 575
        Leu Ala Pro Phe Tyr Ala Asn Cys Thr Pro Leu Ser Leu Pro Ser Thr
                    580                 585                 590
        Ala Gly Asp Phe Met Asn Ser Ala Tyr Gly Val Pro Met Pro His Gln
                595                 600                 605
        Pro Gln His Met Gly Ala Pro Gly Pro Pro Ser Met Pro Met Asn Tyr
                610                 615                 620
        Phe Pro Pro Phe Ser Ile Pro Val Met Asn Pro Thr Ala Pro Ala Pro
        625                 630                 635                 640
        Val Val Glu Gln Gly Arg His Pro Ser Met Pro Gln Pro Tyr Gly Asn
                        645                 650                 655
        Phe Glu Gln Gln Ser Trp Ile Ser Cys Asn Met Ser His Pro Ser Gly
                    660                 665                 670
        Ile Trp Arg Phe His Ala Ser Arg Asp Ser Glu Ala Gln Ala Ser Ser
                    675                 680                 685
        Ala Ser Ser Pro Phe Asp Arg Phe Gln Cys Ser Gly Ser Gly Pro Val
                690                 695                 700
        Ser Ala Phe Pro Thr Val Ser Ala Gln Asn Asn Gln Pro Gln Pro
        705                 710                 715                 720
        Tyr Ser Ser Arg Asp Asn Gln Thr Asn Val Ile Lys Val Val Pro His
                        725                 730                 735
        Asn Ser Arg Thr Ala Ser Glu Ser Ala Ala Arg Ile Phe Arg Ser Ile
                    740                 745                 750
        Gln Met Glu Arg Gln Arg Asp Asp
                    755                 760

<210> SEQ ID NO 28
<211> LENGTH: 938
<212> TYPE: DNA
<213> ORGANISM: Zea mays

<400> SEQUENCE: 28
gacgtggagc aaaacgatga tctgtctgat tcctctgttg aatctttgcc tggaatggag     60
atttctccag atgatgttgt cagtgctatt ggtcccaagc attttggaa agcgagaaga    120
gctattgtca atcagcagag ggtatttgct gttcaagtat tcgagctgca taggttgatc    180
aaagtgcaga agttgatcgc tgcatctcca catgtactta ttgaggggga tccttgcctt    240
ggcaaatcct tggcggtgag cmagaaaagg ctgaagtcag tggctgattc ccgtwatgtc    300
cccgtttgaa ggacttgtct acaagcctta tcccgggsca ytgccctccg gtggaagtct    360
tttggcgccc ccattttttg ccagctaccc cacctcttcc tcctccacag ctggggggga    420
tttcatgagt tcggcatgtg gagccaggct gatgagtgcc cctgtgtact tcccgtctt    480
cagcatgcct gcagtgtcag ggtctgcagt tgagcaagtg agccatgttg cagcgtcgca    540
gcataaacgg aactcgtgta gtgaagcggt gttggcatca aggacagcg aggtgcaagg    600
cagtagtgct agcagtccgg catcttctga aacagcagct caacccaggg tcattagggt    660
tgttccccac acggcacgca cggcttcaga gtcggcagca aggattttcc gctcaataca    720
gatggagagg aaacaaaacg accccgtgact ggcagataaa aatgaaagaa cggaggggagt    780
agactaattt tttgaccgat aattataatg atcgccgtaa attggctggc ccgcccgcct    840
tatgttttt gttcagtgta aatatgctgt gtctgtcaga atgatatggc atctgtagct    900
attttggttc tgtcagaatc atgttgattg gaattaaa                           938

<210> SEQ ID NO 29
<211> LENGTH: 248
<212> TYPE: PRT
<213> ORGANISM: Zea mays
<220> FEATURE:
<221> NAME/KEY: UNSURE
<222> LOCATION: (88)..(88)
<223> OTHER INFORMATION:
<221> NAME/KEY: unsure
<222> LOCATION: (98)..(98)
<223> OTHER INFORMATION: amino acid not confirmed, based on nucleic acid sequence
<221> NAME/KEY: unsure
<222> LOCATION: (113)..(113)
<223> OTHER INFORMATION: amino acid not confirmed, based on nucleic acid sequence
<221> NAME/KEY: unsure
<222> LOCATION: (114)..(114)
<223> OTHER INFORMATION: amino acid not confirmed, based on nucleic acid sequence
```

```
<400> SEQUENCE: 29

Asp Val Glu Gln Asn Asp Asp Leu Ser Asp Ser Ser Val Glu Ser Leu
    1               5                   10                  15
    Pro Gly Met Glu Ile Ser Pro Asp Asp Val Val Ser Ala Ile Gly Pro
                    20                  25                  30
    Lys His Phe Trp Lys Ala Arg Arg Ala Ile Val Asn Gln Gln Arg Val
                35                  40                  45
    Phe Ala Val Gln Val Phe Glu Leu His Arg Leu Ile Lys Val Gln Lys
            50                  55                  60
    Leu Ile Ala Ala Ser Pro His Val Leu Ile Glu Gly Asp Pro Cys Leu
    65                  70                  75                  80
    Gly Lys Ser Leu Ala Val Ser Xaa Lys Arg Leu Ser Gln Trp Leu Ile
                    85                  90                  95
    Pro Xaa Met Ser Pro Phe Glu Gly Leu Val Tyr Lys Pro Tyr Pro Gly
                100                 105                 110
    Xaa Xaa Pro Ser Gly Gly Ser Leu Leu Ala Pro Pro Phe Phe Ala Ser
                115                 120                 125
    Tyr Pro Thr Ser Ser Ser Ser Thr Ala Gly Gly Asp Phe Met Ser Ser
                130                 135                 140
    Ala Cys Gly Ala Arg Leu Met Ser Ala Pro Val Tyr Phe Pro Ser Phe
    145                 150                 155                 160
    Ser Met Pro Ala Val Ser Gly Ser Ala Val Glu Gln Val Ser His Val
                    165                 170                 175
    Ala Ala Ser Gln His Lys Arg Asn Ser Cys Ser Glu Ala Val Leu Ala
                180                 185                 190
    Ser Arg Asp Ser Glu Val Gln Gly Ser Ser Ala Ser Ser Pro Ala Ser
                195                 200                 205
    Ser Glu Thr Ala Ala Gln Pro Arg Val Ile Arg Val Val Pro His Thr
                210                 215                 220
    Ala Arg Thr Ala Ser Glu Ser Ala Ala Arg Ile Phe Arg Ser Ile Gln
    225                 230                 235                 240
    Met Glu Arg Lys Gln Asn Asp Pro
                    245

<210> SEQ ID NO 30
<211> LENGTH: 625
<212> TYPE: DNA
<213> ORGANISM: Zea mays
<220> FEATURE:
<221> NAME/KEY: exon
<222> LOCATION: (1)..(570)
<223> OTHER INFORMATION:
<221> NAME/KEY: 3'UTR
<222> LOCATION: (571)..(625)
<223> OTHER INFORMATION:

<400> SEQUENCE: 30 gca cga ggg cac atg gtc cct cct ggc gcc cct gcc atg cat atg aac    48
    Ala Arg Gly His Met Val Pro Pro Gly Ala Pro Ala Met His Met Asn
    1               5                   10                  15
    tac ttc ccg cct ttc agt atg cca gtg atg aat cca gga aca cca gca    96
    Tyr Phe Pro Pro Phe Ser Met Pro Val Met Asn Pro Gly Thr Pro Ala
                    20                  25                  30
    tct gca gtg gag caa ggg agc cat gct gct gcg cca cag cct cat ggg   144
    Ser Ala Val Glu Gln Gly Ser His Ala Ala Ala Pro Gln Pro His Gly
                35                  40                  45
    cac atg gac cag cag tcg ctg atc tca tgt aac atg tca cac ccg agt   192
    His Met Asp Gln Gln Ser Leu Ile Ser Cys Asn Met Ser His Pro Ser
            50                  55                  60
    ggc gtt tgg agg ttt ctt gca tca agg gac agc gag cca cag gcc agc   240
    Gly Val Trp Arg Phe Leu Ala Ser Arg Asp Ser Glu Pro Gln Ala Ser
    65                  70                  75                  80
    agc gcc acc agc cct ttc gac agg ctc caa gtc caa ggt gat gga agt   288
    Ser Ala Thr Ser Pro Phe Asp Arg Leu Gln Val Gln Gly Asp Gly Ser
                    85                  90                  95
    gct ccg ttg tca ttc ttt ccc acg gct tca gct ccg aat gtc cag cct   336
    Ala Pro Leu Ser Phe Phe Pro Thr Ala Ser Ala Pro Asn Val Gln Pro
                100                 105                 110
    ccg ccc tca tct gga ggc cgg gac cgg gac cag cag aac cat gta atc   384
    Pro Pro Ser Ser Gly Gly Arg Asp Arg Asp Gln Gln Asn His Val Ile
                115                 120                 125
    agg gtt gtt ccg cgt aac gca cag act gct tca gtc ccg aaa gcc caa   432
    Arg Val Val Pro Arg Asn Ala Gln Thr Ala Ser Val Pro Lys Ala Gln
                130                 135                 140
    cct cag ccg tca tcc gga ggc cgg gac caa aag aac cat gta atc agg   480
    Pro Gln Pro Ser Ser Gly Gly Arg Asp Gln Lys Asn His Val Ile Arg
```

-continued

```
                145                 150                 155                 160
        gtt gtt ccg cat aac gcg cag act gct tcg gag tca gca gcg tgg atc       528
        Val Val Pro His Asn Ala Gln Thr Ala Ser Glu Ser Ala Ala Trp Ile
                                165                 170                 175
        ttc cgg tca ata caa atg gag agg aac caa aat gat tcg tag               570
        Phe Arg Ser Ile Gln Met Glu Arg Asn Gln Asn Asp Ser
                        180                 185 ctggttacca tatactttcg tgtcatccga tggcagctta gtgcagcatt gcagt           625
```

<210> SEQ ID NO 31
<211> LENGTH: 189
<212> TYPE: PRT
<213> ORGANISM: Zea mays

<400> SEQUENCE: 31

```
        Ala Arg Gly His Met Val Pro Pro Gly Ala Pro Ala Met His Met Asn
        1               5                   10                  15
        Tyr Phe Pro Pro Phe Ser Met Pro Val Met Asn Pro Gly Thr Pro Ala
                        20                  25                  30
        Ser Ala Val Glu Gln Gly Ser His Ala Ala Pro Gln Pro His Gly
                    35                  40                  45
        His Met Asp Gln Gln Ser Leu Ile Ser Cys Asn Met Ser His Pro Ser
                50                  55                  60
        Gly Val Trp Arg Phe Leu Ala Ser Arg Asp Ser Glu Pro Gln Ala Ser
        65                  70                  75                  80
        Ser Ala Thr Ser Pro Phe Asp Arg Leu Gln Val Gln Gly Asp Gly Ser
                        85                  90                  95
        Ala Pro Leu Ser Phe Phe Pro Thr Ala Ser Ala Pro Asn Val Gln Pro
                    100                 105                 110
        Pro Pro Ser Ser Gly Gly Arg Asp Arg Asp Gln Gln Asn His Val Ile
                115                 120                 125
        Arg Val Val Pro Arg Asn Ala Gln Thr Ala Ser Val Pro Lys Ala Gln
            130                 135                 140
        Pro Gln Pro Ser Ser Gly Gly Arg Asp Gln Lys Asn His Val Ile Arg
        145                 150                 155                 160
        Val Val Pro His Asn Ala Gln Thr Ala Ser Glu Ser Ala Ala Trp Ile
                        165                 170                 175
        Phe Arg Ser Ile Gln Met Glu Arg Asn Gln Asn Asp Ser
                    180                 185
```

<210> SEQ ID NO 32
<211> LENGTH: 2794
<212> TYPE: DNA
<213> ORGANISM: Arabidopsis thaliana
<220> FEATURE:
<221> NAME/KEY: 5'UTR
<222> LOCATION: (1)..(476)
<223> OTHER INFORMATION:
<221> NAME/KEY: exon
<222> LOCATION: (479)..(706)
<223> OTHER INFORMATION:
<221> NAME/KEY: Intron
<222> LOCATION: (707)..(833)
<223> OTHER INFORMATION:
<221> NAME/KEY: exon
<222> LOCATION: (834)..(1384)
<223> OTHER INFORMATION:
<221> NAME/KEY: Intron
<222> LOCATION: (1385)..(1471)
<223> OTHER INFORMATION:
<221> NAME/KEY: exon
<222> LOCATION: (1472)..(1523)
<223> OTHER INFORMATION:
<221> NAME/KEY: Intron
<222> LOCATION: (1524)..(1591)
<223> OTHER INFORMATION:
<221> NAME/KEY: exon
<222> LOCATION: (1592)..(2383)
<223> OTHER INFORMATION:
<221> NAME/KEY: 3'UTR
<222> LOCATION: (2384)..(2794)
<223> OTHER INFORMATION:

<400> SEQUENCE: 32

```
        taaaagaccg agtcacccga acatctccac cttcacgcca ttctcctacc actcggacct      60
```

-continued

```
aaccaaccaa taccttccac gtcatgtaca atccgagttc ccgtgagata gggatcttta      120
cttgaagcaa ccagacatga ccgcagagtc acacacacac acaccccctaa gcttttttgtc    180
gtccctcgt atggaatcca ttgtgggacg acacaaaaat atcttcttt gcttctctgc        240
tttcttcttc ttcttcttaa aatttgtttc tttcaggtgg atttgatctc catctacgta      300
aaacaaaaac aaagtttata atctttttgg attttgggat tgatctaaag tgagatttcg      360
atcttggcac taggttttgc aaggttacct aacaatttct ggttctgatt tcatttcttt      420
aggttacgtg taagggaagg aattgttaat agggtttgtt tgtgagcgta ggaaaaag        478
atg gga gga atg aaa gat gaa gca aag agg ata aca att cct cca ttg        526
Met Gly Gly Met Lys Asp Glu Ala Lys Arg Ile Thr Ile Pro Pro Leu
1               5                   10                  15
ttt cca agg gtt cat gtc aat gat act gga aga gga ggc ctg tct caa        574
Phe Pro Arg Val His Val Asn Asp Thr Gly Arg Gly Gly Leu Ser Gln
                20                  25                  30
caa ttt gat ggc aaa aca atg tct ctc gtc tct tct aaa cgt ccc aat        622
Gln Phe Asp Gly Lys Thr Met Ser Leu Val Ser Ser Lys Arg Pro Asn
        35                  40                  45
ctt cct tct ccg acc aac aac ata tct gat tct ctt tcc act ttc tct        670
Leu Pro Ser Pro Thr Asn Asn Ile Ser Asp Ser Leu Ser Thr Phe Ser
    50                  55                  60
ttg tct ctt cct cca cca cca aac aat gcc cgt ctc gtgagtcctt             716
Leu Ser Leu Pro Pro Pro Pro Asn Asn Ala Arg Leu
65                  70                  75
ttaattcact cattcaactt tcttggtttt gtgtgtctgc agatttatat acaagaatgg      776
tgacaatgca tatttagatt atcactttat gacttgttga atactttttt gtaacag        833
att gat gga cct gaa aag aat cag ttt tca cca atc tac aac aca aag        881
Ile Asp Gly Pro Glu Lys Asn Gln Phe Ser Pro Ile Tyr Asn Thr Lys
            80                  85                  90
ttt gag ggg aag ctg aat aaa aaa ggc ata aat tat aca agt cct aaa        929
Phe Glu Gly Lys Leu Asn Lys Lys Gly Ile Asn Tyr Thr Ser Pro Lys
        95                  100                 105
gga tca tca gtt act aat act aag cct agt tca ata aaa caa aat gag        977
Gly Ser Ser Val Thr Asn Thr Lys Pro Ser Ser Ile Lys Gln Asn Glu
    110                 115                 120
tac ctc aag aac ctt acc agc ttg gat tct att aag tct cct att gtt       1025
Tyr Leu Lys Asn Leu Thr Ser Leu Asp Ser Ile Lys Ser Pro Ile Val
125                 130                 135                 140
ata cac tca gaa ata gat cca caa gca aac aca gat ttg tca ctc caa       1073
Ile His Ser Glu Ile Asp Pro Gln Ala Asn Thr Asp Leu Ser Leu Gln
            145                 150                 155
ttt tgt act agc ggt agc agt aaa ccc gga gga gag gct gtt gtt ggt       1121
Phe Cys Thr Ser Gly Ser Ser Lys Pro Gly Gly Glu Ala Val Val Gly
        160                 165                 170
tct aag atc ctt ttg tca gaa cgt ttg gaa gat gaa aac cag aat ggg       1169
Ser Lys Ile Leu Leu Ser Glu Arg Leu Glu Asp Glu Asn Gln Asn Gly
    175                 180                 185
tct ccc aat gtg atg aaa act caa tca tat aga aga aac ttt gct gag       1217
Ser Pro Asn Val Met Lys Thr Gln Ser Tyr Arg Arg Asn Phe Ala Glu
190                 195                 200
ttt aac aat gaa act caa aag aag ccc aaa act ctg cct cgg cgt gaa       1265
Phe Asn Asn Glu Thr Gln Lys Lys Pro Lys Thr Leu Pro Arg Arg Glu
205                 210                 215                 220
caa gtt gct tca aac tgc tct gca ata gag tct ttg tct ggt ata agt       1313
Gln Val Ala Ser Asn Cys Ser Ala Ile Glu Ser Leu Ser Gly Ile Ser
            225                 230                 235
gca tct tct tat gat att gcc aga gtg att ggt gaa aag agg ttt tgg       1361
Ala Ser Ser Tyr Asp Ile Ala Arg Val Ile Gly Glu Lys Arg Phe Trp
        240                 245                 250
aag atg aga aca tat atg atc aa  gtttgtatcc tcctctcact tttcttatga      1414
Lys Met Arg Thr Tyr Met Ile Asn
    255
tcccaacttc ataacttc cgtatttctt actattttt attgttgata ttttcag t         1472
cag caa aag atc ttt gcc ggg caa gta ttt gag ctc cat aga ctg ata       1520
Gln Gln Lys Ile Phe Ala Gly Gln Val Phe Glu Leu His Arg Leu Ile
            265                 270                 275
atg gtaagcttt aataaccta ttgttctgg tttgctttct atgcttcaga               1573
Met
ttacttaata tgatgcag gtt caa aag atg gtt gcg aag tcg cca aac ttg       1624
                   Val Gln Lys Met Val Ala Lys Ser Pro Asn Leu
                                280                 285
ttt ctt gaa agt aag ctt aat ggt gtc aaa cat ggt aca atg agg tca       1672
Phe Leu Glu Ser Lys Leu Asn Gly Val Lys His Gly Thr Met Arg Ser
290                 295                 300
tca cat cag ctt gca atg gcg gct tca aag gtt aga aag cca aac act       1720
Ser His Gln Leu Ala Met Ala Ala Ser Lys Val Arg Lys Pro Asn Thr
305                 310                 315                 320
gag aat cac aaa cct gta cct gaa gaa tat cca gag cat atg aaa cca       1768
Glu Asn His Lys Pro Val Pro Glu Glu Tyr Pro Glu His Met Lys Pro
            325                 330                 335
aag ctt cct cta cct tcc ata agc aaa gaa ctc gtg act cct att tgg       1816
```

-continued

```
        Lys Leu Pro Leu Pro Ser Ile Ser Lys Glu Leu Val Thr Pro Ile Trp
                    340                 345                 350
        cca caa cag cta ctt cct cct cct gga aac caa tgg tta gtt cct gta        1864
        Pro Gln Gln Leu Leu Pro Pro Pro Gly Asn Gln Trp Leu Val Pro Val
                        355                 360                 365
        ata act gat tca gac ggt ctg gtc tat aaa cca ttt cca gga cca tgt        1912
        Ile Thr Asp Ser Asp Gly Leu Val Tyr Lys Pro Phe Pro Gly Pro Cys
        370                 375                 380
        cct cct tct tct tca gcc ttc atg gtt cca gtt tat ggc caa gat tca        1960
        Pro Pro Ser Ser Ser Ala Phe Met Val Pro Val Tyr Gly Gln Asp Ser
        385                 390                 395                 400
        ctc gag aca cca ttc agg ttc cct gtt tct tct cca ttc agc cac agc        2008
        Leu Glu Thr Pro Phe Arg Phe Pro Val Ser Ser Pro Phe Ser His Ser
                        405                 410                 415
        tac ttc cca cct cct aac gcg agg aca aca gtt gac caa aca aac ccg        2056
        Tyr Phe Pro Pro Pro Asn Ala Arg Thr Thr Val Asp Gln Thr Asn Pro
                        420                 425                 430
        ttt ggt cag ttt caa aga tgg tct aac aca tca agc cac atg aca caa        2104
        Phe Gly Gln Phe Gln Arg Trp Ser Asn Thr Ser Ser His Met Thr Gln
                    435                 440                 445
        gcc att cca ttt tct tta aag aag tct cag gaa tct aat gac agt gac        2152
        Ala Ile Pro Phe Ser Leu Lys Lys Ser Gln Glu Ser Asn Asp Ser Asp
        450                 455                 460
        ata cat gga agc aca gct tca agt cca cca gag aag cat aaa ctt gaa        2200
        Ile His Gly Ser Thr Ala Ser Ser Pro Pro Glu Lys His Lys Leu Glu
        465                 470                 475                 480
        gtg ctt cct ctg ttt cct aca gag cct acc cat caa act gat gag tac        2248
        Val Leu Pro Leu Phe Pro Thr Glu Pro Thr His Gln Thr Asp Glu Tyr
                        485                 490                 495
        aag cag aaa cag caa ccg atg ctt cgc gcc att aaa gcc gtt cct cat        2296
        Lys Gln Lys Gln Gln Pro Met Leu Arg Ala Ile Lys Ala Val Pro His
                    500                 505                 510
        aat tca aca tct gcc tct gaa tct gct gca agg atc ttc cgt ttc att        2344
        Asn Ser Thr Ser Ala Ser Glu Ser Ala Ala Arg Ile Phe Arg Phe Ile
                    515                 520                 525
        cag gaa gaa agg agg gac tca gat cat atg att agt tag ttcttttata        2393
        Gln Glu Glu Arg Arg Asp Ser Asp His Met Ile Ser
        530                 535                 540
        tttgaaaccc ttccacattc ttttgctctc attgcttctt catctagctt agattttcag     2453
        tatattctat ttactcttct tatgaagatg taaatcaaat actatcacta tacattaaac     2513
        atacacacac ttatacacac atcttacatt gttcttgtat tgacaaacag ctaataaaag     2573
        atagacttt  gtgcttctat tccagttttg aggagtttaa acattggaac aagaagagtt     2633
        ctttagccat tgaagtatct atattatcaa tgtggaagga gacaataagg atcagagttg     2693
        tgtccatgct atacgaagct acactcaagt tcaagaacat ttcagaacaa aaaccaagaa     2753
        caaaaagaag acaagagatc cattaattag aacccaagaa c                         2794
```

<210> SEQ ID NO 33
<211> LENGTH: 540
<212> TYPE: PRT
<213> ORGANISM: Arabidopsis thaliana

<400> SEQUENCE: 33

```
        Met Gly Gly Met Lys Asp Glu Ala Lys Arg Ile Thr Ile Pro Pro Leu
        1               5                   10                  15
        Phe Pro Arg Val His Val Asn Asp Thr Gly Arg Gly Gly Leu Ser Gln
                        20                  25                  30
        Gln Phe Asp Gly Lys Thr Met Ser Leu Val Ser Ser Lys Arg Pro Asn
                    35                  40                  45
        Leu Pro Ser Pro Thr Asn Asn Ile Ser Asp Ser Leu Ser Thr Phe Ser
            50                  55                  60
        Leu Ser Leu Pro Pro Pro Asn Asn Ala Arg Leu Ile Asp Gly Pro
        65                  70                  75                  80
        Glu Lys Asn Gln Phe Ser Pro Ile Tyr Asn Thr Lys Phe Glu Gly Lys
                        85                  90                  95
        Leu Asn Lys Lys Gly Ile Asn Tyr Thr Ser Pro Lys Gly Ser Ser Val
                    100                 105                 110
        Thr Asn Thr Lys Pro Ser Ser Ile Ser Lys Gln Asn Glu Tyr Leu Lys Asn
                115                 120                 125
        Leu Thr Ser Leu Asp Ser Ile Lys Ser Pro Ile Val Ile His Ser Glu
            130                 135                 140
        Ile Asp Pro Gln Ala Asn Thr Asp Leu Ser Leu Gln Phe Cys Thr Ser
        145                 150                 155                 160
        Gly Ser Ser Lys Pro Gly Gly Glu Ala Val Val Gly Ser Lys Ile Leu
                        165                 170                 175
        Leu Ser Glu Arg Leu Glu Asp Glu Asn Gln Asn Gly Ser Pro Asn Val
                    180                 185                 190
        Met Lys Thr Gln Ser Tyr Arg Arg Asn Phe Ala Glu Phe Asn Asn Glu
```

```
            195                 200                 205
    Thr Gln Lys Lys Pro Lys Thr Leu Pro Arg Arg Glu Gln Val Ala Ser
        210                 215                 220
    Asn Cys Ser Ala Ile Glu Ser Leu Ser Gly Ile Ser Ala Ser Ser Tyr
    225                 230                 235                 240
    Asp Ile Ala Arg Val Ile Gly Glu Lys Arg Phe Trp Lys Met Arg Thr
                    245                 250                 255
    Tyr Met Ile Asn Gln Gln Lys Ile Phe Ala Gly Gln Val Phe Glu Leu
                    260                 265                 270
    His Arg Leu Ile Met Val Gln Lys Met Val Ala Lys Ser Pro Asn Leu
                275                 280                 285
    Phe Leu Glu Ser Lys Leu Asn Gly Val Lys His Gly Thr Met Arg Ser
            290                 295                 300
    Ser His Gln Leu Ala Met Ala Ala Ser Lys Val Arg Lys Pro Asn Thr
    305                 310                 315                 320
    Glu Asn His Lys Pro Val Pro Glu Glu Tyr Pro Glu His Met Lys Pro
                    325                 330                 335
    Lys Leu Pro Leu Pro Ser Ile Ser Lys Glu Leu Val Thr Pro Ile Trp
                    340                 345                 350
    Pro Gln Gln Leu Leu Pro Pro Gly Asn Gln Trp Leu Val Pro Val
                355                 360                 365
    Ile Thr Asp Ser Asp Gly Leu Val Tyr Lys Pro Phe Pro Gly Pro Cys
            370                 375                 380
    Pro Pro Ser Ser Ser Ala Phe Met Val Pro Val Tyr Gly Gln Asp Ser
    385                 390                 395                 400
    Leu Glu Thr Pro Phe Arg Phe Pro Val Ser Ser Pro Phe Ser His Ser
                    405                 410                 415
    Tyr Phe Pro Pro Asn Ala Arg Thr Thr Val Asp Gln Thr Asn Pro
                    420                 425                 430
    Phe Gly Gln Phe Gln Arg Trp Ser Asn Thr Ser Ser His Met Thr Gln
                435                 440                 445
    Ala Ile Pro Phe Ser Leu Lys Lys Ser Gln Glu Ser Asn Asp Ser Asp
            450                 455                 460
    Ile His Gly Ser Thr Ala Ser Ser Pro Pro Glu Lys His Lys Leu Glu
    465                 470                 475                 480
    Val Leu Pro Leu Phe Pro Thr Glu Pro Thr His Gln Thr Asp Glu Tyr
                    485                 490                 495
    Lys Gln Lys Gln Gln Pro Met Leu Arg Ala Ile Lys Ala Val Pro His
                500                 505                 510
    Asn Ser Thr Ser Ala Ser Glu Ser Ala Ala Arg Ile Phe Arg Phe Ile
            515                 520                 525
    Gln Glu Glu Arg Arg Asp Ser Asp His Met Ile Ser
            530                 535                 540

<210> SEQ ID NO 34
<211> LENGTH: 4221
<212> TYPE: DNA
<213> ORGANISM: Arabidopsis thaliana
<220> FEATURE:
<221> NAME/KEY: 5'UTR
<222> LOCATION: (1)..(425)
<223> OTHER INFORMATION:
<221> NAME/KEY: exon
<222> LOCATION: (426)..(644)
<223> OTHER INFORMATION:
<221> NAME/KEY: Intron
<222> LOCATION: (645)..(1006)
<223> OTHER INFORMATION:
<221> NAME/KEY: exon
<222> LOCATION: (1007)..(1803)
<223> OTHER INFORMATION:
<221> NAME/KEY: Intron
<222> LOCATION: (1804)..(2983)
<223> OTHER INFORMATION:
<221> NAME/KEY: exon
<222> LOCATION: (2984)..(3035)
<223> OTHER INFORMATION:
<221> NAME/KEY: Intron
<222> LOCATION: (3036)..(3125)
<223> OTHER INFORMATION:
<221> NAME/KEY: exon
<222> LOCATION: (3126)..(4145)
<223> OTHER INFORMATION:
<221> NAME/KEY: 3'UTR
<222> LOCATION: (4146)..(4221)
<223> OTHER INFORMATION:

<400> SEQUENCE: 34
```

```
tatctttggg ggctccactt ttcctatctc tttttgcccc tttcctctct ctgttcacaa      60
gtcatcttct tccttcctct gaatcttgtt cctttttgct ctctctactt gattcaccca     120
ctctgtttct cgattagtac gttgaaaact cacttkggtt ttgtttgatt cctctttagt     180
ctgtttttcg atttcgtttt ctctgattgg tttggtggtg agatctctat cgtagtttgt     240
cctttgggtt aagatatttc atttgattgg tgggtttgtt ttattgaagc ttattgttgt     300
gaaagttgga gtctttctca gtttttaggt tgaattatta agagaaaggg aagattttg      360
gtgtgaagtt aggttatttg gggtttgaga agtttgcaag tgaaaaaggt tgtgaattgt     420
gagtg atg aag aga ggg aaa gat gag gag aag ata ttg gaa cct atg ttt    470
      Met Lys Arg Gly Lys Asp Glu Glu Lys Ile Leu Glu Pro Met Phe
        1               5                  10                  15
cct cgg ctt cat gtg aat gat gca gat aaa gga ggg cct aga gct cct        518
Pro Arg Leu His Val Asn Asp Ala Asp Lys Gly Gly Pro Arg Ala Pro
                 20                  25                  30
cct aga aac aag atg gct ctt tat gag cag ctt agt att cct tct cag        566
Pro Arg Asn Lys Met Ala Leu Tyr Glu Gln Leu Ser Ile Pro Ser Gln
             35                  40                  45
agg ttt ggt gat cat gga acg atg aat tct cgt agt aac aac aca agc        614
Arg Phe Gly Asp His Gly Thr Met Asn Ser Arg Ser Asn Asn Thr Ser
         50                  55                  60
act ttg gtt cat cct gga cca tct agt cag gtattgtttt gattttgatc          664
Thr Leu Val His Pro Gly Pro Ser Ser Gln
     65                  70
attgtatagg ctcttgatgt tattagttgt atgagtttgg atgttatata gcctgaaaga     724
gaaagtagga cattggttga tctatgtttc aattgttatc agatcatagt atcttctttt     784
tgcttatgga ttgagctttt aggattgaat tctcctgtat atatgagagt cttgtagaca     844
caagtttatc taagtgtggt ttatttctta aaactaacat tcttgttgtg cctgattctt     904
tttatgttct gaagttcgat gaaagtttct tgtgattgcc ctgagcattc agactattgc     964
aaggacatga gaaataatcc ttttttaccc tcttcaatgc ag cct tgt ggt gtg       1018
                                              Pro Cys Gly Val
                                                            75
gaa aga aac tta tct gtc cag cat ctt gat tct tca gcc gca aac caa       1066
Glu Arg Asn Leu Ser Val Gln His Leu Asp Ser Ser Ala Ala Asn Gln
                 80                  85                  90
gca act gag aag ttt gtc tcc caa atg tcc ttc atg gaa aat gtg aga       1114
Ala Thr Glu Lys Phe Val Ser Gln Met Ser Phe Met Glu Asn Val Arg
             95                 100                 105
tct tcg gca cag cat gat cag agg aaa atg gtg aga gag gaa gaa gat       1162
Ser Ser Ala Gln His Asp Gln Arg Lys Met Val Arg Glu Glu Glu Asp
110                 115                 120                 125
ttt gca gtt cca gta tat att aac tca aga aga tct cag tct cat ggc       1210
Phe Ala Val Pro Val Tyr Ile Asn Ser Arg Arg Ser Gln Ser His Gly
                 130                 135                 140
aga acc aag agt ggt att gag aag gaa aaa cac acc cca atg gtg gca       1258
Arg Thr Lys Ser Gly Ile Glu Lys Glu Lys His Thr Pro Met Val Ala
             145                 150                 155
cct agc tct cat cac tcc att cga ttt caa gaa gtg aat cag aca ggc       1306
Pro Ser Ser His His Ser Ile Arg Phe Gln Glu Val Asn Gln Thr Gly
         160                 165                 170
tca aag caa aac gta tgt ttg gct act tgt tca aaa cct gaa gtt agg       1354
Ser Lys Gln Asn Val Cys Leu Ala Thr Cys Ser Lys Pro Glu Val Arg
175                 180                 185
gat cag gtc aag gcg aat gca agg tca ggt ggc ttt gta atc tct tta       1402
Asp Gln Val Lys Ala Asn Ala Arg Ser Gly Gly Phe Val Ile Ser Leu
190                 195                 200                 205
gat gta tca gtc aca gag gag att gat ctc gaa aaa tca gca tca agt       1450
Asp Val Ser Val Thr Glu Glu Ile Asp Leu Glu Lys Ser Ala Ser Ser
                 210                 215                 220
cat gat aga gta aat gat tat aat gct tcc ttg aga caa gag tct aga       1498
His Asp Arg Val Asn Asp Tyr Asn Ala Ser Leu Arg Gln Glu Ser Arg
             225                 230                 235
aat cgg tta tac cga gat ggt ggc aaa act cgt ctg aag gac act gat       1546
Asn Arg Leu Tyr Arg Asp Gly Gly Lys Thr Arg Leu Lys Asp Thr Asp
         240                 245                 250
aat gga gct gaa tct cac ttg gca acg gaa aat cat caa gag ggt           1594
Asn Gly Ala Glu Ser His Leu Ala Thr Glu Asn His Ser Gln Glu Gly
     255                 260                 265
cat ggc agt cct gaa gac att gat aat gat cgt gaa tac agc aaa agc       1642
His Gly Ser Pro Glu Asp Ile Asp Asn Asp Arg Glu Tyr Ser Lys Ser
270                 275                 280                 285
aga gca tgc gcc tct ctg cag cag ata aat gaa gag gca agt gat gac       1690
Arg Ala Cys Ala Ser Leu Gln Gln Ile Asn Glu Glu Ala Ser Asp Asp
                 290                 295                 300
gtt tct gat gat tcg atg gtg gat tct ata tcc agc ata gat gtc tct       1738
Val Ser Asp Asp Ser Met Val Asp Ser Ile Ser Ser Ile Asp Val Ser
             305                 310                 315
ccc gat gat gtt gtg ggt ata tta ggt caa aaa cgt ttc tgg aga gca       1786
Pro Asp Asp Val Val Gly Ile Leu Gly Gln Lys Arg Phe Trp Arg Ala
         320                 325                 330
```

-continued

```
agg aaa gcc att gcc aa  gtaagttcac tagaaattta cagtttggtt        1833
Arg Lys Ala Ile Ala Asn
            335
atttattctc cgctctttct atttatctcc ttctttgata ccaacatttt ttgcttgaaa 1893
gaagttaata tttaagcatt gttccgtagt cttactgaag cttttcctc tgttgttttt  1953
tgctatttc attgaggact gtggtagggc atatttcact atcaccaaat ttcaaatttc  2013
tagaacactc tccttcatat tttttttcat gattaatgct gcaattgatt gctgatatac  2073
atatatgact ataactcagt ttcatattct gtctcatttt gggagaaaga gatttcagt   2133
ttatgcttga gaagtgatgg ttctatagtt gagaggcccc tgattcatct aaaatggtcc  2193
tattatgtgt ttagttgtag agtcctcggt agaatattaa cgcgtttaac acgttggatc  2253
atgttatagc agggagggac attctctgtt gacctatatt gtgcaaggtg cccgccgatg  2313
gctttattac tataccttct ttgcatctgg ttgttggaac atgtccctgt ctcggtttgg  2373
tattgctttt attctgcact gtcgtcttgg gcattttccc tacttgtcat tcaaggggtt  2433
gaaccaggta gggaaatgtt tttccgagga ccccaggatc taaattttag ttaaccatac  2493
gtaaagttag ttttgagtct tatgacgatg cagaattata gtttcttctt actactgctt  2553
aagaggatcc ttagtgtggt tgtgaactac agagttttta tgattgtagg cttcatgact  2613
taacttttaa ggttcaatgt actctaatcc atatggtaag gtatcggatt cacgaccaat  2673
gcaaataata agattttat ttcttgcttc ttgttaaata tctgacatct cattttgcag   2733
aggataagct gcgctgtaag ctagatttca ataagcccgt cctttgcatt gttatctatg  2793
ctttaatatg tcattggacc cattgatttg gttttcttct atctttttg attggctatg   2853
tattcttgtt tcttttttcc tatctcattt cgatcgtatt gttccattag ctgttcaacc  2913
taaactatgt ctctctttgt tgaacttttg atggataatc ttcttaatgt gactctgttt  2973
ctcattacag t caa caa aga gta ttt gct gtt caa cta ttt gag ttg cac  3023
              Gln Gln Arg Val Phe Ala Val Gln Leu Phe Glu Leu His
                  340                 345                 350
aga ctg att aag gtaaagtcat tcagaaactt ctcatatgtt tccatgagta        3075
Arg Leu Ile Lys
            355
tttgtttctt ctcgagctga aacaaacctc ttcaactgtg taataatcag gtt caa    3131
                                                        Val Gln
aaa ctt att gct gca tca ccg gat ctc ttg ctc gat gag atc agt ttt    3179
Lys Leu Ile Ala Ala Ser Pro Asp Leu Leu Leu Asp Glu Ile Ser Phe
    360                 365                 370
ctt gga aaa gtt tct gct aaa agc tat cca gtg aag aag ctc ctt cca    3227
Leu Gly Lys Val Ser Ala Lys Ser Tyr Pro Val Lys Lys Leu Leu Pro
375                 380                 385                 390
tca gaa ttt ctg gta aag cct cct cta cca cat gtt gtc gtc aaa caa    3275
Ser Glu Phe Leu Val Lys Pro Pro Leu Pro His Val Val Val Lys Gln
                395                 400                 405
agg ggt gac tcg gag aag act gac caa cat aaa atg gaa agc tca gct    3323
Arg Gly Asp Ser Glu Lys Thr Asp Gln His Lys Met Glu Ser Ser Ala
            410                 415                 420
gag aac gta gtt ggg agg ttg tca aat caa ggt cat cat caa caa tcc    3371
Glu Asn Val Val Gly Arg Leu Ser Asn Gln Gly His His Gln Gln Ser
        425                 430                 435
aac tac atg cct ttt gca aac aac cca ccg gct tca ccg gct cca aat    3419
Asn Tyr Met Pro Phe Ala Asn Asn Pro Pro Ala Ser Pro Ala Pro Asn
    440                 445                 450
gga tat tgc ttt cct cct cag cct cct cct tca gga aat cat cag caa    3467
Gly Tyr Cys Phe Pro Pro Gln Pro Pro Pro Ser Gly Asn His Gln Gln
455                 460                 465                 470
tgg ttg atc cct gta atg tct ccc tcg gaa gga ctg ata tac aag cct    3515
Trp Leu Ile Pro Val Met Ser Pro Ser Glu Gly Leu Ile Tyr Lys Pro
                475                 480                 485
cac cca ggt atg gca cac acg ggg cat tat gga gga tat tat ggt cat    3563
His Pro Gly Met Ala His Thr Gly His Tyr Gly Gly Tyr Tyr Gly His
            490                 495                 500
tat atg cct aca cca atg gta atg cct caa tat cac ccc ggc atg gga    3611
Tyr Met Pro Thr Pro Met Val Met Pro Gln Tyr His Pro Gly Met Gly
        505                 510                 515
ttc cca cct cct ggt aat ggc tac ttc cct cca tat gga atg atg ccc    3659
Phe Pro Pro Pro Gly Asn Gly Tyr Phe Pro Pro Tyr Gly Met Met Pro
    520                 525                 530
acc ata atg aac cca tat tgt tca agc caa caa caa caa caa caa caa    3707
Thr Ile Met Asn Pro Tyr Cys Ser Ser Gln Gln Gln Gln Gln Gln Gln
535                 540                 545                 550
ccc aat gag caa atg aac cag ttt gga cat cct gga aat ctt cag aac    3755
Pro Asn Glu Gln Met Asn Gln Phe Gly His Pro Gly Asn Leu Gln Asn
                555                 560                 565
acc caa caa caa caa cag aga tct gat aat gaa cct gct cca caa caa    3803
Thr Gln Gln Gln Gln Gln Arg Ser Asp Asn Glu Pro Ala Pro Gln Gln
            570                 575                 580
cag caa cag cca aca aag tct tat ccg cga gca aga aag agc agg caa    3851
Gln Gln Gln Pro Thr Lys Ser Tyr Pro Arg Ala Arg Lys Ser Arg Gln
        585                 590                 595
ggg agc aca gga agc agt cca agt ggg cca cag gga atc tct ggt agc    3899
Gly Ser Thr Gly Ser Ser Pro Ser Gly Pro Gln Gly Ile Ser Gly Ser
    600                 605                 610
aag tcc ttt cgg cca ttc gca gcc gtt gat gag gac agc aac atc aac    3947
```

```
        Lys Ser Phe Arg Pro Phe Ala Ala Val Asp Glu Asp Ser Asn Ile Asn
        615                 620                 625                 630
        aat gca cct gag caa acg atg aca aca acc aca acg aca aga aca          3995
        Asn Ala Pro Glu Gln Thr Met Thr Thr Thr Thr Thr Thr Arg Thr
                        635                 640                 645
        act gtt act cag aca aca aga gat ggg gga gga gtg acg aga gtg ata      4043
        Thr Val Thr Gln Thr Thr Arg Asp Gly Gly Gly Val Thr Arg Val Ile
                            650                 655                 660
        aag gtg gta cct cac aac gca aag ctc gcg agt gag aat gct gcc aga      4091
        Lys Val Val Pro His Asn Ala Lys Leu Ala Ser Glu Asn Ala Ala Arg
                        665                 670                 675
        att ttc cag tca ata caa gaa gaa cgt aaa cgc tat gac tcc tct aag      4139
        Ile Phe Gln Ser Ile Gln Glu Glu Arg Lys Arg Tyr Asp Ser Ser Lys
                        680                 685                 690
        cct taa tcctctctat gcgtattgta cttgatatgt attttacaaa attagaaaaa      4195
        Pro
        695
        ttgtgataga tgttatcctc aatata                                         4221

<210> SEQ ID NO 35
<211> LENGTH: 695
<212> TYPE: PRT
<213> ORGANISM: Arabidopsis thaliana

<400> SEQUENCE: 35

Met Lys Arg Gly Lys Asp Glu Glu Lys Ile Leu Glu Pro Met Phe Pro
    1               5                   10                  15
    Arg Leu His Val Asn Asp Ala Asp Lys Gly Gly Pro Arg Ala Pro Pro
                    20                  25                  30
    Arg Asn Lys Met Ala Leu Tyr Glu Gln Leu Ser Ile Pro Ser Gln Arg
                35                  40                  45
    Phe Gly Asp His Gly Thr Met Asn Ser Arg Ser Asn Asn Thr Ser Thr
            50                  55                  60
    Leu Val His Pro Gly Pro Ser Ser Gln Pro Cys Gly Val Glu Arg Asn
    65                  70                  75                  80
    Leu Ser Val Gln His Leu Asp Ser Ser Ala Ala Asn Gln Ala Thr Glu
                    85                  90                  95
    Lys Phe Val Ser Gln Met Ser Phe Met Glu Asn Val Arg Ser Ser Ala
                100                 105                 110
    Gln His Asp Gln Arg Lys Met Val Arg Glu Glu Asp Phe Ala Val
                115                 120                 125
    Pro Val Tyr Ile Asn Ser Arg Arg Ser Gln Ser His Gly Arg Thr Lys
    130                 135                 140
    Ser Gly Ile Glu Lys Glu Lys His Thr Pro Met Val Ala Pro Ser Ser
    145                 150                 155                 160
    His His Ser Ile Arg Phe Gln Glu Val Asn Gln Thr Gly Ser Lys Gln
                    165                 170                 175
    Asn Val Cys Leu Ala Thr Cys Ser Lys Pro Glu Val Arg Asp Gln Val
                180                 185                 190
    Lys Ala Asn Ala Arg Ser Gly Gly Phe Val Ile Ser Leu Asp Val Ser
                195                 200                 205
    Val Thr Glu Glu Ile Asp Leu Glu Lys Ser Ala Ser Ser His Asp Arg
                210                 215                 220
    Val Asn Asp Tyr Asn Ala Ser Leu Arg Gln Glu Ser Arg Asn Arg Leu
    225                 230                 235                 240
    Tyr Arg Asp Gly Gly Lys Thr Arg Leu Lys Asp Thr Asp Asn Gly Ala
                    245                 250                 255
    Glu Ser His Leu Ala Thr Glu Asn His Ser Gln Gly His Gly Ser
                260                 265                 270
    Pro Glu Asp Ile Asp Asn Asp Arg Glu Tyr Ser Lys Ser Arg Ala Cys
                275                 280                 285
    Ala Ser Leu Gln Gln Ile Asn Glu Gly Ala Ser Asp Asp Val Ser Asp
    290                 295                 300
    Asp Ser Met Val Asp Ser Ile Ser Ile Asp Val Ser Pro Asp Asp
    305                 310                 315                 320
    Val Val Gly Ile Leu Gly Gln Lys Arg Phe Trp Arg Ala Arg Lys Ala
                    325                 330                 335
    Ile Ala Asn Gln Gln Arg Val Phe Ala Val Gln Leu Phe Glu Leu His
                340                 345                 350
    Arg Leu Ile Lys Val Gln Lys Leu Ile Ala Ser Pro Asp Leu Leu
                355                 360                 365
    Leu Asp Glu Ile Ser Phe Leu Gly Lys Val Ser Ala Lys Ser Tyr Pro
            370                 375                 380
    Val Lys Lys Leu Leu Pro Ser Glu Phe Leu Val Lys Pro Pro Leu Pro
    385                 390                 395                 400
    His Val Val Val Lys Gln Arg Gly Asp Ser Glu Lys Thr Asp Gln His
                    405                 410                 415
```

```
            Lys Met Glu Ser Ser Ala Glu Asn Val Val Gly Arg Leu Ser Asn Gln
                        420                 425                 430
            Gly His His Gln Gln Ser Asn Tyr Met Pro Phe Ala Asn Asn Pro Pro
                    435                 440                 445
            Ala Ser Pro Ala Pro Asn Gly Tyr Cys Phe Pro Pro Gln Pro Pro Pro
                450                 455                 460
            Ser Gly Asn His Gln Gln Trp Leu Ile Pro Val Met Ser Pro Ser Glu
            465                 470                 475                 480
            Gly Leu Ile Tyr Lys Pro His Pro Gly Met Ala His Thr Gly His Tyr
                            485                 490                 495
            Gly Gly Tyr Tyr Gly His Tyr Met Pro Thr Pro Met Val Met Pro Gln
                        500                 505                 510
            Tyr His Pro Gly Met Gly Phe Pro Pro Pro Gly Asn Gly Tyr Phe Pro
                    515                 520                 525
            Pro Tyr Gly Met Met Pro Thr Ile Met Asn Pro Tyr Cys Ser Ser Gln
                530                 535                 540
            Gln Gln Gln Gln Gln Pro Asn Glu Gln Met Asn Gln Phe Gly His
            545                 550                 555                 560
            Pro Gly Asn Leu Gln Asn Thr Gln Gln Gln Gln Arg Ser Asp Asn
                            565                 570                 575
            Glu Pro Ala Pro Gln Gln Gln Gln Pro Thr Lys Ser Tyr Pro Arg
                        580                 585                 590
            Ala Arg Lys Ser Arg Gln Gly Ser Thr Gly Ser Ser Pro Gly Pro
                    595                 600                 605
            Gln Gly Ile Ser Gly Ser Lys Ser Phe Arg Pro Phe Ala Ala Val Asp
                610                 615                 620
            Glu Asp Ser Asn Ile Asn Asn Ala Pro Glu Gln Thr Met Thr Thr Thr
            625                 630                 635                 640
            Thr Thr Thr Thr Arg Thr Val Thr Gln Thr Thr Arg Asp Gly Gly
                            645                 650                 655
            Gly Val Thr Arg Val Ile Lys Val Val Pro His Asn Ala Lys Leu Ala
                        660                 665                 670
            Ser Glu Asn Ala Ala Arg Ile Phe Gln Ser Ile Gln Glu Glu Arg Lys
                    675                 680                 685
            Arg Tyr Asp Ser Ser Lys Pro
                690                 695

<210> SEQ ID NO 36
<211> LENGTH: 510
<212> TYPE: DNA
<213> ORGANISM: Medicago truncatula
<220> FEATURE:
<221> NAME/KEY: exon
<222> LOCATION: (383)..(508)
<223> OTHER INFORMATION:
<221> NAME/KEY: 5'UTR
<222> LOCATION: (1)..(382)
<223> OTHER INFORMATION:
<221> NAME/KEY: misc_feature
<222> LOCATION: (414)..(414)
<223> OTHER INFORMATION: n = any nucleic acid
<221> NAME/KEY: misc_feature
<222> LOCATION: (427)..(427)
<223> OTHER INFORMATION: n = any nucleic acid

<400> SEQUENCE: 36
atccctaaac accctttctc tctaatccct aattttctc ctatctttct cttacaattt      60
     gatttccttc ccatcataac cccttttttg ctccgaattt ctcgttttt tgtttaaacc     120
     aatttcctcc atcgatttg ataaatttt ttaatactac aaactataag caagatcaag     180
     tatgaatttt atgtttttct gatacccagt tgggaaaagt ttagattttg tgaattagtt     240
     gtgttaatta gtgattagta tagttctgtg tatatgctat aatcactttt tatttttgg     300
     agttcaggat tataaactga ttctgttctt tgagtgtaat tattgatttg gttgatccat     360
     agctgtatta ggaaggttaa gg atg aag aga ggg aat gat gat gag aaa gtg      412
                               Met Lys Arg Gly Asn Asp Asp Glu Lys Val
                                1               5                   10
     ang ggg ccg tta ttn cct agg tta cat gtt ggt gat aca gag aag gga       460
     Xaa Gly Pro Leu Xaa Pro Arg Leu His Val Gly Asp Thr Glu Lys Gly
                    15                  20                  25
     ggg cca aga gca cct cct agg aat aaa ttg gct ctc tat gag caa ttt       508
     Gly Pro Arg Ala Pro Pro Arg Asn Lys Leu Ala Leu Tyr Glu Gln Phe
                30                  35                  40
     aa                                                                   510

<210> SEQ ID NO 37
<211> LENGTH: 42
<212> TYPE: PRT
```

```
<213> ORGANISM: Medicago truncatula
<220> FEATURE:
<221> NAME/KEY: misc_feature
<222> LOCATION: (11)..(11)
<223> OTHER INFORMATION: Xaa = uncertain amino acid residue

<400> SEQUENCE: 37

Met Lys Arg Gly Asn Asp Asp Glu Lys Val Xaa Gly Pro Leu Phe Pro
    1               5                   10                  15
    Arg Leu His Val Gly Asp Thr Glu Lys Gly Gly Pro Arg Ala Pro Pro
                20                  25                  30
    Arg Asn Lys Leu Ala Leu Tyr Glu Gln Phe
                35                  40

<210> SEQ ID NO 38
<211> LENGTH: 652
<212> TYPE: DNA
<213> ORGANISM: Medicago truncatula
<220> FEATURE:
<221> NAME/KEY: exon
<222> LOCATION: (2)..(106)
<223> OTHER INFORMATION:
<221> NAME/KEY: misc_feature
<222> LOCATION: (7)..(7)
<223> OTHER INFORMATION: n = any nucleic acid
<221> NAME/KEY: 3'UTR
<222> LOCATION: (107)..(652)
<223> OTHER INFORMATION:

<400> SEQUENCE: 38 c cga gtn atc aaa gtg gtg cct cat aac cga aga tcg gca act gaa tct        49
      Arg Val Ile Lys Val Val Pro His Asn Arg Arg Ser Ala Thr Glu Ser
      1               5                   10                  15
    gca gct aga att ttc caa tca att caa gaa gag aga aaa caa tat gac          97
    Ala Ala Arg Ile Phe Gln Ser Ile Gln Glu Glu Arg Lys Gln Tyr Asp
                    20                  25                  30
    aca ctc tag tgctgtttat tctcatggag gatccattca agtgtaaggt                  146
    Thr Leu
    gtctagttcc tgtactttct gcacgtgtgg catcgtgtaa aggtatatta tattatatat         206
    attttttgtt ttgaccttct tattttcagc acagtggtat gtagatatgt ctggcatatc         266
    aaaattggtc aaaacatgat ctattgtacg ttatcctctt aagtacttgt acgtttctca         326
    caggaatcga atcacaggaa aaagttagta gttctcagct ccgctccctt tgcttgggag         386
    gaggttttg atcctatgta ctacttggct ttaaaattgg tgattgtcag tgttgggttt         446
    tattctagtt ctattttgt tatttaatgt atgacaaatt ctatcttaaa caatttcgta         506
    gcttgtgagg gggtgttaaa gtcttacaag gaagaggcat tgttagttat tggtcgagtc         566
    aggaacttgt gaccaacaat tagtatcat cattattatt tataattata atcattcttt         626
    tttttttttt tttgagcaaa attata                                              652

<210> SEQ ID NO 39
<211> LENGTH: 34
<212> TYPE: PRT
<213> ORGANISM: Medicago truncatula

<400> SEQUENCE: 39

Arg Val Ile Lys Val Val Pro His Asn Arg Arg Ser Ala Thr Glu Ser
    1               5                   10                  15
    Ala Ala Arg Ile Phe Gln Ser Ile Gln Glu Glu Arg Lys Gln Tyr Asp
                20                  25                  30
    Thr Leu

<210> SEQ ID NO 40
<211> LENGTH: 368
<212> TYPE: DNA
<213> ORGANISM: Pisum sativum
<220> FEATURE:
<221> NAME/KEY: exon
<222> LOCATION: (1)..(12)
<223> OTHER INFORMATION:
<221> NAME/KEY: exon
<222> LOCATION: (93)..(368)
<223> OTHER INFORMATION:
<221> NAME/KEY: Intron
<222> LOCATION: (13)..(92)
```

-continued

```
<223> OTHER INFORMATION:

<400> SEQUENCE: 40 cag act gat aaa  ggtaaaatgg tcttactgag taattcaccc cctcaaagtt            52
       Gln Thr Asp Lys
        1
       caaacatgtt catgccaagt aattcattta atttaaacag gtt caa cat ctg att         107
                                                    Val Gln His Leu Ile
                                                              5
       gct gaa tca tca aat ctt ttg ccc gat act gct gct gtt ttg gga aaa        155
       Ala Glu Ser Ser Asn Leu Leu Pro Asp Thr Ala Ala Val Leu Gly Lys
        10                  15                  20                  25
       cct ctt ctg cag gga tct aat tct aaa agc ctt tca ttt gaa gaa gtt        203
       Pro Leu Leu Gln Gly Ser Asn Ser Lys Ser Leu Ser Phe Glu Glu Val
                           30                  35                  40
       gtt gaa cct cag gca caa aat cat aaa cag caa gac cat tct gaa aac        251
       Val Glu Pro Gln Ala Gln Asn His Lys Gln Gln Asp His Ser Glu Asn
                       45                  50                  55
       caa aac cat aaa ttg gat tat tct act gaa aat gga gtt ggg aaa aca        299
       Gln Asn His Lys Leu Asp Tyr Ser Thr Glu Asn Gly Val Gly Lys Thr
                   60                  65                  70
       tcc tta tca tcc caa aaa tca aac cag gca aat gct ggt tca cag tgt        347
       Ser Leu Ser Ser Gln Lys Ser Asn Gln Ala Asn Ala Gly Ser Gln Cys
               75                  80                  85
       ttt aat caa tca cct gga cat                                            368
       Phe Asn Gln Ser Pro Gly His
        90                  95

<210> SEQ ID NO 41
<211> LENGTH: 96
<212> TYPE: PRT
<213> ORGANISM: Pisum sativum

<400> SEQUENCE: 41

Arg Leu Ile Lys Val Gln His Leu Ile Ala Glu Ser Ser Asn Leu Leu
        1               5                   10                  15
       Pro Asp Thr Ala Ala Val Leu Gly Lys Pro Leu Leu Gln Gly Ser Asn
                       20                  25                  30
       Ser Lys Ser Leu Ser Phe Glu Glu Val Val Glu Pro Gln Ala Gln Asn
                   35                  40                  45
       His Lys Gln Gln Asp His Ser Glu Asn Gln Asn His Lys Leu Asp Tyr
               50                  55                  60
       Ser Thr Glu Asn Gly Val Gly Lys Thr Ser Leu Ser Ser Gln Lys Ser
       65                  70                  75                  80
       Asn Gln Ala Asn Ala Gly Ser Gln Cys Phe Asn Gln Ser Pro Gly His
                           85                  90                  95

<210> SEQ ID NO 42
<211> LENGTH: 523
<212> TYPE: DNA
<213> ORGANISM: Pisum sativum
<220> FEATURE:
<221> NAME/KEY: exon
<222> LOCATION: (2)..(523)
<223> OTHER INFORMATION: Partial

<400> SEQUENCE: 42 a tat ccc ggg cct gga ttt aca gga aca aat ttt gga gga tgt ggg ccc       49
         Tyr Pro Gly Pro Gly Phe Thr Gly Thr Asn Phe Gly Gly Cys Gly Pro
          1               5                   10                  15
       tac gcg gct gct cct tcg ggt ggc act ttt atg aat cct tcc tat gga         97
       Tyr Ala Ala Ala Pro Ser Gly Gly Thr Phe Met Asn Pro Ser Tyr Gly
                       20                  25                  30
       atc ccg cct cca cca gag act cct cca ggc agt caa tac ttc cct            145
       Ile Pro Pro Pro Pro Glu Thr Pro Pro Gly Ser Gln Tyr Phe Pro
                   35                  40                  45
       ccc tac ggt ggc atg cca gtt atg aaa gct gca gct tca gag tca gct        193
       Pro Tyr Gly Gly Met Pro Val Met Lys Ala Ala Ala Ser Glu Ser Ala
               50                  55                  60
       gtt gaa cat gtg aac caa ttc tcc gca cgc ggg caa agt cgt cgt tta        241
       Val Glu His Val Asn Gln Phe Ser Ala Arg Gly Gln Ser Arg Arg Leu
       65                  70                  75                  80
       tct gaa gat gaa gct gat tgt aac aaa cac aat caa agc tca tac gat        289
       Ser Glu Asp Glu Ala Asp Cys Asn Lys His Asn Gln Ser Ser Tyr Asp
```

```
              85                  90                  95
    tta cca gtt cag aga aat gga gct aca tca cat gtc atg tat cat cag      337
    Leu Pro Val Gln Arg Asn Gly Ala Thr Ser His Val Met Tyr His Gln
                    100                 105                 110
    aga tcc aag gag ttt gag gtg cag atg agt aca gca agt agt cct agc      385
    Arg Ser Lys Glu Phe Glu Val Gln Met Ser Thr Ala Ser Ser Pro Ser
                115                 120                 125
    gaa atg gca caa gaa atg agc acg gga caa gtt gcc gaa ggg aga gat      433
    Glu Met Ala Gln Glu Met Ser Thr Gly Gln Val Ala Glu Gly Arg Asp
        130                 135                 140
    gta cta cct ctt ttc cct atg gtt cca gta gaa cca gag agt gta cct      481
    Val Leu Pro Leu Phe Pro Met Val Pro Val Glu Pro Glu Ser Val Pro
    145                 150                 155                 160
    cat tct ctc gaa aca gga caa aaa act cga gtt atc aaa gtg              523
    His Ser Leu Glu Thr Gly Gln Lys Thr Arg Val Ile Lys Val
                    165                 170

<210> SEQ ID NO 43
<211> LENGTH: 174
<212> TYPE: PRT
<213> ORGANISM: Pisum sativum

<400> SEQUENCE: 43

Tyr Pro Gly Pro Gly Phe Thr Gly Thr Asn Phe Gly Gly Cys Gly Pro
    1               5                   10                  15
    Tyr Ala Ala Ala Pro Ser Gly Gly Thr Phe Met Asn Pro Ser Tyr Gly
                    20                  25                  30
    Ile Pro Pro Pro Glu Thr Pro Pro Gly Ser Gln Ala Tyr Phe Pro
                35                  40                  45
    Pro Tyr Gly Gly Met Pro Val Met Lys Ala Ala Ala Ser Glu Ser Ala
        50                  55                  60
    Val Glu His Val Asn Gln Phe Ser Ala Arg Gly Gln Ser Arg Arg Leu
    65                  70                  75                  80
    Ser Glu Asp Glu Ala Asp Cys Asn Lys His Asn Gln Ser Ser Tyr Asp
                    85                  90                  95
    Leu Pro Val Gln Arg Asn Gly Ala Thr Ser His Val Met Tyr His Gln
                    100                 105                 110
    Arg Ser Lys Glu Phe Glu Val Gln Met Ser Thr Ala Ser Ser Pro Ser
                115                 120                 125
    Glu Met Ala Gln Glu Met Ser Thr Gly Gln Val Ala Glu Gly Arg Asp
        130                 135                 140
    Val Leu Pro Leu Phe Pro Met Val Pro Val Glu Pro Glu Ser Val Pro
    145                 150                 155                 160
    His Ser Leu Glu Thr Gly Gln Lys Thr Arg Val Ile Lys Val
                    165                 170

<210> SEQ ID NO 44
<211> LENGTH: 395
<212> TYPE: DNA
<213> ORGANISM: Glycine max
<220> FEATURE:
<221> NAME/KEY: Intron
<222> LOCATION: (1)..(301)
<223> OTHER INFORMATION: partial
<221> NAME/KEY: exon
<222> LOCATION: (302)..(395)
<223> OTHER INFORMATION: partial

<400> SEQUENCE: 44
ttatgtcttg ttaatatgtc gagtcctcct gaaaaaacca tgttaagatt tgtatgatga      60
    tatgatataa attgtagaac ggaagatatt ccgcttaact gctaaccggt tttgtgatgt     120
    gatcggagcc tctgattttg gtagttagtg gtttatatat cggtgcttcc atgttccaac     180
    atgattatag atagctccaa acgcttaata tttcccttttt atttcaactg tatatttctc     240
    aagtcctaat aggacgagta ttgtgcaatt ttcttgatcc aactcctgtt cctctctaca     300
    g tca aca gag agt gtt tgc tgt cca agt gtt tga gtt gca tag act gat    349
      Ser Thr Glu Ser Val Cys Cys Pro Ser Val     Val Ala     Thr Asp
      1               5                   10
    aaa ggt cca aca gct aat tgc tgg atc acc aga tat ttt gct tga a         395
    Lys Gly Pro Thr Ala Asn Cys Trp Ile Thr Arg Tyr Phe Ala
    15                  20                  25

<210> SEQ ID NO 45
<211> LENGTH: 31
<212> TYPE: PRT
```

```
<213> ORGANISM: Glycine max

<400> SEQUENCE: 45

Gln Gln Arg Val Phe Ala Val Gln Val Phe Glu Leu His Arg Leu Ile
      1               5                   10                  15
      Lys Val Gln Gln Leu Ile Ala Gly Ser Pro Asp Ile Leu Leu Glu
                      20                  25                  30

<210> SEQ ID NO 46
<211> LENGTH: 477
<212> TYPE: DNA
<213> ORGANISM: Xanthium
<220> FEATURE:
<221> NAME/KEY: exon
<222> LOCATION: (2)..(13)
<223> OTHER INFORMATION: partial
<221> NAME/KEY: exon
<222> LOCATION: (145)..(477)
<223> OTHER INFORMATION: partial
<221> NAME/KEY: Intron
<222> LOCATION: (14)..(144)
<223> OTHER INFORMATION: partial

<400> SEQUENCE: 46 t cga cta ata rag gtaaagcaac tccaaaggct gaatctcttg tagcaatttg         53
          Arg Leu Ile Xaa
          1
      gggggagggt gtgaaataga aaatatgatc tatatactgt ttttcgattc attactacgc      113
      tgctcatgca ttttttcctgt tattttaaca g gtc cag aag ctc att gcc gag        165
                                         Val Gln Lys Leu Ile Ala Glu
                                                5                   10
      tca cca aac agt atg ctt gaa gat gct gct tat tta ggc aaa cca tta        213
      Ser Pro Asn Ser Met Leu Glu Asp Ala Ala Tyr Leu Gly Lys Pro Leu
                      15                  20                  25
      aag agt tcg tct ggt aaa aga ctg cca ttg gag tgt att att aga gaa        261
      Lys Ser Ser Ser Gly Lys Arg Leu Pro Leu Glu Cys Ile Ile Arg Glu
                  30                  35                  40
      tct caa agt gtt ccg aag cgc aag aat gat tct gag aag cct aac ttc        309
      Ser Gln Ser Val Pro Lys Arg Lys Asn Asp Ser Glu Lys Pro Asn Phe
              45                  50                  55
      agg atg gaa tgc tct gct gaa aac act gtg ggg aag gca tct ctt tct        357
      Arg Met Glu Cys Ser Ala Glu Asn Thr Val Gly Lys Ala Ser Leu Ser
      60                  65                  70                  75
      tct gtg caa aac agt agc cag ctc tct agc cac aga cca ttt tca gga        405
      Ser Val Gln Asn Ser Ser Gln Leu Ser Ser His Arg Pro Phe Ser Gly
                      80                  85                  90
      aat ccc cca cca acg cct gtg aca aac gat gct aac acg agt ccc tgg        453
      Asn Pro Pro Pro Thr Pro Val Thr Asn Asp Ala Asn Thr Ser Pro Trp
                  95                  100                 105
      tgc ttt caa caa cct ccg ggg cac                                        477
      Cys Phe Gln Gln Pro Pro Gly His
              110                 115

<210> SEQ ID NO 47
<211> LENGTH: 115
<212> TYPE: PRT
<213> ORGANISM: Xanthium
<220> FEATURE:
<221> NAME/KEY: misc_feature
<222> LOCATION: (4)..(4)
<223> OTHER INFORMATION: Xaa = uncertain amino acid residue

<400> SEQUENCE: 47

Arg Leu Ile Xaa Val Gln Lys Leu Ile Ala Glu Ser Pro Asn Ser Met
      1               5                   10                  15
      Leu Glu Asp Ala Ala Tyr Leu Gly Lys Pro Leu Lys Ser Ser Ser Gly
                      20                  25                  30
      Lys Arg Leu Pro Leu Glu Cys Ile Ile Arg Glu Ser Gln Ser Val Pro
                  35                  40                  45
      Lys Arg Lys Asn Asp Ser Glu Lys Pro Asn Phe Arg Met Glu Cys Ser
              50                  55                  60
      Ala Glu Asn Thr Val Gly Lys Ala Ser Leu Ser Ser Val Gln Asn Ser
      65                  70                  75                  80
      Ser Gln Leu Ser Ser His Arg Pro Phe Ser Gly Asn Pro Pro Pro Thr
```

```
                              85                  90                  95
            Pro Val Thr Asn Asp Ala Asn Thr Ser Pro Trp Cys Phe Gln Gln Pro
                         100                 105                 110
            Pro Gly His
                    115
```

<210> SEQ ID NO 48
<211> LENGTH: 433
<212> TYPE: DNA
<213> ORGANISM: Xanthium
<220> FEATURE:
<221> NAME/KEY: exon
<222> LOCATION: (2)..(13)
<223> OTHER INFORMATION: partial
<221> NAME/KEY: exon
<222> LOCATION: (128)..(433)
<223> OTHER INFORMATION: partial
<221> NAME/KEY: Intron
<222> LOCATION: (14)..(127)
<223> OTHER INFORMATION: partial

<400> SEQUENCE: 48

```
      t mga cta ctc rag gtaaagcaac tgtagagact gaataacttc aattatcagc        53
        Xaa Leu Leu Xaa
        1
      tttgagattt tgcattccct gtttttcctt ggacttggta ttttgctcaa attttctgt    113
      ttgttactca ttag gtc cag aaa ctg ata gct agt tcg cca aat agt ata    163
                     Val Gln Lys Leu Ile Ala Ser Ser Pro Asn Ser Ile
                       5                  10                  15
      ctc gaa gat ggt tct tct tta ggc aaa cct tta aag agg ttg tct act    211
      Leu Glu Asp Gly Ser Ser Leu Gly Lys Pro Leu Lys Arg Leu Ser Thr
                   20                  25                  30
      aaa aga ctt gca ttg gag tat aat gtc aaa gca cct gaa aat gtt tcg    259
      Lys Arg Leu Ala Leu Glu Tyr Asn Val Lys Ala Pro Glu Asn Val Ser
               35                  40                  45
      aaa cag aag aat gat tct gag aag cct aac tct agg atg gaa tcc aat    307
      Lys Gln Lys Asn Asp Ser Glu Lys Pro Asn Ser Arg Met Glu Ser Asn
       50                  55                  60
      gcc gaa aat gat gta gga gag aca tct ctt tct tgc cgc aga cca ctt    355
      Ala Glu Asn Asp Val Gly Glu Thr Ser Leu Ser Cys Arg Arg Pro Leu
      65                  70                  75                  80
      tca gaa acc ccg tca cca aca cca gta aaa cac gtt tcc cac atg ggt    403
      Ser Glu Thr Pro Ser Pro Thr Pro Val Lys His Val Ser His Met Gly
                       85                  90                  95
      ccg tgg ctc ttc aat caa cct tcg gga cac                            433
      Pro Trp Leu Phe Asn Gln Pro Ser Gly His
                      100                 105
```

<210> SEQ ID NO 49
<211> LENGTH: 106
<212> TYPE: PRT
<213> ORGANISM: Xanthium
<220> FEATURE:
<221> NAME/KEY: misc_feature
<222> LOCATION: (4)..(4)
<223> OTHER INFORMATION: Xaa = uncertain amino acid residue

<400> SEQUENCE: 49

```
      Arg Leu Leu Xaa Val Gln Lys Leu Ile Ala Ser Ser Pro Asn Ser Ile
      1               5                   10                  15
      Leu Glu Asp Gly Ser Ser Leu Gly Lys Pro Leu Lys Arg Leu Ser Thr
                   20                  25                  30
      Lys Arg Leu Ala Leu Glu Tyr Asn Val Lys Ala Pro Glu Asn Val Ser
               35                  40                  45
      Lys Gln Lys Asn Asp Ser Glu Lys Pro Asn Ser Arg Met Glu Ser Asn
       50                  55                  60
      Ala Glu Asn Asp Val Gly Glu Thr Ser Leu Ser Cys Arg Arg Pro Leu
      65                  70                  75                  80
      Ser Glu Thr Pro Ser Pro Thr Pro Val Lys His Val Ser His Met Gly
                      85                  90                  95
      Pro Trp Leu Phe Asn Gln Pro Ser Gly His
                     100                 105
```

<210> SEQ ID NO 50

```
<211> LENGTH: 526
<212> TYPE: DNA
<213> ORGANISM: Xanthium
<220> FEATURE:
<221> NAME/KEY: exon
<222> LOCATION: (2)..(526)
<223> OTHER INFORMATION: partial

<400> SEQUENCE: 50 a cat cct gga cct gca ttc atg agt cca gta tat ggc ggt tgt gga ccc      49
      His Pro Gly Pro Ala Phe Met Ser Pro Val Tyr Gly Gly Cys Gly Pro
      1               5                  10                  15
    ccg att cca atg acg gga aac ttt tta gct ccg gca tac tat caa gga         97
    Pro Ile Pro Met Thr Gly Asn Phe Leu Ala Pro Ala Tyr Tyr Gln Gly
                    20                  25                  30
    acg gga gct cct ttc gca cct caa cct agt cat ggc tac ttt cct ccg        145
    Thr Gly Ala Pro Phe Ala Pro Gln Pro Ser His Gly Tyr Phe Pro Pro
                35                  40                  45
    ttt gac atg cca gtt atg aat cca gta atc cca tct cca gct att gat        193
    Phe Asp Met Pro Val Met Asn Pro Val Ile Pro Ser Pro Ala Ile Asp
    50                  55                  60
    caa ccg gac cag gtt gct gca acg ggt ttt caa ggt ctg tta tcg aga        241
    Gln Pro Asp Gln Val Ala Ala Thr Gly Phe Gln Gly Leu Leu Ser Arg
    65                  70                  75                  80
    gat cag gaa gtt aat ttt cac att caa caa cag aac tca agt aat gtt        289
    Asp Gln Glu Val Asn Phe His Ile Gln Gln Gln Asn Ser Ser Asn Val
                    85                  90                  95
    gcg aga gag aat aat gta gcc gcg cca aag gtt gtg aga ttg tat ccc        337
    Ala Arg Glu Asn Asn Val Ala Ala Pro Lys Val Val Arg Leu Tyr Pro
                100                 105                 110
    tct aga gat tct gag ttg caa gcc agc act gca agt agt cca agg gaa        385
    Ser Arg Asp Ser Glu Leu Gln Ala Ser Thr Ala Ser Ser Pro Arg Glu
                115                 120                 125
    aga ggt cat gga tta gac gtg ggc aac tcc acc gga gga aga agc gtg        433
    Arg Gly His Gly Leu Asp Val Gly Asn Ser Thr Gly Gly Arg Ser Val
    130                 135                 140
    ttt cct ctg ttc cca act ttt cct gct att agc aac ccc gct agt agc        481
    Phe Pro Leu Phe Pro Thr Phe Pro Ala Ile Ser Asn Pro Ala Ser Ser
    145                 150                 155                 160
    tcc cag cct cat ttt cct agt cat acg gct aga gtt atc aaa gtt            526
    Ser Gln Pro His Phe Pro Ser His Thr Ala Arg Val Ile Lys Val
                    165                 170                 175

<210> SEQ ID NO 51
<211> LENGTH: 175
<212> TYPE: PRT
<213> ORGANISM: Xanthium

<400> SEQUENCE: 51

His Pro Gly Pro Ala Phe Met Ser Pro Val Tyr Gly Gly Cys Gly Pro
    1               5                  10                  15
    Pro Ile Pro Met Thr Gly Asn Phe Leu Ala Pro Ala Tyr Tyr Gln Gly
                    20                  25                  30
    Thr Gly Ala Pro Phe Ala Pro Gln Pro Ser His Gly Tyr Phe Pro Pro
                35                  40                  45
    Phe Asp Met Pro Val Met Asn Pro Val Ile Pro Ser Pro Ala Ile Asp
    50                  55                  60
    Gln Pro Asp Gln Val Ala Ala Thr Gly Phe Gln Gly Leu Leu Ser Arg
    65                  70                  75                  80
    Asp Gln Glu Val Asn Phe His Ile Gln Gln Gln Asn Ser Ser Asn Val
                    85                  90                  95
    Ala Arg Glu Asn Asn Val Ala Ala Pro Lys Val Val Arg Leu Tyr Pro
                100                 105                 110
    Ser Arg Asp Ser Glu Leu Gln Ala Ser Thr Ala Ser Ser Pro Arg Glu
                115                 120                 125
    Arg Gly His Gly Leu Asp Val Gly Asn Ser Thr Gly Gly Arg Ser Val
    130                 135                 140
    Phe Pro Leu Phe Pro Thr Phe Pro Ala Ile Ser Asn Pro Ala Ser Ser
    145                 150                 155                 160
    Ser Gln Pro His Phe Pro Ser His Thr Ala Arg Val Ile Lys Val
                    165                 170                 175

<210> SEQ ID NO 52
<211> LENGTH: 532
<212> TYPE: DNA
```

```
<213> ORGANISM: poplar trees
<220> FEATURE:
<221> NAME/KEY: exon
<222> LOCATION: (2)..(532)
<223> OTHER INFORMATION: partial

<400> SEQUENCE: 52 t tac act gcc cck gga ttc atg gga tcg ggt tgt gga gga tgt gga cct      49
      Tyr Thr Ala Xaa Gly Phe Met Gly Ser Gly Cys Gly Gly Cys Gly Pro
      1               5                  10                  15
    ttt ggg cca att ccc ttg aca gac aac ttt atg act tca gct tat gcg        97
    Phe Gly Pro Ile Pro Leu Thr Asp Asn Phe Met Thr Ser Ala Tyr Ala
                     20                  25                  30
    att cca aca tct cat tat cat caa ggt att ggg gtc tca cca ggt gct       145
    Ile Pro Thr Ser His Tyr His Gln Gly Ile Gly Val Ser Pro Gly Ala
                 35                  40                  45
    cct cca gtt ggt aat gct tgc ttc gcc cca tat ggc atg cca gga atg       193
    Pro Pro Val Gly Asn Ala Cys Phe Ala Pro Tyr Gly Met Pro Gly Met
             50                  55                  60
    aac cca gcc atc tca ggt tct gca ggg tct ggt tcc tgt ggt caa act       241
    Asn Pro Ala Ile Ser Gly Ser Ala Gly Ser Gly Ser Cys Gly Gln Thr
    65                  70                  75                  80
    gct cag ttt cca gga ggc att ttg agc tcg aac atg cca cat caa agc       289
    Ala Gln Phe Pro Gly Gly Ile Leu Ser Ser Asn Met Pro His Gln Ser
                     85                  90                  95
    tca tgt aat gaa cgg act caa aag agt gaa gct gtt tta gaa ggt atg       337
    Ser Cys Asn Glu Arg Thr Gln Lys Ser Glu Ala Val Leu Glu Gly Met
                100                 105                 110
    aag ctt cgg gca tct aaa aac act tcg gta caa gga agt aca ggt agt       385
    Lys Leu Arg Ala Ser Lys Asn Thr Ser Val Gln Gly Ser Thr Gly Ser
                115                 120                 125
    agt ccc agt ggc aga gtg caa ggg gtt ggg act gtt caa gcc gct gat       433
    Ser Pro Ser Gly Arg Val Gln Gly Val Gly Thr Val Gln Ala Ala Asp
            130                 135                 140
    gga aga gct gcg ttc cca cct ttc cca gtg act cct cct tgc cct gag       481
    Gly Arg Ala Ala Phe Pro Pro Phe Pro Val Thr Pro Pro Cys Pro Glu
    145                 150                 155                 160
    gga gcc cct cag cat caa gag aca gac cag ctg tcg aaa gtg atc aag       529
    Gly Ala Pro Gln His Gln Glu Thr Asp Gln Leu Ser Lys Val Ile Lys
                    165                 170                 175
    gtt                                                                   532
    Val <210> SEQ ID NO 53
<211> LENGTH: 177
<212> TYPE: PRT
<213> ORGANISM: Poplar trees
<220> FEATURE:
<221> NAME/KEY: misc_feature
<222> LOCATION: (4)..(4)
<223> OTHER INFORMATION: Xaa = uncertain amino acid residue

<400> SEQUENCE: 53

Tyr Thr Ala Xaa Gly Phe Met Gly Ser Gly Cys Gly Gly Cys Gly Pro
        1               5                  10                  15
        Phe Gly Pro Ile Pro Leu Thr Asp Asn Phe Met Thr Ser Ala Tyr Ala
                         20                  25                  30
        Ile Pro Thr Ser His Tyr His Gln Gly Ile Gly Val Ser Pro Gly Ala
                     35                  40                  45
        Pro Pro Val Gly Asn Ala Cys Phe Ala Pro Tyr Gly Met Pro Gly Met
                 50                  55                  60
        Asn Pro Ala Ile Ser Gly Ser Ala Gly Ser Gly Ser Cys Gly Gln Thr
        65                  70                  75                  80
        Ala Gln Phe Pro Gly Gly Ile Leu Ser Ser Asn Met Pro His Gln Ser
                         85                  90                  95
        Ser Cys Asn Glu Arg Thr Gln Lys Ser Glu Ala Val Leu Glu Gly Met
                    100                 105                 110
        Lys Leu Arg Ala Ser Lys Asn Thr Ser Val Gln Gly Ser Thr Gly Ser
                    115                 120                 125
        Ser Pro Ser Gly Arg Val Gln Gly Val Gly Thr Val Gln Ala Ala Asp
                130                 135                 140
        Gly Arg Ala Ala Phe Pro Pro Phe Pro Val Thr Pro Pro Cys Pro Glu
        145                 150                 155                 160
        Gly Ala Pro Gln His Gln Glu Thr Asp Gln Leu Ser Lys Val Ile Lys
                        165                 170                 175
        Val
```

<210> SEQ ID NO 54
<211> LENGTH: 418
<212> TYPE: DNA
<213> ORGANISM: Mimulus sp.
<220> FEATURE:
<221> NAME/KEY: exon
<222> LOCATION: (2)..(418)
<223> OTHER INFORMATION:

<400> SEQUENCE: 54

```
     g tac ccg ttc gtc agc caa ccc tgt gga ggg ggc tgc ggc ccc cct gga     49
       Tyr Pro Phe Val Ser Gln Pro Cys Gly Gly Gly Cys Gly Pro Pro Gly
         1               5                  10                  15
     tcg aat cca acg gtg gga aat ttc tca act cca cca ccg cca caa tat        97
     Ser Asn Pro Thr Val Gly Asn Phe Ser Thr Pro Pro Pro Pro Gln Tyr
                      20                  25                  30
     cat cat tta cct tct ttc cct cag ttc ccc ccc cac ggc tac ttc cct       145
     His His Leu Pro Ser Phe Pro Gln Phe Pro Pro His Gly Tyr Phe Pro
                  35                  40                  45
     cct tac tgt gtc ccg att atg gac acg tca gca ttc tcg ggc ccg ccc       193
     Pro Tyr Cys Val Pro Ile Met Asp Thr Ser Ala Phe Ser Gly Pro Pro
              50                  55                  60
     ccc gaa cag acc ata cga gcc cca gct gct gca ggc cca gct gta caa       241
     Pro Glu Gln Thr Ile Arg Ala Pro Ala Ala Ala Gly Pro Ala Val Gln
     65                  70                  75                  80
     aaa agc ggg ccc gct tta tgg gat gtc gaa atg caa ggg agc aca gct       289
     Lys Ser Gly Pro Ala Leu Trp Asp Val Glu Met Gln Gly Ser Thr Ala
                      85                  90                  95
     agt agc ccg agt ggg agg cgt aaa aga gga agc aac ggt gtt gaa ttt       337
     Ser Ser Pro Ser Gly Arg Arg Lys Arg Gly Ser Asn Gly Val Glu Phe
                 100                 105                 110
     gaa aga agg aat atg ctt ccg ctt ttc ccc act acc cca gct gct gtg       385
     Glu Arg Arg Asn Met Leu Pro Leu Phe Pro Thr Thr Pro Ala Ala Val
                 115                 120                 125
     gat gcc ttg aaa cca acg cgg gtg att aag gtt                           418
     Asp Ala Leu Lys Pro Thr Arg Val Ile Lys Val
             130                 135
```

<210> SEQ ID NO 55
<211> LENGTH: 139
<212> TYPE: PRT
<213> ORGANISM: Mimulus sp.

<400> SEQUENCE: 55

```
     Tyr Pro Phe Val Ser Gln Pro Cys Gly Gly Gly Cys Gly Pro Pro Gly
     1               5                  10                  15
     Ser Asn Pro Thr Val Gly Asn Phe Ser Thr Pro Pro Pro Pro Gln Tyr
                     20                  25                  30
     His His Leu Pro Ser Phe Pro Gln Phe Pro Pro His Gly Tyr Phe Pro
                 35                  40                  45
     Pro Tyr Cys Val Pro Ile Met Asp Thr Ser Ala Phe Ser Gly Pro Pro
             50                  55                  60
     Pro Glu Gln Thr Ile Arg Ala Pro Ala Ala Ala Gly Pro Ala Val Gln
     65                  70                  75                  80
     Lys Ser Gly Pro Ala Leu Trp Asp Val Glu Met Gln Gly Ser Thr Ala
                     85                  90                  95
     Ser Ser Pro Ser Gly Arg Arg Lys Arg Gly Ser Asn Gly Val Glu Phe
                 100                 105                 110
     Glu Arg Arg Asn Met Leu Pro Leu Phe Pro Thr Thr Pro Ala Ala Val
                 115                 120                 125
     Asp Ala Leu Lys Pro Thr Arg Val Ile Lys Val
             130                 135
```

<210> SEQ ID NO 56
<211> LENGTH: 1272
<212> TYPE: DNA
<213> ORGANISM: Zea mays
<220> FEATURE:
<221> NAME/KEY: exon
<222> LOCATION: (3)..(185)
<223> OTHER INFORMATION: partial
<221> NAME/KEY: Intron
<222> LOCATION: (186)..(295)

<223> OTHER INFORMATION:
<221> NAME/KEY: exon
<222> LOCATION: (296)..(1066)
<223> OTHER INFORMATION:
<221> NAME/KEY: 3'UTR
<222> LOCATION: (1067)..(1272)
<223> OTHER INFORMATION:

<400> SEQUENCE: 56

```
    at gac gtg gag caa aac gat gat ctg tct gat tcc tct gtt gaa tct           47
       Asp Val Glu Gln Asn Asp Asp Leu Ser Asp Ser Ser Val Glu Ser
        1               5                  10                  15
    ttg cct gga atg gag att tct cca gat gat gtt gtc agt gct att ggt          95
    Leu Pro Gly Met Glu Ile Ser Pro Asp Asp Val Val Ser Ala Ile Gly
                     20                  25                  30
    ccc aag cat ttt tgg aaa gcg aga aga gct att gtc aat cag cag agg         143
    Pro Lys His Phe Trp Lys Ala Arg Arg Ala Ile Val Asn Gln Gln Arg
                 35                  40                  45
    gta ttt gct gtt caa gta ttc gag ctg cat agg ttg atc aaa                 185
    Val Phe Ala Val Gln Val Phe Glu Leu His Arg Leu Ile Lys
             50                  55                  60
    gtgagtctgc ggcaaataaa tataacttct ttgggcccat gcttatgggc aggttaatttt      245
    aaatttgaaa awttggttta acsgttgttt atgttgactt ttgcaatcag gtg cag          301
                                                              Val Gln
    aag ttg atc gct gca tct cca cat gta ctt att gag ggg gat cct tgc         349
    Lys Leu Ile Ala Ala Ser Pro His Val Leu Ile Glu Gly Asp Pro Cys
         65                  70                  75
    ctt ggc aaa tcc ttg gcg gtg agc aag aaa agg ctg gct gga gat gtg         397
    Leu Gly Lys Ser Leu Ala Val Ser Lys Lys Arg Leu Ala Gly Asp Val
    80                  85                  90                  95
    gaa aca cag ctt gaa tca gct aaa aac gat gat ggc gtg cga cca acg         445
    Glu Thr Gln Leu Glu Ser Ala Lys Asn Asp Asp Gly Val Arg Pro Thr
                    100                 105                 110
    cag cta gag cac tcg aaa gag aag act gaa gcg aac caa cct tca cca         493
    Gln Leu Glu His Ser Lys Glu Lys Thr Glu Ala Asn Gln Pro Ser Pro
                115                 120                 125
    tct caa gac gaa cag gcc gca act aat ggt gac gtt gct gcc ttg atg         541
    Ser Gln Asp Glu Gln Ala Ala Thr Asn Gly Asp Val Ala Ala Leu Met
            130                 135                 140
    cat acc cct tcc gac aac aaa cag aag agc tgg tgc att cct gca cct         589
    His Thr Pro Ser Asp Asn Lys Gln Lys Ser Trp Cys Ile Pro Ala Pro
        145                 150                 155
    cca agt cag tgg ctg att cct gtw atg tcc ccg tct gaa gga ctt gtc         637
    Pro Ser Gln Trp Leu Ile Pro Xaa Met Ser Pro Ser Glu Gly Leu Val
    160                 165                 170                 175
    tac aag cct tat acc ggg cac tgc cct ccg gtg gga agt ctt ttg gcg         685
    Tyr Lys Pro Tyr Thr Gly His Cys Pro Pro Val Gly Ser Leu Leu Ala
                    180                 185                 190
    ccc cca ttt ttt gcc agc tac ccc acc tcc tcc tcc aca gct ggg             733
    Pro Pro Phe Phe Ala Ser Tyr Pro Thr Ser Ser Ser Ser Thr Ala Gly
                195                 200                 205
    ggg gat ttc atg agt tcg gca tgt gga gcc agg ctg atg agt gcc cct         781
    Gly Asp Phe Met Ser Ser Ala Cys Gly Ala Arg Leu Met Ser Ala Pro
            210                 215                 220
    gtg tac ttc ccg tct ttc agc atg cct gca gtg tca ggg tct gca gtt         829
    Val Tyr Phe Pro Ser Phe Ser Met Pro Ala Val Ser Gly Ser Ala Val
        225                 230                 235
    gag caa gtg agc cat gtt gca gcg tcg cag cat aaa cgg aac tcg tgt         877
    Glu Gln Val Ser His Val Ala Ala Ser Gln His Lys Arg Asn Ser Cys
    240                 245                 250                 255
    agt gaa gcg gtg ttg gca tca agg gac agc gag gtg caa ggc agt agt         925
    Ser Glu Ala Val Leu Ala Ser Arg Asp Ser Glu Val Gln Gly Ser Ser
                    260                 265                 270
    gct agc agt ccg gca tct tct gaa aca gca gct caa ccc agg gtc att         973
    Ala Ser Ser Pro Ala Ser Ser Glu Thr Ala Ala Gln Pro Arg Val Ile
                275                 280                 285
    agg gtt gtt ccc cac acg gca cgc acg gct tca gag tcg gca gca agg        1021
    Arg Val Val Pro His Thr Ala Arg Thr Ala Ser Glu Ser Ala Ala Arg
            290                 295                 300
    att ttc cgc tca ata cag atg gag agg aaa caa aac gac ccg tga           1066
    Ile Phe Arg Ser Ile Gln Met Glu Arg Lys Gln Asn Asp Pro
        305                 310                 315
    ctggcagata aaaatgaaag aacggaggga gtagactaat tttttgaccg ataattataa     1126
    tgatcgccgt aaattggctg gcccgcccgc cttatgtttt ttgttcagtg taaatatgct     1186
    gtgtctgtca gaatgatatg gcatctgtag ctattttggt tctgtcagaa tcatgttgat     1246
    tggaattaaa aaaaaaaaaa aaaaaa                                         1272
```

```
<210> SEQ ID NO 57
<211> LENGTH: 317
<212> TYPE: PRT
<213> ORGANISM: Zea mays

<400> SEQUENCE: 57
```

```
     Asp Val Glu Gln Asn Asp Asp Leu Ser Asp Ser Val Glu Ser Leu
     1               5                   10                  15
     Pro Gly Met Glu Ile Ser Pro Asp Asp Val Val Ser Ala Ile Gly Pro
                 20                  25                  30
     Lys His Phe Trp Lys Ala Arg Arg Ala Ile Val Asn Gln Gln Arg Val
                     35                  40                  45
     Phe Ala Val Gln Val Phe Glu Leu His Arg Leu Ile Lys Val Gln Lys
                 50                  55                  60
     Leu Ile Ala Ala Ser Pro His Val Leu Ile Glu Gly Asp Pro Cys Leu
     65                  70                  75                  80
     Gly Lys Ser Leu Ala Val Ser Lys Lys Arg Leu Ala Gly Asp Val Glu
                     85                  90                  95
     Thr Gln Leu Glu Ser Ala Lys Asn Asp Asp Gly Val Arg Pro Thr Gln
                 100                 105                 110
     Leu Glu His Ser Lys Glu Lys Thr Glu Ala Asn Gln Pro Ser Pro Ser
                 115                 120                 125
     Gln Asp Glu Gln Ala Ala Thr Asn Gly Asp Val Ala Ala Leu Met His
                 130                 135                 140
     Thr Pro Ser Asp Asn Lys Gln Lys Ser Trp Cys Ile Pro Ala Pro Pro
     145                 150                 155                 160
     Ser Gln Trp Leu Ile Pro Val Met Ser Pro Ser Glu Gly Leu Val Tyr
                     165                 170                 175
     Lys Pro Tyr Thr Gly His Cys Pro Pro Val Gly Ser Leu Leu Ala Pro
                 180                 185                 190
     Pro Phe Phe Ala Ser Tyr Pro Thr Ser Ser Ser Thr Ala Gly Gly
                 195                 200                 205
     Asp Phe Met Ser Ser Ala Cys Gly Ala Arg Leu Met Ser Ala Pro Val
                 210                 215                 220
     Tyr Phe Pro Ser Phe Met Pro Ala Val Ser Gly Ser Ala Val Glu
     225                 230                 235                 240
     Gln Val Ser His Val Ala Ala Ser Gln His Lys Arg Asn Ser Cys Ser
                     245                 250                 255
     Glu Ala Val Leu Ala Ser Arg Asp Ser Glu Val Gln Gly Ser Ser Ala
                 260                 265                 270
     Ser Ser Pro Ala Ser Ser Glu Thr Ala Ala Gln Pro Arg Val Ile Arg
                 275                 280                 285
     Val Val Pro His Thr Ala Arg Thr Ala Ser Glu Ser Ala Ala Arg Ile
                 290                 295                 300
     Phe Arg Ser Ile Gln Met Glu Arg Lys Gln Asn Asp Pro
     305                 310                 315
```

```
<210> SEQ ID NO 58
<211> LENGTH: 1980
<212> TYPE: DNA
<213> ORGANISM: Lycopersicon esculentum
<220> FEATURE:
<221> NAME/KEY: exon
<222> LOCATION: (2)..(1804)
<223> OTHER INFORMATION: portion of exon 1, exon 2, exon 3, and exon 4, including stop cod
      on
<221> NAME/KEY: 3'UTR
<222> LOCATION: (1085)..(1980)
<223> OTHER INFORMATION: partial

<400> SEQUENCE: 58
```

```
     g cct tct cag aga ttc aac tct ggg gtt ttg cct ctt gat cct aac aat    49
       Pro Ser Gln Arg Phe Asn Ser Gly Val Leu Pro Leu Asp Pro Asn Asn
       1               5                   10                  15
     act tca aag atg gcc cct cca tcc tca agc cag ggg agt ggg cat gac      97
     Thr Ser Lys Met Ala Pro Pro Ser Ser Ser Gln Gly Ser Gly His Asp
                     20                  25                  30
     aga agt gga tat ctc cct ata caa cac cct cca tct aga cgt cta gct      145
     Arg Ser Gly Tyr Leu Pro Ile Gln His Pro Pro Ser Arg Arg Leu Ala
                 35                  40                  45
     gat aaa cca cct ggc cac agt tcc gat ccc agt act ctc ttg caa caa      193
     Asp Lys Pro Pro Gly His Ser Ser Asp Pro Ser Thr Leu Leu Gln Gln
                 50                  55                  60
     tat gaa ttg aaa aag aga aca gaa gag gat gac ttt acg gtc ccc atc      241
     Tyr Glu Leu Lys Lys Arg Thr Glu Glu Asp Asp Phe Thr Val Pro Ile
     65                  70                  75                  80
```

| | | |
|---|---|---|
| ttt gtt aat tcc aag ctc ggt cag gcc cat ggg agt cat aat gtg aat<br>Phe Val Asn Ser Lys Leu Gly Gln Ala His Gly Ser His Asn Val Asn<br>85 90 95 | | 289 |
| atg gaa aag ctc tca ccc tct ggt caa ctg ttt tgt cct aat aaa gag<br>Met Glu Lys Leu Ser Pro Ser Gly Gln Leu Phe Cys Pro Asn Lys Glu<br>100 105 110 | | 337 |
| ttg gaa gga gtt aca cat cta aca ttg aga caa cag cgc aat agc caa<br>Leu Glu Gly Val Thr His Leu Thr Leu Arg Gln Gln Arg Asn Ser Gln<br>115 120 125 | | 385 |
| aac aag gag aat ctc aaa tgt act ctt gct cgt aga gag aaa aca acc<br>Asn Lys Glu Asn Leu Lys Cys Thr Leu Ala Arg Arg Glu Lys Thr Thr<br>130 135 140 | | 433 |
| tca aac tct gca tcc aag gaa tgc aga ttg gat cct cag gtt ggt tgt<br>Ser Asn Ser Ala Ser Lys Glu Cys Arg Leu Asp Pro Gln Val Gly Cys<br>145 150 155 160 | | 481 |
| agt agc ata cct gaa cct gtt aag gga aca tat gat ggc agt tcg tat<br>Ser Ser Ile Pro Glu Pro Val Lys Gly Thr Tyr Asp Gly Ser Ser Tyr<br>165 170 175 | | 529 |
| cct agg aaa gaa ttt gta tca taa gag cag tta act gct aat gat ctt<br>Pro Arg Lys Glu Phe Val Ser     Glu Gln Leu Thr Ala Asn Asp Leu<br>180                    185                190 | | 577 |
| gtt aat gat acg gaa tcc cag gaa gac agg gca cac aaa tca tta caa<br>Val Asn Asp Thr Glu Ser Gln Glu Asp Arg Ala His Lys Ser Leu Gln<br>195 200 205 | | 625 |
| aca gga aat ttg gac cga ggt gac gac tta tct gag act tcc aga gtg<br>Thr Gly Asn Leu Asp Arg Gly Asp Asp Leu Ser Glu Thr Ser Arg Val<br>210 215 220 | | 673 |
| gaa tct att tct gga aca gac atc tct cct gat gac gta gga ata<br>Glu Ser Ile Ser Gly Thr Asp Ile Ser Pro Asp Asp Ile Val Gly Ile<br>225 230 235 | | 721 |
| att ggc tta aag cgt ttc tgg aaa gcc aga aga gca att gtc aac cag<br>Ile Gly Leu Lys Arg Phe Trp Lys Ala Arg Arg Ala Ile Val Asn Gln<br>240 245 250 255 | | 769 |
| caa aga gtg ttt gca atc caa gtg ttc gag ttg cat cga cta ata aag<br>Gln Arg Val Phe Ala Ile Gln Val Phe Glu Leu His Arg Leu Ile Lys<br>260 265 270 | | 817 |
| gta caa agg ctc att gcc ggg tca cca aat agt tcg ctc gaa gat cct<br>Val Gln Arg Leu Ile Ala Gly Ser Pro Asn Ser Ser Leu Glu Asp Pro<br>275 280 285 | | 865 |
| gct tat tta ggc aaa cct tta aag tca tcg atc aaa aga ctt cca<br>Ala Tyr Leu Gly Lys Pro Leu Lys Ser Ser Ile Lys Arg Leu Pro<br>290 295 300 | | 913 |
| ttg gac tgt att gtt aga gaa tct caa agt gtt ctg aag cgc aag cat<br>Leu Asp Cys Ile Val Arg Glu Ser Gln Ser Val Leu Lys Arg Lys His<br>305 310 315 | | 961 |
| gat tct gag aag cct cac ttc agg atg gaa cac act gcc gaa agc aat<br>Asp Ser Glu Lys Pro His Phe Arg Met Glu His Thr Ala Glu Ser Asn<br>320 325 330 335 | | 1009 |
| gtg gga aag gca tct ctc tct act gtg caa aat ggt agt caa ctc tct<br>Val Gly Lys Ala Ser Leu Ser Thr Val Gln Asn Gly Ser Gln Leu Ser<br>340 345 350 | | 1057 |
| agc cac aaa cca ttt tca gga act cca ctg cct aca cct gta aca aat<br>Ser His Lys Pro Phe Ser Gly Thr Pro Leu Pro Thr Pro Val Thr Asn<br>355 360 365 | | 1105 |
| gat tct aat gcg ggt cct tgg tgc ttc caa caa cct ccc ggg cac caa<br>Asp Ser Asn Ala Gly Pro Trp Cys Phe Gln Gln Pro Pro Gly His Gln<br>370 375 380 | | 1153 |
| tgg ttg atc cca gtg atg tct cct tct gag gga ctt gta tac aag cca<br>Trp Leu Ile Pro Val Met Ser Pro Ser Glu Gly Leu Val Tyr Lys Pro<br>385 390 395 | | 1201 |
| ttt cct gga cct gga ttc acg agt cct att tgt gga agt ggg cct cca<br>Phe Pro Gly Pro Gly Phe Thr Ser Pro Ile Cys Gly Ser Gly Pro Pro<br>400 405 410 415 | | 1249 |
| gga tcg agt cca aca atg ggg aac ttt ttt gct cca aca tat gga gtt<br>Gly Ser Ser Pro Thr Met Gly Asn Phe Phe Ala Pro Thr Tyr Gly Val<br>420 425 430 | | 1297 |
| cct gct cct aat cct cac tat caa ggt atg gga gtt cct ttt gca cct<br>Pro Ala Pro Asn Pro His Tyr Gln Gly Met Gly Val Pro Phe Ala Pro<br>435 440 445 | | 1345 |
| ccg act ggt cat ggt tac ttt cgg caa tat ggc atg cca gct atg aat<br>Pro Thr Gly His Gly Tyr Phe Arg Gln Tyr Gly Met Pro Ala Met Asn<br>450 455 460 | | 1393 |
| cca cca att tca tca act gct agt gaa gaa tcg aac cag tat acc atg<br>Pro Pro Ile Ser Ser Thr Ala Ser Glu Glu Ser Asn Gln Tyr Thr Met<br>465 470 475 | | 1441 |
| cct ggt tta caa cac cag ttt tct gga gta gtt gat gac gtc aac att<br>Pro Gly Leu Gln His Gln Phe Ser Gly Val Val Asp Asp Val Asn Ile<br>480 485 490 495 | | 1489 |
| caa cat cag gac tca agt aat gtt cta aat cag aag aaa gaa aat gtc | | 1537 |

```
        Gln His Gln Asp Ser Ser Asn Val Leu Asn Gln Lys Lys Glu Asn Val
                        500                 505                 510
        ccg gat gtt gta agg tat caa tcc aca aaa gat aat gag gta caa gcc      1585
        Pro Asp Val Val Arg Tyr Gln Ser Thr Lys Asp Asn Glu Val Gln Ala
                        515                 520                 525
        agc agt gca agt agt cct att gag aca gca gga aga aac atg ctc tct      1633
        Ser Ser Ala Ser Ser Pro Ile Glu Thr Ala Gly Arg Asn Met Leu Ser
                        530                 535                 540
        ctt ttt ccc acg tct cca gtt act gac aac cgt gat ggt agc cct cag      1681
        Leu Phe Pro Thr Ser Pro Val Thr Asp Asn Arg Asp Gly Ser Pro Gln
                    545                 550                 555
        gct tgt gtg cct gat aat cca gcc aga gtt atc aag gtt gta cct cac      1729
        Ala Cys Val Pro Asp Asn Pro Ala Arg Val Ile Lys Val Val Pro His
        560                 565                 570                 575
        aat gca agg tct gct aca gaa tcc gta gct cgg ata ttt cag tct ata      1777
        Asn Ala Arg Ser Ala Thr Glu Ser Val Ala Arg Ile Phe Gln Ser Ile
                        580                 585                 590
        caa caa gag aga aat aat atg act tag gtttaacaca tctataagta            1824
        Gln Gln Glu Arg Asn Asn Met Thr
                        595
        gcttaccttg tgaatatgac catttgctca tcctggcaaa atgtagtagt ttcagtcaat    1884
        ttgttgtatc tttcttttct acagaaagta tgtaatagct gtattttaat ttggttgctg    1944
        tagataagca tacctgcaaa aaaaaaaaaa aaaac                               1980

<210> SEQ ID NO 59
<211> LENGTH: 599
<212> TYPE: PRT
<213> ORGANISM: Lycopersicum esculentum

<400> SEQUENCE: 59

Pro Ser Gln Arg Phe Asn Ser Gly Val Leu Pro Leu Asp Pro Asn Asn
        1               5                   10                  15
        Thr Ser Lys Met Ala Pro Pro Ser Ser Gln Gly Ser Gly His Asp
                    20                  25                  30
        Arg Ser Gly Tyr Leu Pro Ile Gln His Pro Pro Ser Arg Arg Leu Ala
                    35                  40                  45
        Asp Lys Pro Pro Gly His Ser Ser Asp Pro Ser Thr Leu Leu Gln Gln
        50                  55                  60
        Tyr Glu Leu Lys Lys Arg Thr Glu Asp Asp Phe Thr Val Pro Ile
        65                  70                  75                  80
        Phe Val Asn Ser Lys Leu Gly Gln Ala His Gly Ser His Asn Val Asn
                        85                  90                  95
        Met Glu Lys Leu Ser Pro Ser Gly Gln Leu Phe Cys Pro Asn Lys Glu
                    100                 105                 110
        Leu Glu Gly Val Thr His Leu Thr Leu Arg Gln Gln Arg Asn Ser Gln
                    115                 120                 125
        Asn Lys Glu Asn Leu Lys Cys Thr Leu Ala Arg Arg Glu Lys Thr Thr
            130                 135                 140
        Ser Asn Ser Ala Ser Lys Glu Cys Arg Leu Asp Pro Gln Val Gly Cys
        145                 150                 155                 160
        Ser Ser Ile Pro Glu Pro Val Lys Gly Thr Tyr Asp Gly Ser Ser Tyr
                        165                 170                 175
        Pro Arg Lys Glu Phe Val Ser Glu Gln Leu Thr Ala Asn Asp Leu Val
                    180                 185                 190
        Asn Asp Thr Glu Ser Gln Glu Asp Arg Ala His Lys Ser Leu Gln Thr
                    195                 200                 205
        Gly Asn Leu Asp Arg Gly Asp Asp Leu Ser Glu Thr Ser Arg Val Glu
            210                 215                 220
        Ser Ile Ser Gly Thr Asp Ile Ser Pro Asp Asp Ile Val Gly Ile Ile
        225                 230                 235                 240
        Gly Leu Lys Arg Phe Trp Lys Ala Arg Arg Ala Ile Val Asn Gln Gln
                        245                 250                 255
        Arg Val Phe Ala Ile Gln Val Phe Glu Leu His Arg Leu Ile Lys Val
                    260                 265                 270
        Gln Arg Leu Ile Ala Gly Ser Pro Asn Ser Ser Leu Glu Asp Pro Ala
                    275                 280                 285
        Tyr Leu Gly Lys Pro Leu Lys Ser Ser Ser Ile Lys Arg Leu Pro Leu
            290                 295                 300
        Asp Cys Ile Val Arg Glu Ser Gln Ser Val Leu Lys Arg Lys His Asp
        305                 310                 315                 320
        Ser Glu Lys Pro His Phe Arg Met Glu His Thr Ala Glu Ser Asn Val
                        325                 330                 335
        Gly Lys Ala Ser Leu Ser Thr Val Gln Asn Gly Ser Gln Leu Ser Ser
                    340                 345                 350
        His Lys Pro Phe Ser Gly Thr Pro Leu Pro Thr Pro Val Thr Asn Asp
                    355                 360                 365
        Ser Asn Ala Gly Pro Trp Cys Phe Gln Gln Pro Pro Gly His Gln Trp
```

```
            370                 375                  380
Leu Ile Pro Val Met Ser Pro Ser Glu Gly Leu Val Tyr Lys Pro Phe
385                 390                  395                 400
Pro Gly Pro Gly Phe Thr Ser Pro Ile Cys Gly Ser Gly Pro Pro Gly
                405                 410                 415
Ser Ser Pro Thr Met Gly Asn Phe Ala Pro Thr Tyr Gly Val Pro
            420                 425                 430
Ala Pro Asn Pro His Tyr Gln Gly Met Gly Val Pro Phe Ala Pro Pro
            435                 440                 445
Thr Gly His Gly Tyr Phe Arg Gln Tyr Gly Met Pro Ala Met Asn Pro
            450                 455                 460
Pro Ile Ser Ser Thr Ala Ser Glu Glu Ser Asn Gln Tyr Thr Met Pro
465                 470                 475                 480
Gly Leu Gln His Gln Phe Ser Gly Val Val Asp Asp Val Asn Ile Gln
                485                 490                 495
His Gln Asp Ser Ser Asn Val Leu Asn Gln Lys Lys Glu Asn Val Pro
                500                 505                 510
Asp Val Val Arg Tyr Gln Ser Thr Lys Asp Asn Glu Val Gln Ala Ser
            515                 520                 525
Ser Ala Ser Ser Pro Ile Glu Thr Ala Gly Arg Asn Met Leu Ser Leu
            530                 535                 540
Phe Pro Thr Ser Pro Val Thr Asp Asn Arg Asp Gly Ser Pro Gln Ala
545                 550                 555                 560
Cys Val Pro Asp Asn Pro Ala Arg Val Ile Lys Val Val Pro His Asn
                565                 570                 575
Ala Arg Ser Ala Thr Glu Ser Val Ala Arg Ile Phe Gln Ser Ile Gln
                580                 585                 590
Gln Glu Arg Asn Asn Met Thr
            595
```

<210> SEQ ID NO 60
<211> LENGTH: 1972
<212> TYPE: DNA
<213> ORGANISM: Brassica sp.
<220> FEATURE:
<221> NAME/KEY: exon
<222> LOCATION: (1)..(147)
<223> OTHER INFORMATION: partial
<221> NAME/KEY: exon
<222> LOCATION: (344)..(792)
<223> OTHER INFORMATION:
<221> NAME/KEY: exon
<222> LOCATION: (1505)..(1556)
<223> OTHER INFORMATION:
<221> NAME/KEY: exon
<222> LOCATION: (1649)..(1972)
<223> OTHER INFORMATION:
<221> NAME/KEY: Intron
<222> LOCATION: (148)..(343)
<223> OTHER INFORMATION:
<221> NAME/KEY: Intron
<222> LOCATION: (793)..(1504)
<223> OTHER INFORMATION:
<221> NAME/KEY: Intron
<222> LOCATION: (1557)..(1648)
<223> OTHER INFORMATION:

<400> SEQUENCE: 60

```
aaa gga gga gga cct cga gct cct cct aga aac aag atg gct ctc tac    48
Lys Gly Gly Gly Pro Arg Ala Pro Pro Arg Asn Lys Met Ala Leu Tyr
1               5                   10                  15
gag cac ctc acc acc cct tct cac agg ttt act gat cat agt tcc tcg    96
Glu His Leu Thr Thr Pro Ser His Arg Phe Thr Asp His Ser Ser Ser
                20                  25                  30
cca cgt cac acc aac act ctc ttt cct cct cct gga cca tct aac       144
Pro Arg His Thr Asn Thr Leu Phe Pro Pro Pro Gly Pro Ser Asn
            35                  40                  45
cag gtactactga gttttagta ataatatata ttagttacag caaatcttaa          197
Gln
tttcttgctg tgtcttatta ccatgtttcg tttgtggaaa tgattatctt ttaaagctat  257
aaccttcttg ttatgctgaa tagtttcagt agaagattat atagtgtatg tgggacattg  317
gaaataatta tctttttatt ctgcag cct tgt ggg gtg gag aga aac ttg act   370
                            Pro Cys Gly Val Glu Arg Asn Leu Thr
                                                50          55
tcc cag cat ctt gat tct tca gct tct ggc cat gta acc caa atg tcc    418
Ser Gln His Leu Asp Ser Ser Ala Ser Gly His Val Thr Gln Met Ser
        60                  65                  70
```

```
tcc atg gaa aat gtg aca act tta gca cat cgt cgt ggt gat caa agg      466
Ser Met Glu Asn Val Thr Thr Leu Ala His Arg Arg Gly Asp Gln Arg
 75                  80                  85                  90
aaa acg cta aga gag gaa gat gat ttt gcg gtt cct gta tat gtt aat      514
Lys Thr Leu Arg Glu Glu Asp Asp Phe Ala Val Pro Val Tyr Val Asn
                 95                 100                 105
gat agc tca aga aga ttt caa tgt cct ctt gaa aag tca gca tcg ggt      562
Asp Ser Ser Arg Arg Phe Gln Cys Pro Leu Glu Lys Ser Ala Ser Gly
            110                 115                 120
tgt gaa aga gtt aat gct tct tgt gag aca gag tct aca agt agt agg      610
Cys Glu Arg Val Asn Ala Ser Cys Glu Thr Glu Ser Thr Ser Ser Arg
        125                 130                 135
tta gac cat gaa act gga gtg atg gaa act gat gat gga gtt gaa tct      658
Leu Asp His Glu Thr Gly Val Met Glu Thr Asp Asp Gly Val Glu Ser
    140                 145                 150
cat ggc aat cct aat gac gtc gat gat gat gat gat gat tcg ata          706
His Gly Asn Pro Asn Asp Val Asp Asp Asp Asp Asp Asp Ser Ile
155                 160                 165                 170
tcc agc ata gac gtc tct gat gaa gtt gtg gga gta tta ggt caa          754
Ser Ser Ile Asp Val Ser Asp Glu Val Val Gly Val Leu Gly Gln
                175                 180                 185
aac cgk ttc tgg aga gca agg aar gct atk gcc aag aa gtycctcata        802
Asn Arg Phe Trp Arg Ala Arg Lys Ala Xaa Ala Lys Asn
            190                 195
gacttttggt gaactggtaa ggaatttttt gggtctttct ctgctgtttt aatgcttaaa    862
tgatgcaatg gtttgctcac aacatacata tatgattata actctgcttt atattttgaa    922
aaagaccaga tttggtttat ttttgattga aagtgataa tttttagtg aagaaacccc      982
ctgactcctc caaaaattga aggttcccgc cgagacagtt aatggatttt gcatctgctt   1042
gctggaacat gtccctgcc ctgtctcggt ttggtatttg cttttattct gcattttccc    1102
ttcttgtcat tcaacgggtt gaaccaggta gttaaccata cataaagcta gttatgtgtc   1162
ttatgaaaat gaagaattat agtagcagag gttgtaaact atggagtttt ctatggattt   1222
tagactctgt tactcaggtt ttaaggttct atgtaaggta tcaattaaac ccaccccttg   1282
cataatgtct tcagtttttc ttcttctatt atttatgcct ttctctgtgt tttttgacgc   1342
attgatttgc ttcttcatca ttgttggtta gaggcttctt gcttcttttt ttttccgatt   1402
ctactgttct attatttgtt caaccgaaac tatatctatc tctctttgtg gaacttttct   1462
tatgggtcat cttcttgatc tgaccttgtt tctccgtaac ag t caa caa aga ata    1517
                                                Gln Gln Arg Ile
                                                        200
ttt gcg gtt caa tta ttt gag ttg cac agg ctr att aag gtaaaactca      1566
Phe Ala Val Gln Leu Phe Glu Leu His Arg Xaa Ile Lys
    205                 210                 215
ttcagaaaac ttctcctacg tttcatgaat atttgttttg tgcaaaccta gtcaactgta   1626
ctttgttttc actataatca ag gtt caa aga ctt att gct tca tca tcg gat    1678
                        Val Gln Arg Leu Ile Ala Ser Ser Ser Asp
                                220                 225
gtc ttg ctc gat gag atc agt tat ctt gga aat gtt cca gtg aag aag     1726
Val Leu Leu Asp Glu Ile Ser Tyr Leu Gly Asn Val Pro Val Lys Lys
            230                 235                 240
ctt ctt ccc tct gaa ttt ata tta aag cct cct cct cta cca cag gtt     1774
Leu Leu Pro Ser Glu Phe Ile Leu Lys Pro Pro Pro Leu Pro Gln Val
        245                 250                 255
acc aaa cac aga agc agc gac tcc gag aag act gac caa aat aaa atg     1822
Thr Lys His Arg Ser Ser Asp Ser Glu Lys Thr Asp Gln Asn Lys Met
    260                 265                 270
gaa tcc tca gct gag aac gta gtc ggg aag tcg tca aac caa ggt cag     1870
Glu Ser Ser Ala Glu Asn Val Val Gly Lys Ser Ser Asn Gln Gly Gln
275                 280                 285                 290
cag cat caa ccg tcc aac tac atg cct ttt gcg agc aac cca cca gct     1918
Gln His Gln Pro Ser Asn Tyr Met Pro Phe Ala Ser Asn Pro Pro Ala
                295                 300                 305
gca aat gga tgt tac tat cct cct cag cat cct cct ccc tct gga gga     1966
Ala Asn Gly Cys Tyr Tyr Pro Pro Gln His Pro Pro Pro Ser Gly Gly
            310                 315                 320
aat cag                                                             1972
Asn Gln
```

<210> SEQ ID NO 61
<211> LENGTH: 324
<212> TYPE: PRT
<213> ORGANISM: Brassica sp.
<220> FEATURE:
<221> NAME/KEY: misc_feature
<222> LOCATION: (188)..(188)
<223> OTHER INFORMATION: Xaa = uncertain amino acid residue
<221> NAME/KEY: misc_feature
<222> LOCATION: (194)..(194)
<223> OTHER INFORMATION: Xaa = uncertain amino acid residue
<221> NAME/KEY: misc_feature

```
<222> LOCATION: (196)..(196)
<223> OTHER INFORMATION: Xaa = uncertain amino acid residue
<221> NAME/KEY: misc_feature
<222> LOCATION: (214)..(214)
<223> OTHER INFORMATION: Xaa = uncertain amino acid residue

<400> SEQUENCE: 61

Lys Gly Gly Gly Pro Arg Ala Pro Pro Arg Asn Lys Met Ala Leu Tyr
 1               5                  10                  15
Glu His Leu Thr Thr Pro Ser His Arg Phe Thr Asp His Ser Ser Ser
             20                  25                  30
Pro Arg His Thr Asn Thr Leu Phe Pro Pro Pro Gly Pro Ser Asn
         35                  40                  45
Gln Pro Cys Gly Val Glu Arg Asn Leu Thr Ser Gln His Leu Asp Ser
 50                  55                  60
Ser Ala Ser Gly His Val Thr Gln Met Ser Ser Met Glu Asn Val Thr
 65                  70                  75                  80
Thr Leu Ala His Arg Arg Gly Asp Gln Arg Lys Thr Leu Arg Glu Glu
                 85                  90                  95
Asp Asp Phe Ala Val Pro Val Tyr Val Asn Asp Ser Ser Arg Arg Phe
             100                 105                 110
Gln Cys Pro Leu Glu Lys Ser Ala Ser Gly Cys Glu Arg Val Asn Ala
         115                 120                 125
Ser Cys Glu Thr Glu Ser Thr Ser Ser Arg Leu Asp His Glu Thr Gly
130                 135                 140
Val Met Glu Thr Asp Asp Gly Val Glu Ser His Gly Asn Pro Asn Asp
145                 150                 155                 160
Val Asp Asp Asp Asp Asp Ser Ile Ser Ser Ile Asp Val Ser
                165                 170                 175
Ser Asp Glu Val Val Gly Val Leu Gly Gln Asn Xaa Phe Trp Arg Ala
            180                 185                 190
Arg Xaa Ala Xaa Ala Lys Asn Gln Gln Arg Ile Phe Ala Val Gln Leu
        195                 200                 205
Phe Glu Leu His Arg Xaa Ile Lys Val Gln Arg Leu Ile Ala Ser Ser
    210                 215                 220
Ser Asp Val Leu Leu Asp Glu Ile Ser Tyr Leu Gly Asn Val Pro Val
225                 230                 235                 240
Lys Lys Leu Leu Pro Ser Glu Phe Ile Leu Lys Pro Pro Leu Pro
                245                 250                 255
Gln Val Thr Lys His Arg Ser Ser Asp Ser Glu Lys Thr Asp Gln Asn
            260                 265                 270
Lys Met Glu Ser Ser Ala Glu Asn Val Val Gly Lys Ser Ser Asn Gln
        275                 280                 285
Gly Gln Gln His Gln Pro Ser Asn Tyr Met Pro Phe Ala Ser Asn Pro
    290                 295                 300
Pro Ala Ala Asn Gly Cys Tyr Tyr Pro Pro Gln His Pro Pro Pro Ser
305                 310                 315                 320
Gly Gly Asn Gln

<210> SEQ ID NO 62
<211> LENGTH: 505
<212> TYPE: DNA
<213> ORGANISM: Brassica
<220> FEATURE:
<221> NAME/KEY: exon
<222> LOCATION: (2)..(505)
<223> OTHER INFORMATION:

<400> SEQUENCE: 62 a ccc ggt cca gat ccg ggg cac acg ggg ccg gtc tgt gga ggg tat tat      49
  Pro Gly Pro Asp Pro Gly His Thr Gly Pro Val Cys Gly Gly Tyr Tyr
   1               5                  10                  15
ggt cat ttc atg cct gca cca atg ttc atg ggt ggt ggt ggt ggt cag       97
Gly His Phe Met Pro Ala Pro Met Phe Met Gly Gly Gly Gly Gly Gln
             20                  25                  30
cct cct ccg ttt cac ccg ggc atg gga ttc cya tct cat ggt aat ggc      145
Pro Pro Pro Phe His Pro Gly Met Gly Phe Xaa Ser His Gly Asn Gly
         35                  40                  45
tac ttt cct cca tat ggt ggt atc atg atg aac cct tac tat tcc gga      193
Tyr Phe Pro Pro Tyr Gly Gly Ile Met Met Asn Pro Tyr Tyr Ser Gly
 50                  55                  60
cra caa caa caa caa ccc aat gag caa atg aac aac aac atc caa           241
Xaa Gln Gln Gln Gln Pro Asn Glu Gln Met Asn Asn Asn Ile Gln
 65                  70                  75                  80
caa cag agc tca gtg aat gaa gcg act tca caa caa caa cag cca acg      289
Gln Gln Ser Ser Val Asn Glu Ala Thr Ser Gln Gln Gln Gln Pro Thr
```

```
                      85                  90                  95
    aaa tct tat cct cgg gct aaa aag agc agg caa gag gga atc tct ggt      337
    Lys Ser Tyr Pro Arg Ala Lys Lys Ser Arg Gln Glu Gly Ile Ser Gly
                    100                 105                 110
    aag aag aag tcc ttt caa cca ttc tca gcg gtt gat gat gtt cat gat      385
    Lys Lys Lys Ser Phe Gln Pro Phe Ser Ala Val Asp Asp Val His Asp
                115                 120                 125
    gac aag atc aac aat gct gca caa cct act gag gaa atg atg acg aca      433
    Asp Lys Ile Asn Asn Ala Ala Gln Pro Thr Glu Glu Met Met Thr Thr
            130                 135                 140
    acc aca acc aca aca act gtg act cag aca acg aga gat gga gca          481
    Thr Thr Thr Thr Thr Thr Val Thr Gln Thr Thr Arg Asp Gly Ala
    145                 150                 155                 160
    gga gtg acg aga gtg atc aag gtg                                      505
    Gly Val Thr Arg Val Ile Lys Val
                    165
```

<210> SEQ ID NO 63
<211> LENGTH: 168
<212> TYPE: PRT
<213> ORGANISM: Brassica sp.
<220> FEATURE:
<221> NAME/KEY: misc_feature
<222> LOCATION: (43)..(43)
<223> OTHER INFORMATION: Xaa = uncertain amino acid residue
<221> NAME/KEY: misc_feature
<222> LOCATION: (65)..(65)
<223> OTHER INFORMATION: Xaa = uncertain amino acid residue

<400> SEQUENCE: 63

```
    Pro Gly Pro Asp Pro Gly His Thr Gly Pro Val Cys Gly Gly Tyr Tyr
    1               5                   10                  15
    Gly His Phe Met Pro Ala Pro Met Phe Met Gly Gly Gly Gly Gly Gln
                    20                  25                  30
    Pro Pro Pro Phe His Pro Gly Met Gly Phe Xaa Ser His Gly Asn Gly
                35                  40                  45
    Tyr Phe Pro Pro Tyr Gly Gly Ile Met Met Asn Pro Tyr Tyr Ser Gly
    50                  55                  60
    Xaa Gln Gln Gln Gln Pro Asn Glu Gln Met Asn Asn Asn Ile Gln
    65                  70                  75                  80
    Gln Gln Ser Ser Val Asn Glu Ala Thr Ser Gln Gln Gln Gln Pro Thr
                    85                  90                  95
    Lys Ser Tyr Pro Arg Ala Lys Lys Ser Arg Gln Glu Gly Ile Ser Gly
                    100                 105                 110
    Lys Lys Lys Ser Phe Gln Pro Phe Ser Ala Val Asp Asp Val His Asp
                115                 120                 125
    Asp Lys Ile Asn Asn Ala Ala Gln Pro Thr Glu Glu Met Met Thr Thr
            130                 135                 140
    Thr Thr Thr Thr Thr Thr Val Thr Gln Thr Thr Arg Asp Gly Ala
    145                 150                 155                 160
    Gly Val Thr Arg Val Ile Lys Val
                    165
```

<210> SEQ ID NO 64
<211> LENGTH: 36
<212> TYPE: DNA
<213> ORGANISM: synthetic oligonucleotide
<220> FEATURE:
<221> NAME/KEY: misc_feature
<222> LOCATION: (28)..(28)
<223> OTHER INFORMATION: n = any nucleic acid residue

<400> SEQUENCE: 64

```
    tgttatgtct ccttctgaag gactgrtnta yaarcc                               36
```

<210> SEQ ID NO 65
<211> LENGTH: 35
<212> TYPE: DNA
<213> ORGANISM: synthetic oligonucleotide
<220> FEATURE:
<221> NAME/KEY: misc_feature
<222> LOCATION: (30)..(30)
<223> OTHER INFORMATION: n = any nucleic acid
<221> NAME/KEY: misc_feature

```
<222> LOCATION: (33)..(33)
<223> OTHER INFORMATION: n = any nucleic acid

<400> SEQUENCE: 65
gcagattcag aagcagttct agcaktrtgn ggnac                         35

<210> SEQ ID NO 66
<211> LENGTH: 35
<212> TYPE: DNA
<213> ORGANISM: synthetic oligonucleotide
<220> FEATURE:
<221> NAME/KEY: misc_feature
<222> LOCATION: (33)..(33)
<223> OTHER INFORMATION: n = any nucleic acid

<400> SEQUENCE: 66
caaagagttt ttgctgttca agttttygar ytnca                         35

<210> SEQ ID NO 67
<211> LENGTH: 20
<212> TYPE: DNA
<213> ORGANISM: synthetic oligonucleotide

<400> SEQUENCE: 67
tcaatcagtc acctgggcat                                          20

<210> SEQ ID NO 68
<211> LENGTH: 35
<212> TYPE: DNA
<213> ORGANISM: synthetic oligonucleotide
<220> FEATURE:
<221> NAME/KEY: misc_feature
<222> LOCATION: (9)..(9)
<223> OTHER INFORMATION: n = any nucleic acid

<400> SEQUENCE: 68
cartggytnr ttcctgttat gtctccttct gaagg                         35
```